United States Patent [19]
Bartroli et al.

[11] Patent Number: 5,888,941
[45] Date of Patent: Mar. 30, 1999

[54] CARBOZAMIDES WITH ANTIFUNGAL ACTIVITY

[75] Inventors: Javier Bartroli; Enric Turmo; Manuel Anguita, all of Barcelona, Spain

[73] Assignee: J. Uriach & Cia. S.A., Barcelona, Spain

[21] Appl. No.: 809,815

[22] PCT Filed: Aug. 2, 1996

[86] PCT No.: PCT/EP96/03419

§ 371 Date: Mar. 31, 1997

§ 102(e) Date: Mar. 31, 1997

[87] PCT Pub. No.: WO97/05131

PCT Pub. Date: Feb. 13, 1997

[30] Foreign Application Priority Data

Aug. 2, 1995 [ES] Spain .................................. 9501564
Oct. 20, 1995 [ES] Spain .................................. 9502042

[51] Int. Cl.[6] ...................... C07D 403/12; C07D 417/12; C07D 409/14; A61K 31/41

[52] U.S. Cl. .......................... 504/262; 504/263; 504/265; 504/266; 504/269; 504/270; 504/271; 504/272; 514/361; 514/363; 514/364; 514/365; 514/372; 514/374; 514/378; 514/383; 548/125; 548/128; 548/136; 548/143; 548/204; 548/214; 548/236; 548/239; 548/262.2; 548/267.4

[58] Field of Search .............................. 548/266.2, 267.6, 548/204, 214, 236, 239, 247, 143, 136, 125, 128; 514/365, 383, 361, 363, 364, 372, 374, 378; 504/266, 272, 262, 263, 265, 269, 270, 271

[56] References Cited

FOREIGN PATENT DOCUMENTS

| | | |
|---|---|---|
| 0 097 469 | 1/1984 | European Pat. Off. . |
| 97469-A | 1/1984 | European Pat. Off. . |
| 239500A | 9/1987 | European Pat. Off. . |
| 0 332 387 | 9/1989 | European Pat. Off. . |
| 332387A | 9/1989 | European Pat. Off. . |
| 357241A | 3/1990 | European Pat. Off. . |
| 567982A | 11/1993 | European Pat. Off. . |
| 0 617 031 | 9/1994 | European Pat. Off. . |
| 2062941A | 12/1994 | Spain . |

OTHER PUBLICATIONS

CAS print out of EP 332387, Sep. 13, 1989.
Chemical Abstracts, "Investigations of β–dialdehydes. I. Carbethoxymalonaldehyde", vol. 40, 7163.
J. Med. Chem 1995, 38, 1355–1371, "Picornavirus Inhibitors: Trifluoremthyl Substitution Provides a Global Protective Effect against Hepatic Metabolism", Guy D. Diana et al.
J. Heterocyclic Chem. 24, 1669 (1987), "Reactionof 2–Dimethylaminomethylene–1, 3–diones with Dinucleophiles, VI. Synthesis of Ethyl or Methyl 1, 5–disubstituted 1H–Pyrazole–4–carboxylates",Giulia Menozzi et al, Nov–Dec 1987.
Journal f. prakt. Chemie. Band 327, Heft 1. 1985, S. 109–116, "Preparation of 1, 3, 4–Oxadiazol–2–carboxylic Acid Derivatives", J. Dost et al.
Tetranedrin Letters No. 11, pp. 1317–1319, 1968, Eine neue Synthese substituierter Thiophene und Pyrrcle, S. Hauptmann et al.
Communications, Mar. 1984, A Simple Method for the Synthesis of 5–Aryl–3–amino–2–alkoxycarbonylthiophenes, Hartmann et al.
J. Org. Chem., vol. 42, No. 10, 1977, "Nitrile Sulfides, Synthesis of 5–Aryl–1, 2, 4–thiadiazole–3–carboxylates", Robert K. Howe et al, Nov. 1976.
31. Heilmittelchemische Studien in der heterocyclischen Reihe, Pyrazolo–pyrimidine 111[2] ,Paraxanthin–, Theobromin– und Theophyllin–Analoga der Pyrazolo[3, 4–d]pyrimidin–Reihe[3] , Volumen XLII, Fasciculus I (1959), No. 30–31, von P. Schmidt et al.
Eur. J. Med. Chem.—Chimica Therapeutica, "Synthese et proprietes antilipolytiques et hypotriglyceridemiantes d'acides thiazole–5 carboxyliques", Nov.–Dec. 1976, vol. 11, No. 6, p. 567.
OPPI Briefs, "A New Efficient Synthesis of 3–Amino–1–Phenylpyrrole", Frederic Fabis et al, vol. 27, No. 2, 1995.
Bull. Chem. Soc. Jpn., 58, 2519–2522 (1985), "A New Synthetic Method of Alkyl Carbonocyanidate N–Oxides", Tomio Shimizu et al.
The Journal of Organic Chemistry, "Aldo Condensation of Evans Chiral Enolates with Acetophenones. Its Application to the Stereoselective Synthesis of Homochiral Antifungal Agents", Javier Bartroli et al.
Organic Syntheses, "Methyl p–Tolyl Sulfone", L. Field et al, p. 674.
Organic Syntheses, "Kryptopyrrole (2, 4–Dimethyl–3–ethylpyrrole)", Hans Fischer, p. 67.
New Compounds, "Possible Anthelmintie Thiazol–5–ylbenzimidazoles. III", J.M. Singh, Feb. 23, 1968.

Primary Examiner—Mukund J. Shah
Assistant Examiner—Bruck Kifle
Attorney, Agent, or Firm—Burns, Doane, Swecker & Mathis, L.L.P.

[57] ABSTRACT

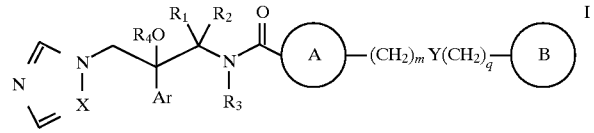

Compounds of general formula I and their salts and solvates are antifungal agents and as such are useful in the treatment of various fungal infections. Pharmaceutical compositions including these compounds and processes for their preparation are also provided.

19 Claims, No Drawings

CARBOZAMIDES WITH ANTIFUNGAL ACTIVITY

FIELD OF THE INVENTION

The present invention relates to a new series of carboxamides of general formula I having potent antifungal activity. The invention also relates to a process for their preparation, to pharmaceutical compositions containing them and to their use for the treatment of fungal diseases.

DESCRIPTION OF THE PRIOR ART

The compounds of the present invention are antifungal agents belonging to the azole class, whose mechanism of action is based on the inhibition of the biosynthesis of ergosterol, the main sterol present in fungi membranes.

Other antifungal agents having this mechanism of action have been reported in the literature. Patent applications EP 332387 and EP 617031 describe azole derivatives containing an arylcarboxamide group. The compounds of the present invention are not only more potent antifungal agents than the compounds described in the above two patents but they also have a broader spectrum of antifungal activity since, unlike the compounds described therein, they are also effective against filamentous fungi, including aspergillus.

DESCRIPTION OF THE INVENTION

The present invention relates to new carboxamides of general formula I

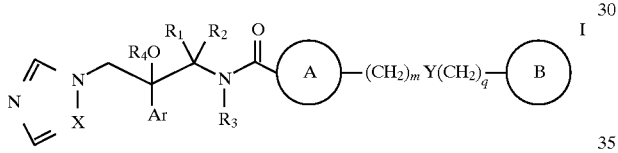

as racemates, diastereomer mixtures or as pure enantiomers, wherein:

X represents N or CH;

Ar represents phenyl or phenyl substituted with one or more halogen and/or trifluoromethyl groups;

$R_1$ is $C_1$–$C_4$ alkyl;

$R_2$ is hydrogen or $C_1$–$C_4$ alkyl;

or $R_1$ together with $R_2$ form a $C_2$–$C_4$ polymethylene chain;

$R_3$ is hydrogen, $C_1$–$C_4$ alkyl, $C_3$–$C_6$ cycloalkyl, $C_3$–$C_6$ cycloalkyl-$C_1$–$C_4$ alkyl, $C_1$–$C_4$ haloalkyl, phenyl-$C_1$–$C_4$ alkyl (wherein the phenyl group can be optionally substituted with 1, 2, 3 or 4 groups $R_5$, which can be the same or different), a group —$(CH_2)_n$—$CH_2OH$, a group —$(CH_2)_n$—$CH_2OBn$, a group —$(CH_2)_n$—$CH_2NR_6R_7$, a group —$(CH_2)_n$—$CH_2COOR_6$, or a group —$(CH_2)_n$—$CH_2COOB_n$, in which case $R_4$ is hydrogen;

or $R_3$ together with $R_4$ and the remainder of said compound of formula I form an oxazolidine ring of formula I'

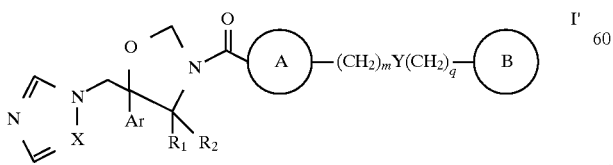

or $R_3$ together with $R_4$ and the remainder of said compound of formula I form a morpholine ring of formula I"

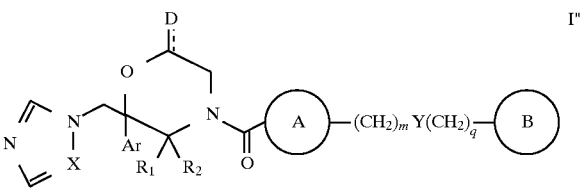

wherein D is O, in which case the dotted line represents a covalent bond, or D is hydroxy or hydrogen, in which case the dotted line is absent;

A represents phenyl or a monocyclic or bicyclic heterocyclic group containing from 1 to 4 heteroatoms selected from N, O and S and with each ring in the heterocyclic group being formed of 5 or 6 atoms, wherein A can be unsubstituted or have 1, 2, 3 or 4 groups $R_8$;

B represents a phenyl group which can be optionally substituted with 1, 2, 3 or 4 groups $R_9$, or B represents a monocyclic or bicyclic heterocyclic group containing from 1 to 4 heteroatoms selected from N, O and S and with each ring in the heterocyclic group being formed of 5 or 6 atoms, which can be optionally substituted with 1, 2, 3 or 4 groups $R_9$;

$R_5$ represents $C_1$–$C_4$ alkyl, $C_1$–$C_4$ haloalkyl or halogen;

n represents 0, 1, 2 or 3;

$R_6$ and $R_7$ independently represent hydrogen or $C_1$–$C_4$ alkyl;

$R_8$ represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, phenyl (optionally substituted with a group halogen, cyano, $C_1$–$C_4$ haloalkyl or $C_1$–$C_4$ haloalkoxy), nitro, cyano, hydroxy, hydroxymethyl, a group —$NR_6R_7$, a group —$CONR_6R_7$, a group —$COR_6$, a group —$COOR_6$, or a group —$SO_zR_{10}$;

$R_9$ represents $C_1$–$C_4$ alkyl, $C_2$–$C_4$-alkenyl, $C_2$–$C_4$-alkynyl, $C_3$–$C_6$ cycloalkyl, $C_1$–$C_4$ haloalkyl, $C_1$–$C_4$ alkoxy, $C_1$–$C_4$ haloalkoxy, 2-carboxy-2-propyl, halogen, nitro, cyano, hydroxy, benzyloxy, hydroxymethyl, a group —$CH_2$—$OCO$—$R_6$, a group —$CO$—$R_6$, a group —$COO$—$R_6$, a group —$SO_zR_{10}$, a group —$NR_6R_7$, a group —$CONR_6R_7$, a group —$C(=NR_6)NHR_{11}$, a group —$C(=NR_{11})OR_6$, and additionally one of the groups $R_9$ can also represent 1-pyrrolyl, 1-imidazolyl, 1H-1,2,4-triazol-1-yl, 5-tetrazolyl (optionally substituted with $C_1$–$C_4$ alkyl), 1-pyrrolidinyl, 4-morpholinyl, 4-morpholinyl-N-oxide, phenyl or phenoxy (both optionally substituted with a group $C_1$–$C_4$ alkyl, $C_1$–$C_4$ haloalkyl, $C_1$–$C_4$ alkoxy, $C_1$–$C_4$ haloalkoxy, halogen, nitro or cyano), or a group of formula (i)–(iv)

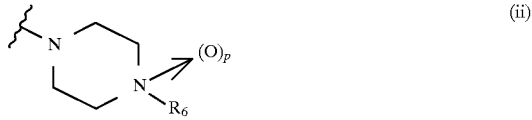

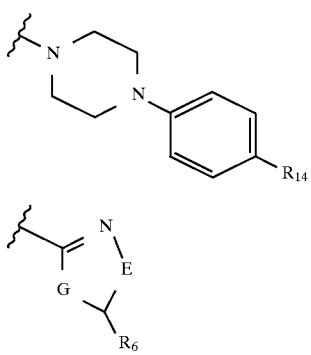

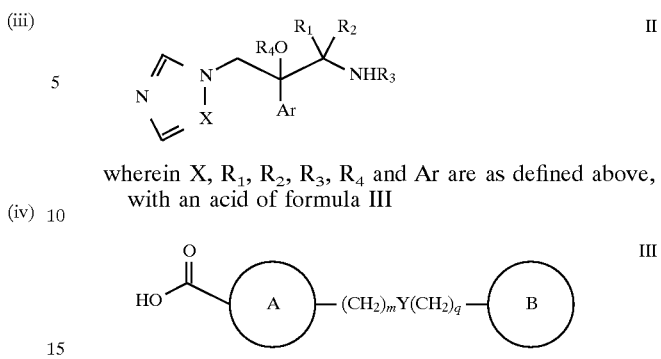

$R_{10}$ represents $C_1$–$C_4$ alkyl;

z represents 0, 1 or 2;

$R_1$ represents hydrogen, —$CONH_2$, —COMe, —CN, —$SO_2NHR_6$, —$SO_2R_{10}$, —$OR_6$, or —$OCOR_6$;

$R_{12}$ represents hydrogen or methyl;

$R_{13}$ represents hydrogen, isopropyl, cyclopentyl, cyclopropyl, 2-butyl, 3-pentyl, 3-hydroxy-2-butyl, or 2-hydroxy-3-pentyl;

p represents 0 or 1;

$R_{14}$ represents halogen, $C_1$–$C_4$ haloalkyl, $C_1$–$C_4$ haloalkoxy, nitro, amino, cyano, or a group of formula (i);

E represents —$CH_2$— or —C(=O)—;

G represents NH or O;

Y represents a single bond, —S—, —SO—, —$SO_2$—, —O— or —$NR_6$—;

m and q independently represent 0, 1 or 2; and the salts and solvates thereof.

The invention also provides a pharmaceutical composition which comprises an effective amount of a compound of formula I or a pharmaceutically acceptable salt or solvate thereof in admixture with one or more pharmaceutically acceptable excipients.

The invention further provides the use of a compound of formula I or a pharmaceutically acceptable salt or solvate thereof for the manufacture of a medicament for the treatment or prophylaxis of fungal infections in animals, including human beings.

The invention further provides the use of a compound of formula I or a pharmaceutically acceptable salt or solvate thereof for the treatment or prophylaxis of fungal infections in animals, including human beings.

The invention also provides a method of treating or preventing fungal infections in animals, including human beings, which method comprises administering to a patient in need thereof an effective amount of a compound of formula I or a pharmaceutically acceptable salt or solvate thereof.

In addition to being useful for the treatment of fungal infections in animals, the compounds of the present invention possess antifungal properties which can be useful for combatting or preventing plant fungal infections. The invention thus provides the use of a compound of formula I or a salt or solvate thereof for the treatment or prophylaxis of fungal infections in plants.

The invention still further provides an agrochemical composition which comprises an effective amount of a compound of formula I or a salt or solvate thereof in admixture with one or more agrochemically acceptable excipients.

The invention also provides a process for preparing a compound of formula I, which comprises:

(a) reacting a compound of formula II

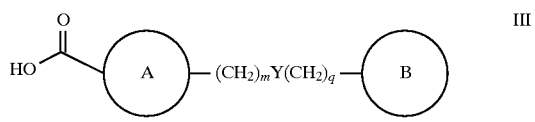

wherein X, $R_1$, $R_2$, $R_3$, $R_4$ and Ar are as defined above, with an acid of formula III wherein A, B, Y, m and q are as defined above, in the presence of a condensing agent, or with a reactive derivative of said acid III such as the acid chloride, the anhydride or the mixed anhydride in the presence of a proton scavenger base; or (b) converting in one or a plurality of steps a compound of formula I into another compound of formula I; and (c) if desired, after steps (a) or (b), reacting a compound of formula I with an acid to give the corresponding acid addition salt.

In the above definitions, the term $C_1$–$C_4$ alkyl, as a group or part of a group, means a linear or branched alkyl chain containing from 1 to 4 carbon atoms. Therefore, it includes methyl, ethyl, propyl, isopropyl, butyl, isobutyl, sec-butyl, and tert-butyl.

A $C_2$–$C_4$ alkenyl group means a linear or branched alkyl chain containing from 2 to 4 carbon atoms and additionally containing one or more double bonds. Examples include ethenyl, 1-propenyl, 2-propenyl, isopropenyl, 1-butenyl, 2-butenyl, 3-butenyl, and 1,3-butadienyl.

A $C_2$–$C_4$ alkynyl group means a linear or branched alkyl chain containing from 2 to 4 carbon atoms and additionally containing one or more triple bonds. Examples include ethynyl, 1-propynyl, 2-propynyl, 1-butynyl, 2-butynyl, and 3-butynyl.

A $C_2$–$C_4$ polymethylene chain means ethylene, propylene or butylene.

A $C_1$–$C_4$ haloalkyl group means a group resulting from the substitution of one or more hydrogen atoms of a $C_1$–$C_4$ alkyl group by one or more halogen atoms (i.e. fluorine, chlorine, bromine or iodine), which can be the same or different. Examples include trifluoromethyl, trichloromethyl, fluoromethyl, chloromethyl, bromomethyl, iodomethyl, difluoromethyl, dichloromethyl, 2-chloroethyl, 2,2-dichloroethyl, 2,2,2-trichloroethyl, pentachloroethyl, 2-fluoroethyl, 2,2-difluoroethyl, 2,2,2-trifluoroethyl, pentafluoroethyl, 3-chloropropyl, 3,3-dichloropropyl, 3,3,3-trichloropropyl, 2,2,3,3,3-pentachloropropyl, 3-fluoropropyl, 3,3-difluoropropyl, 3,3,3-trifluoropropyl, 2,2,3,3-tetrafluoropropyl, 2,2,3,3,3-pentafluoropropyl, heptafluoropropyl, 4-chlorobutyl, 4-fluorobutyl, 4-iodobutyl and 4-bromobutyl.

The term $C_3$–$C_6$ cycloalkyl, as a group or part of a group, represents cyclopropyl, cyclobutyl, cyclopentyl or cyclohexyl.

The abbreviation Bn represents benzyl.

A $C_1$–$C_4$ alkoxy group means a group derived from the union of a $C_1$–$C_4$ alkyl group to an oxygen atom of an ether functional group. Examples include methoxy, ethoxy, propoxy, isopropoxy, butoxy, isobutoxy, sec-butoxy and tert-butoxy.

A $C_1$–$C_4$ haloalkoxy group means a group resulting from the substitution of one or more hydrogen atoms of a $C_1$–$C_4$ alkoxy group by one or more halogen atoms, which can be the same or different. Examples include trifluoromethoxy, fluoromethoxy, 2-chloroethoxy, 2-fluoroethoxy, 2-iodoethoxy, 2,2-difluoroethoxy, 2,2,2-trifluoroethoxy, pentafluoroethoxy, 3-fluoropropoxy, 3-chloropropoxy, 2,2,3, 3-tetrafluoropropoxy, 2,2,3,3,3-pentafluoropropoxy, heptafluoropropoxy, 4-fluorobutoxy, and 4-chlorobutoxy.

In the compounds of the present invention Ar represents a phenyl group or a phenyl group substituted with one or more halogen and/or trifluoromethyl groups. The halogen atoms may be fluorine, chlorine, bromine or iodine atoms, of which fluorine and chlorine atoms are preferred. There may be one or more such substituents on the phenyl group, and where there are more than one, these may be the same or different. When the phenyl group is substituted, the substituents can be on any available position of the phenyl ring, but they are preferably on the 2- and/or 4-positions. Examples of substituted phenyl groups include 4-(trifluoromethyl)phenyl, 2-fluorophenyl, 4-fluorophenyl, 2-chloro-4-fluorophenyl, 4-chloro-2-fluorophenyl, 4-bromophenyl, 2-fluoro-4-iodophenyl, 2,4-dichlorophenyl, 2,4-difluorophenyl, 4-chlorophenyl and 2-fluoro-4-(trifluoromethyl)phenyl, of which 2-fluorophenyl, 4-fluorophenyl, 2-chloro-4-fluorophenyl, 2,4-dichlorophenyl, 2,4-difluorophenyl, 4-(trifluoromethyl)phenyl and 4-chlorophenyl are preferred, and 2-fluorophenyl, 2,4-dichlorophenyl, 2,4-difluorophenyl, 4-(trifluoromethyl)phenyl and 4-chlorophenyl are more preferred.

In the compounds of the present invention $R_1$ represents a $C_1$–$C_4$ alkyl group, or together with $R_2$ forms a $C_2$–$C_4$ polymethylene chain, but preferably $R_1$ is $C_1$–$C_4$ alkyl, and more preferably $R_1$ is methyl.

In the compounds where $R_2$ is hydrogen or $C_1$–$C_4$ alkyl, or together with $R_1$ forms a $C_2$–$C_4$ polymethylene chain, those wherein $R_2$ is hydrogen or methyl are preferred, and those wherein $R_2$ is hydrogen are more preferred.

From among the compounds wherein $R_3$ and $R_4$ are unconnected or can be bonded together forming an oxazolidine or morpholine ring, those wherein $R_3$ and $R_4$ are unconnected (i.e. $R_4$ represents hydrogen) are preferred, and those wherein both $R_3$ and $R_4$ represent hydrogen are more preferred.

In the compounds of the present invention, the groups A and B represent phenyl or a monocyclic or bicyclic heterocyclic group, wherein each ring in the heterocyclic group is formed of 5 or 6 atoms and wherein from 1 to 4 of the ring atoms forming said heterocyclic group are heteroatoms selected from the group consisting of N, O and S. Both A and B can be unsubstituted or have 1, 2, 3 or 4 substituents $R_8$ or $R_9$ respectively, which can be on any available position of any of the rings. When there is more than one substituents on ring A or B, they can be the same or different, provided that, as mentioned above, for certain meanings of $R_9$ there cannot be more than one such group on ring B. Examples of monocyclic heterocyclic groups A or B include thiophene, furan, pyran, pyrrole, imidazole, pyrazole, thiazole, isothiazole, oxazole, isoxazole, 1,2,4-triazole, 1,3,4-oxadiazole, 1,3,4-thiadiazole, 1,2,4-oxadiazole, 1,2,4-thiadiazole, pyridine, pyrazine, pyrimidine, pyridazine, furazan, pyrroline, imidazoline and pyrazoline. Examples of bicyclic heterocyclic groups A or B include among others benzimidazole, benzofuran, isobenzofuran, benzofurazan, indole, isoindole, indolizine, indazole, benzothiophene, benzothiazole, quinoline, isoquinoline, phtalazine, quinazoline, quinoxaline, cinnoline, imidazopyridine, imidazopyrimidine, imidazopyrazine, imidazopyridazine, pyrazolopyrazine, pyrazolopyridine and pyrazolopyrimidine.

Among all the possible meanings for A those wherein A represents phenyl or a 5- or 6-membered heterocyclic ring containing from 1 to 3 heteroatoms selected from N, O and S are preferred; those groups wherein A represents a 5- or 6-membered aromatic heterocyclic ring containing from 1 to 3 heteroatoms selected from N, O and S are more preferred; those wherein A represents a thiophene, furan, pyrrole, imidazole, pyrazole, thiazole, isothiazole, oxazole, isoxazole, 1,2,4-triazole, 1,3,4-oxadiazole, 1,3,4-thiadiazole, 1,2,4-oxadiazole, or 1,2,4-thiadiazole ring are still more preferred; and those wherein A represents thiophene, thiazole or pyrazole are particularly preferred. All these groups A can be unsubstituted or have 1, 2, 3 or 4, preferably 1 or 2, groups $R_8$. As preferred meanings for $R_8$ we can mention $C_1$–$C_4$ alkyl, $C_1$–$C_4$ haloalkyl, $C_1$–$C_4$ haloalkoxy, halogen and amino, of which $C_1$–$C_4$ alkyl and $C_1$–$C_4$ haloalkyl are more preferred.

As for B, those groups wherein B represents a phenyl group optionally substituted with 1, 2, 3 or 4 substituents $R_9$ are preferred. As examples of substituted phenyl rings we can mention among others 2-methylphenyl, 4-methylphenyl, 4-tert-butylphenyl, 4-(2-carboxy-2-propyl)phenyl, 4-vinylphenyl, 4-fluorophenyl, 4-chlorophenyl, 4-bromophenyl, 4-iodophenyl, 2,4-difluorophenyl, 3,4-difluorophenyl, 2,6-difluorophenyl, 2,4-dichlorophenyl, 2,5-dichlorophenyl, 2-chlorophenyl, 2-chloro-4-fluorophenyl, 2,4,6-trifluorophenyl, 2,3,5,6-tetrafluorophenyl, 2-(trifluoromethyl)phenyl, 3-(trifluoromethyl)phenyl, 4-(trifluoromethyl)phenyl, 4-(trichloromethyl)phenyl, 2-fluoro-5-(trifluoromethyl)phenyl, 2-fluoro-4-(trifluoromethyl)phenyl, 3-fluoro-4-(trifluoromethyl)phenyl, 4-(difluoromethoxy)phenyl, 4-(trifluoromethoxy)phenyl, 4-(2-fluoroethoxy)phenyl, 4-(2,2-difluoroethoxy)phenyl, 4-(2,2,2-trifluoroethoxy)phenyl, 4-(2,2,3,3-tetrafluoropropoxy)phenyl, 3-nitrophenyl, 4-nitrophenyl, 2-fluoro-4-nitrophenyl, 2-cyanophenyl, 3-cyanophenyl, 4-cyanophenyl, 4-(4-cyanophenyl)phenyl, 4-(4-cyanophenoxy)phenyl, 2-methyl-4-cyanophenyl, 2-chloro-4-cyanophenyl, 2-cyano-4-(trifluoromethyl)phenyl, 4-(methoxycarbonyl)phenyl, 2-methoxy-4-(trifluoromethyl)phenyl, 2-fluoro-4-(ethoxycarbonyl)phenyl, 4-(methylthio)phenyl, 4-(methylsulfinyl)phenyl, 4-(methylsulfonyl)phenyl, 4-aminophenyl, 4-dimethylaminophenyl and 4-carbamoylphenyl. More preferred meanings for B are those wherein B represents phenyl substituted with 1 or 2 groups $R_9$, of which those wherein one of the substituents $R_9$ is in the para position are still more preferred. Preferred meanings for $R_9$ include $C_1$–$C_4$ alkyl, $C_2$–$C_4$-alkenyl, $C_2$–$C_4$-alkynyl, $C_3$–$C_6$ cycloalkyl, $C_1$–$C_4$ haloalkyl, $C_1$–$C_4$ alkoxy, $C_1$–$C_4$ haloalkoxy, 2-carboxy-2-propyl, halogen, nitro, cyano, hydroxy, benzyloxy, hydroxymethyl, a group —$CH_2$—OCO—$R_6$, a group —CO—$R_6$, a group —COO—$R_6$, a group —$SO_2R_{10}$, a group —$NR_6R_7$, a group —$CONR_6R_7$, a group —$C(=NR_6)NHR_{11}$ or a group —$C(=NR_{11})OR_6$.

In the compounds wherein Y represents a single bond, —S—, —SO—, —$SO_2$—, —O— or —$NR_6$— and m and q independently represent 0, 1 or 2, those wherein Y represents a single bond and m=q=0, that is, those wherein ring B is directly bonded to ring A through a covalent bond are preferred.

Preferred compounds of the present invention include those in which, independently or in any compatible combination:

X represents N;
$R_1$ represents $C_1$–$C_4$ alkyl;
$R_2$ represents hydrogen;

R₄ represents hydrogen;

Ar represents 2-fluorophenyl, 4-fluorophenyl, 2-chloro-4-fluorophenyl, 2,4-dichlorophenyl, 2,4-difluorophenyl, 4-(trifluoromethyl)phenyl or 4-chlorophenyl;

A represents phenyl or a 5- or 6-membered heterocyclic ring containing from 1 to 3 heteroatoms selected from N, O and S, wherein A can be unsubstituted or have 1, 2, 3 or 4 groups $R_8$;

B represents a phenyl group which can be optionally substituted with 1, 2, 3 or 4 substituents $R_9$;

the stereochemistry of the compounds is (R,R).

Particularly preferred compounds of the present invention include those in which, independently or in any compatible combination:

X represents N;

$R_1$ represents methyl;

$R_2$ represents hydrogen;

$R_3$ represents hydrogen;

$R_4$ represents hydrogen;

Ar represents 2-fluorophenyl, 2,4-dichlorophenyl, 2,4-difluorophenyl, 4-(trifluoromethyl)phenyl or 4-chlorophenyl;

A represents a 5- or 6-membered aromatic heterocyclic ring containing from 1 to 3 heteroatoms selected from N, O and S, and which can be unsubstituted or have 1 or 2 groups $R_8$;

B represents a phenyl group substituted with 1 or 2 groups $R_9$;

Y represents a single bond and m=q=0;

the stereochemistry of the compounds is (R,R).

Accordingly, a preferred class of compounds of formula I is that wherein:

X represents N;

$R_1$ represents $C_1$–$C_4$ alkyl;

$R_2$ represents hydrogen;

$R_4$ represents hydrogen;

Ar represents 2-fluorophenyl, 4-fluorophenyl, 2-chloro-4-fluorophenyl, 2,4-dichlorophenyl, 2,4-difluorophenyl, 4-(trifluoromethyl)phenyl or 4-chlorophenyl;

A represents phenyl or a 5- or 6-membered heterocyclic ring containing from 1 to 3 heteroatoms selected from N, O and S, wherein A can be unsubstituted or have 1, 2, 3 or 4 groups $R_8$;

B represents a phenyl group which can be optionally substituted with 1, 2, 3 or 4 substituents $R_9$; and the stereochemistry of the compounds is (R,R).

A more preferred class of compounds of formula I is that wherein:

X represents N;

$R_1$ represents methyl;

$R_2$ represents hydrogen;

$R_3$ represents hydrogen;

$R_4$ represents hydrogen;

Ar represents 2-fluorophenyl, 2,4-dichlorophenyl, 2,4-difluorophenyl, 4-(trifluoromethyl)phenyl or 4-chlorophenyl;

A represents a 5- or 6-membered aromatic heterocyclic ring containing from 1 to 3 heteroatoms selected from N, O and S, and which can be unsubstituted or have 1 or 2 groups $R_8$;

B represents a phenyl group substituted with 1 or 2 groups $R_9$;

Y represents a single bond and m=q=0; and the stereochemistry of the compounds is (R,R).

A particularly preferred class of compounds of formula I is that wherein:

X represents N;

$R_1$ represents methyl;

$R_2$ represents hydrogen;

$R_3$ represents hydrogen;

$R_4$ represents hydrogen;

Ar represents 2-fluorophenyl, 2,4-dichlorophenyl, 2,4-difluorophenyl, 4-(trifluoromethyl)phenyl or 4-chlorophenyl;

A represents thiophene, furan, pyrrole, imidazole, pyrazole, thiazole, isothiazole, oxazole, isoxazole, 1,2,4-triazole, 1,3,4-oxadiazole, 1,3,4-thiadiazole, 1,2,4-oxadiazole, or 1,2,4-thiadiazole, wherein A can be optionally substituted with one or two $C_1$–$C_4$ alkyl or $C_1$–$C_4$ haloalkyl groups;

B represents a phenyl group substituted with 1 or 2 groups $R_9$;

$R_9$ represents $C_1$–$C_4$ alkyl, $C_2$–$C_4$-alkenyl, $C_2$–$C_4$-alkynyl, $C_3$–$C_6$ cycloalkyl, $C_1$–$C_4$ haloalkyl, $C_1$–$C_4$ alkoxy, $C_1$–$C_4$ haloalkoxy, 2-carboxy-2-propyl, halogen, nitro, cyano, hydroxy, benzyloxy, hydroxymethyl, a group —$CH_2$—OCO—$R_6$, a group —CO—$R_6$, a group —COO—$R_6$, a group —$SO_2R_{10}$, a group —$NR_6R_7$, a group —$CONR_6R_7$, a group —C(=$NR_6$)$NHR_{11}$ or a group —C(=$NR_{11}$)$OR_6$;

Y represents a single bond and m=q=0; and the stereochemistry of the compounds is (R,R).

The compounds of formula I contain one or more basic nitrogen atoms and, consequently, they can form salts with acids, which are also included in the present invention. There is no limitation on the nature of these salts, provided that, when used for therapeutic purposes, they are pharmaceutically acceptable, which, as is well-known in the art, means that they do not have reduced activity (or unacceptable reduced activity) or increased toxicity (or unacceptable increased toxicity) compared with the free compounds. Examples of these salts include: salts with an inorganic acid such as hydrochloric acid, hydrobromic acid, hydriodic acid, nitric acid, perchloric acid, sulfuric acid or phosphoric acid; and salts with an organic acid, such as methanesulfonic acid, trifluoromethanesulfonic acid, ethanesulfonic acid, benzenesulfonic acid, p-toluenesulfonic acid, fumaric acid, oxalic acid, maleic acid; and other mineral and carboxylic acids well known to those skilled in the art. The salts are prepared by reacting the free base with a sufficient amount of the desired acid to produce a salt in the conventional manner. Free bases and their salts differ in certain physical properties, such as solubility, but they are equivalent for the purposes of the invention.

Some compounds of the present invention can exist in solvated form, including hydrated forms. In general, the solvated forms, with pharmaceutically acceptable solvents such as water, ethanol and the like, are equivalent to the unsolvated forms for the purposes of the invention.

The compounds of formula I contain one or more asymmetric carbons and, consequently, can exist as different stereoisomers. The present invention covers both each of the individual stereoisomers and their mixtures. When $R_1$ is $C_1$–$C_4$ alkyl and $R_2$ is hydrogen, those compounds of formula I wherein the absolute configuration of the carbon atoms to which the Ar and $R_1$ groups are bonded is (R,R) are preferred, i.e. compounds of formula:

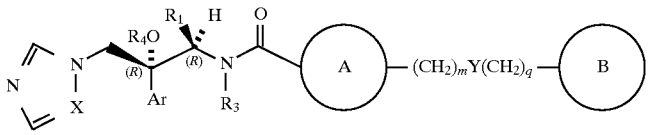

Diastereoisomers can be separated by conventional techniques such as chromatography or fractional crystallization. The optical isomers can be resolved using any of the conventional techniques of optical resolution to give optically pure isomers. Such a resolution can be performed in any chiral synthetic intermediate as well as in the products of general formula I. The optically pure isomers can also be individually obtained using enantiospecific synthesis. We have obtained the optically pure (R,R) isomers starting from optically pure amine II, prepared following the general procedure described in *J.Org.Chem*, 1995, 60, 3000–3012. As stated above, the present invention covers the individual isomers as well as their mixtures (e.g. racemic mixtures), whether as obtained by synthesis or by physically mixing them up.

Some of the compounds of formula I may present tautomerism. For example, when the compounds of the present invention contain an amidino group of formula —C(=NR$_6$)NHR$_{11}$, the following tautomeric structures may exist in equilibrium:

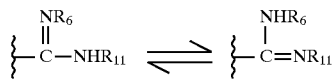

all of which are encompassed by the present invention.

The compounds of formula I can be prepared using the procedures described below. The precise method used for the preparation of a given compound may vary depending on its chemical structure.

The compounds of formula I can be prepared by reacting an amine of formula II with an acid of formula III in the presence of an appropriate condensing agent, for example dicyclohexylcarbodiimide, alone or in combination with 1-hydroxybenzotriazole, in a polar solvent, such as a substituted amide (for example N-methylpyrrolidone or dimethylformamide), an ether (for example tetrahydrofuran or dioxane) or diglyme, at a temperature preferably comprised between 0° C. and 100° C. Alternatively, compounds of formula I can be prepared by reacting an amine II with a reactive derivative of an acid III, such as the acid chloride, anhydride or mixed anhydride. The reaction is carried out in the presence of a proton scavenger base, such as triethylamine or pyridine, in a suitable solvent such as dichloromethane or chloroform.

Alternatively, compounds of formula I wherein Y represents —O—, —S— or —NR$_6$— and m is 0 can be prepared from the corresponding compound wherein A is substituted with a halogen atom, for example bromine, instead of a group —Y(CH$_2$)$_q$—B by treatment with an alkaline metal salt of the corresponding alcohol or thiol of formula HY(CH$_2$)$_q$—B, for example the sodium salt, or by treatment with an amine of formula HNR$_6$(CH$_2$)$_q$—B in a suitable aprotic solvent such as N-methylpyrrolidone at a temperature between room temperature and that of the refluxing solvent.

Moreover, some compounds of formula I can also be prepared by interconversion from another compound of formula I in one or a plurality of steps using reactions well known in organic chemistry, such as the reactions listed below. These reactions are mentioned here only as illustrative examples of the several procedures which can be used to interconvert compounds of the present invention and are not intended to limit the scope of the preparation of compounds of formula I in any way.

Thus, for example, the compounds of formula I wherein R$_3$ together with R$_4$ and the remainder of said compound of formula I form a morpholine ring of formula I", wherein D is hydrogen and the dotted line is absent, can be prepared from the corresponding compound of formula I wherein R$_3$=—(CH$_2$)$_2$OH by treatment with diethylazadicarboxylate and tributylphosphine in a suitable solvent such as tetrahydrofuran. The compounds of formula I wherein R$_3$ together with R$_4$ and the remainder of said compound of formula I form a morpholine ring of formula I", wherein D is hydroxy and the dotted line is absent, can be prepared from the corresponding compound of formula I wherein R$_3$=—(CH$_2$)$_2$OH by oxidation for example by treatment with activated DMSO and a base, such as triethylamine, in a suitable solvent, such as dichloromethane or chloroform. The compounds of formula I wherein R$_3$ together with R$_4$ and the remainder of said compound of formula I form a morpholine ring of formula I", wherein D is O and the dotted line represents a covalent bond, can be prepared from the corresponding compound of formula I wherein R$_3$=—CH$_2$COOH using a suitable dehydrating agent or alternatively they can be prepared from the corresponding compound of formula I wherein R$_3$=—(CH$_2$)$_2$OH by overoxidation.

Furthermore, it is also possible to convert a group R$_3$ in a compound of formula I into another group R$_3$ using standard methods of organic synthesis. Thus, a benzyl ether can be converted to the corresponding alcohol by hydrogenation in the presence of a suitable catalyst such as Pd/C in a suitable solvent such as an alcohol at a hydrogen pressure between 1 and 5 atm. An ester group can be hydrolized to the corresponding acid using conventional procedures; in case of benzyl esters, this conversion can be carried out by hydrogenation in the same experimental conditions mentioned above. An ester group can also be reduced by treatment with a suitable metal hydride such as sodium borohydride in a suitable solvent such as ethanol to give the corresponding alcohol.

It is also possible to use a group B in a compound of formula I to generate other groups B thus giving rise to other compounds of formula I. For example, a nitro group can be reduced to an amino group, for example by hydrogenation in the presence of a catalyst such as Pd/C in a suitable solvent such as an alcohol, for example ethanol, at a temperature between room temperature and that of the refluxing solvent and at a pressure preferably between atmospheric pressure and 10 atm. A thioether group can be oxidized to a sulfinyl or sulfonyl group by treatment with a suitable oxidising agent. For example, a thioether group can be oxidized to a sulfonyl group by treatment with m-chloroperbenzoic acid in a suitable solvent such as a halogenated hydrocarbon at a temperature preferably between 0° C. and room temperature. Moreover, an amino group can be converted to a group of formula (i) by treatment with phenyl chloroformate, subsequent reaction of the phenyl carbamate thus obtained with hydrazine and finally cyclisation of the resulting semicarbazide with formamidine or acetamidine in a suitable solvent such as dimethylformamide at a temperature between room temperature and that of the refluxing solvent. A nitrile group can be converted to a tetrazole group by treatment with a suitable azide such as sodium azide or ammonium azide (which may be prepared in situ from sodium azide and ammonium chloride) in a suitable solvent such as a polar solvent, for example dimethylformamide or N-methylpyrrolidone, at a temperature preferably between room temperature and that of the refluxing solvent. Another example of interconversion is the N-alkylation of a group of formula (i) or a tetrazole by treatment with the corresponding alkyl halide in the presence of a base such as potassium or cesium carbonate in a suitable aprotic solvent such as dimethylformamide. A nitrile group can be hydrolized to a carbamoyl group by treatment with ammonium hydroxide in a suitable solvent such as tetrahydrofuran-water mixtures under reflux. A nitrile group can also be converted to an alkyl imidate group by bubbling HCl gas in an alcohol, such as methanol. An alkyl imidate group can also be converted to an amino(imino)methyl group by reaction with an amine using the corresponding alkanol as solvent. Moreover, a halogen atom, for example bromo or iodo, can be converted to a phenyl group by a coupling reaction between the corresponding haloderivative and a boronic acid or ester of formula $(RO)_2B$-phenyl (wherein R represents hydrogen or $C_1$–$C_4$ alkyl) in the presence of a palladium catalyst such as $Pd(OAc)_2$ or $Pd(PPh_3)_4$ in a suitable solvent such as dimethoxyethane at a temperature preferably between room temperature and that of the refluxing solvent. A halogen atom, for example a fluorine atom, can be converted into a $C_1$–$C_4$ alkoxy, $C_1$–$C_4$ haloalkoxy, phenoxy, —$SR_{10}$, triazole or imidazole group by treatment with an alkaline metal salt of the corresponding alcohol, thiol, triazole or imidazole, for example the sodium salt, in a suitable aprotic solvent such as N-methylpyrrolidone at a temperature between room temperature and that of the refluxing solvent; moreover, it can also be converted into an amine (—$NR_6R_7$, 1-pyrrolidine, morpholine, a group of formula (ii) or a group of formula (iii)) by treatment with the corresponding amine in a suitable aprotic solvent such as N-methylpyrrolidone at a temperature between room temperature and that of the refluxing solvent.

Furthermore, a compound of formula I wherein Y represents —SO— or —$SO_2$— can be prepared from the corresponding compound of formula I wherein Y is —S— by oxidation as described above in connection with group B.

As it will be apparent to those skilled in the art, these interconversion reactions can be carried out both on the final products of formula I or on any synthetic intermediate thereof.

Amines of formula II can be prepared as described in *J.Org.Chem*, 1995, 60, 3000–3012, EP 332387 or EP 617031.

Acids of formula III or derivatives thereof are commercially available, widely described in the literature or can be prepared by methods analogous to those known in the art. Thus, for example, 5-substituted 1-arylpyrazole-4-carboxylic acids can be prepared by reacting the corresponding arylhydrazine with the product obtained from reacting the corresponding ethyl acylacetate with dimethylformamide dimethylacetal, followed by alkaline hydrolysis (KOH/EtOH—$H_2O$), as described in *J. Heterocyclic Chem.* 1987, 24, 1669. 1-Arylpyrazole-4-carboxylic acids can be prepared by reacting the corresponding arylhydrazine with carbethoxymalonaldehyde, followed by alkaline hydrolysis, as described in *Gazz.Chim.Ital.*, 1946, 76, 56. 1-Aryl-5-aminopyrazole-4-carboxylic acids can be prepared by reacting ethyl ethoxymethylenecyanoacetate with the corresponding arylhydrazine, followed by hydrolysis under basic conditions, as described in *Helv.Chim.Acta*, 1959, 349. 2-Aryl-4-alkylthiazole-5-carboxylic acids can be prepared by reacting the corresponding thiobenzamide with methyl acylchloroacetate in ethanol followed by alkaline hydrolysis, as described in *Eur.J.Med.Chem.* 1976, 11, 567. 2-Arylthiazole-4-carboxylic acids can be prepared by reacting the corrsponding thiobenzamide with ethyl bromopyruvate in ethanol followed by alkaline hydrolysis. 1-Arylpyrrole-3-carboxylic acids are prepared by reacting the correpsonding aniline with 2,5-dimethoxy-3-tetrahydrofurancarboxaldehyde in acetic acid under reflux, followed by oxidation with silver nitrate, as described in *Org.Prep.Proced.Int.*, 1995, 27, 236. 5-Arylthiophene-2-carboxylic acids can be prepared by reacting the corresponding acetophenone, dimethylformamide and ethyl thioglycolate in the presence of $POCl_3$, followed by alkaline hydrolysis, as described in *Tetrahedron Lett.*, 1968, 1317. 5-Aryl-3-aminothiophene-2-carboxylic acids can be prepared by reacting the corresponding β-chlorocinnamonitrile with ethyl thioglycolate in the presence of a base, followed by alkaline hydrolysis, as described in *Synthesis*, 1984, 275. 5-Aryl-1,3,4-oxadiazole-2-carboxylic acids can be prepared by the general procedure described in *J. Prakt.Chem.* 1985, 327, 109. 3-Aryl-1,2,4-oxadiazole-5-carboxylic acids can be prepared by the general procedure described in *J. Med. Chem.* 1995, 38, 1355. 5-Aryl-1,2,4-oxadiazole-3-carboxylic acids can be prepared by the general procedure described in *Bull. Chem.Soc.Jpn.* 1985, 58, 2519. 3-Aryl-1,2,4-thiadiazole-5-carboxylic acids and 5-aryl-1,2,4-thiadiazole-3-carboxylic acids can be prepared by the general procedure described in *J. Org.Ciem.* 1977, 42, 1813.

The present invention further provides compositions that contain a compound of the present invention, together with an excipient and optionally other auxiliary agents, if necessary. The compounds of the present invention can be administered in different pharmaceutical preparations, the precise nature of which will depend, as it is well known, upon the chosen route of administration and the nature of the pathology to be treated.

Thus, solid compositions according to the present invention for oral administration include compressed tablets, dispersible powders, granules and capsules. In tablets, the active component is admixed with at least one inert diluent such as lactose, starch, mannitol, microcrystalline cellulose or calcium phosphate; granulating and disintegrating agents for example corn starch, gelatine, microcrystalline cellulose or polyvinylpyrrolidone; and lubricating agents for example magnesium stearate, stearic acid or talc. The tablets may be coated by known techniques to delay disintegration and absorption in the gastrointestinal tract and, thereby, provide a sustained action over a longer period. Gastric film-coated or enteric film-coated tablets can be made with sugar, gelatin, hydroxypropylcellulose, or acrylic resins. Tablets with a sustained action may also be obtained using an excipient which provides regressive osmosis, such as the galacturonic acid polymers. Formulations for oral use may also be presented as hard capsules of absorbable material, such as gelatin, wherein the active ingredient is mixed with an inert solid diluent and lubricating agents, or pasty materials, such as ethoxylated saturated glycerides. Soft gelatin capsules are also possible wherein the active ingredient is mixed with water or an oily medium, for example peanut oil, liquid paraffin or olive oil.

Dispersible powders and granules suitable for the preparation of a suspension by the addition of water provide the active ingredient in admixture with a dispersing or wetting agent; a suspending agent, such as sodium carboxymethylcellulose, methylcellulose, hydroxypropylmethylcellulose, sodium alginate, polyvinylpirrolidone, gum tragacanth, xantham gum, gum acacia, and one or more preservatives, such as methyl or n-propyl p-hydroxybenzoate. Additional excipients, for example sweetening, flavoring and coloring agents may also be present.

Liquid compositions for oral administration include emulsions, solutions, suspensions, syrups and elixirs containing commonly used inert diluents, such as distilled water, ethanol, sorbitol, glycerol, or propylene glycol. Aqueous solutions can also be prepared using β-cyclodextrins, such as hydroxypropyl-β-cyclodextrin. Such compositions may also comprise adjuvants such as wetting agents, suspending agents, sweetening, flavoring, perfuming, preserving agents and buffers.

Other compositions for oral administration include spray compositions, which may be prepared by known methods. The spray compositions will contain a suitable propellent.

Preparations for injection, according to the present invention, for parenteral administration include sterile aqueous or non-aqueous solutions, suspensions or emulsions, in a non-toxic parentally-acceptable diluent or solvent. Examples of aqueous solvents or suspending media are distilled water for injection, Ringer's solution, and isotonic sodium chloride solution. Aqueous solutions can also be prepared using β-cyclodextrins, such as hydroxypropyl-β-cyclodextrin. Examples of non-aqueous solvents or suspending media are propylene glycol, polyethylene glycol, vegetable oils such as olive oil, or alcohols such as ethanol. These compositions may also include adjuvants such as wetting, preserving, emulsifying and dispersing agents. They may be sterilized by one of the known methods or manufactured in the form of sterile solid compositions which can be dissolved in sterile water or some other sterile injectable medium immediately before use. When all of the components are sterile, the injectables will maintain the sterility if they are manufactured in sterile environment.

Preparations for vaginal administration according to the present invention include tablets, capsules, softgels, moulded pessaries, creams, foams and vaginal douches. Vaginal tablets provide the active component in admixture with lactose, microcrystalline cellulose, pregelatinized starch, polyvidone and magnesium stearate as typical excipients. Soft gelatin capsules (softgels) can be made dispersing the active ingredient in an oily medium, for example liquid paraffin, dimethylpolysiloxane 1000 or hydrogenated soybean oil. Moulded pessaries provide the active ingredient in admixture with a suitable synthetic or semisynthetic base (such as Suppocire® or Novata® types). Low viscosity saturated $C_8$ to $C_{12}$ fatty acid glycerides and colloidal silice are also added to improve incorporation and to prevent sedimentation of the active ingredient. Vaginal creams can be prepared as emulsions, with sufficient viscosity to retain their integrity and adhere to the vaginal cavity. Neutral fats, fatty acids, waxes, mineral oils and fatty acid esters can be used as the oily phase. Water, glycerine, sorbitol solution and polyethylene glycol are suitable excipients for the aqueous phase. Non-ionic emulsifying agents like polyethylene glycol ethers may also be used, and such compositions may also contain preserving, buffering and stiffening agents.

Foaming systems can be made using a foamer (dispenser) that is able to transform a solution into a foam. Such systems may include cosolvents, buffers, preservatives, foam stabilizers and perfumes in an aqueous vehicle. Vaginal douches may contain cosolvents, preservatives, buffers and perfuming agents in a surfactant rich aqueous solution.

A compound of the invention may also administered in the form of suppositories for rectal administration of the drug, or as creams, ointments, pastes, lotions, gels, sprays, foams, aerosols, solutions, suspensions or powders for topical use. Such compositions are prepared following conventional procedures well known to those skilled in the art.

A compound of the invention may also be administered as a hair or body shampoo. These formulations may be prepared using suitable ionic and/or amphoteric surface-active agents such as sodium laureth sulfate, triethanolamine laureth sulfate, cocoamidopropyl betaine; thickening agents for example cocamide DEA, carbomer, sodium chloride and polyethylene glycol 6000 distearate; and optionally, emolient and superfatting agents, buffers, and preserving and perfuming agents.

The dosage and frequency of dose may vary depending upon the nature and severity of the fungal disease, symptoms, age and body weight of the patient, as well as upon the route of administration. In general, the compounds of the invention will be administered orally or parenterally at a dosage ranging from 0.01 mg/Kg/day to 100 mg/Kg/day, which can be administered as a single dose or as divided doses.

Following are some representative preparations for tablets, capsules, syrups, aerosols and injectables. They can be prepared following standard procedures and they are useful in the treatment of fungal diseases.

| Tablets | |
|---|---:|
| Compound of formula I | 100 mg |
| Dibasic calcium phosphate | 125 mg |
| Sodium starch glycolate | 10 mg |
| Talc | 12.5 mg |
| Magnesium stearate | 2.5 mg |
| | 250.0 mg |
| Hard gelatin capsules | |
| Compound of formula I | 100 mg |
| Lactose | 197 mg |
| Magnesium stearate | 3 mg |
| | 300 mg |
| Syrup | |
| Compound of formula I | 0.4 g |
| Sucrose | 45 g |
| Flavouring agent | 0.2 g |
| Sweetening agent | 0.1 g |
| Water to | 100 mL |
| Aerosol | |
| Compound of formla I | 4 g |
| Flavouring agent | 0.2 g |
| Propylene glycol to | 100 mL |
| Suitable propellent to | 1 unit |
| Injectable preparation 1 | |
| Compound of formula I | 100 mg |
| Benzylic alcohol | 0.05 mL |
| Propylene glycol | 1 mL |
| Water to | 5 mL |
| Injectable preparation 2 | |
| Compound of formula I | 100 mg |

| | |
|---|---|
| Hydroxypropyl-β-cydodextrin | 1 g |
| Sodium chloride | 90 mg |
| Water to | 10 mL |

The following examples illustrate, but do not limit, the scope of the present invention:

REFERENCE EXAMPLE 1

1-(4-Chlorophenyl)-1H-pyrazole-4-carboxylic acid (a) A solution of carbethoxymalonaldehyde (0.8 g, 5.55 mmol; obtained according to Panizzi, L. *Gazz.Chim.Ital.*, 1946, 76, 56) in ethanol (25 mL) was treated with 4-chlorophenylhydrazine hydrochloride (1.0 g, 5.55 mmol) at reflux for 5 h. The resulting reddish mixture was concentrated to an oil that was purified by flash chromatography to give ethyl 1-(4-chlorophenyl)-1H-pyrazole-4-carboxylate (0.68 g, 49%) as a white solid: mp 127°–128° C.; $^1$H NMR (80 MHz, CDCl$_3$) δ (TMS) 8.37 (s, 1H, pyrazole), 8.09 (s, 1H, pyrazole), 7.67 (dt, $J_t$=2, $J_d$=9, 2H, arom), 7.44 (dt,$J_t$=2, $J_d$=9, 2H, arom), 4.35 (q, J=7, 2H, OCH$_2$), 1.38 (t, J=7, 3H, OCH$_2$CH$_3$). Analysis calculated for C$_{12}$H$_{11}$ClN$_2$O$_2$: C 57.50; H 4.42; N 11.17. Found: C 57.49; H 4.46; N 11.16.

(b) A solution of the above product (0.44 g, 1.75 mmol) in EtOH (25 mL) and H$_2$O (4 mL) was treated with KOH (85%, 0.81 g, 13 mmol) at reflux for 4 h. Then, the reaction mixture was concentrated, partitioned between H$_2$O and CHCl$_3$ and the organic phase was discarded. The aqueous phase was acidified to pH 1 with 6N HCl and the precipitate formed was filtered, washed with water and dried to give the title compound as a white solid (0.32 g, 82%): mp 234°–235° C.; $^1$H NMR (80 MHz, CDCl$_3$) δ (TMS) 8.44 (s, 1H, pyrazole), 8.16 (s, 1H, pyrazole), 7.68 (dt,$J_t$=2,$J_d$=9, 2H, arom), 7.45 (dt,$J_t$=2,$J_d$=9, 2H, arom). Analysis calculated for C$_{10}$H$_7$ClN$_2$O$_2$: C 53.95; H 3.17; N 12.58. Found: C 53.31; H 3.30; N 12.60.

REFERENCE EXAMPLE 2

1-(4-Chlorophenyl)-5-methyl-1H-pyrazole-4-carboxylic acid

The preparation of the following 5-substituted 1-aryl-1H-pyrazole-4-carboxylic acids was carried out according to the general procedure described in Menozzi, G. et al. *J.Heterocyclic Chem.* 1987, 24, 1669. The following example illustrates this procedure:

(a) To a solution of ethyl acetylacetate (6 g, 46 mmol) in benzene (100 mL) was slowly added a solution of dimethylformamide dimethylacetal (8.2 g, 69 mmol) in benzene (100 mL) at 25° C. After the addition was complete, the reddish mixture was heated at reflux for 1 h and then evaporated to dryness to give ethyl 2-dimethylaminomethylene-3-oxobutanoate (8.66 g) as a reddish oil. This product (3.25 g, 17 mmol) was allowed to react with 4-chlorophenylhydrazine hydrochloride (3.14 g, 17 mmol) in EtOH (50 mL) at reflux for 8 h. The mixture was evaporated to dryness and the product was isolated by flash chromatography to give ethyl 1-(4-chlorophenyl)-5-methyl-1H-pyrazole-4-carboxylate as a white solid (2.07 g, 46%): mp 55°–56° C.; $^1$H NMR (80 MHz, CDCl$_3$) δ (TMS) 8.02 (s, 1H, pyrazole), 7.50 (d, J=9, 2H, arom), 7.34 (d, J=9, 2H, arom), 4.33 (q, J=7, 2H, OCH$_2$), 2.56 (s, 3H, Me-pyrazole), 1.37 (t, J=7, 3H, OCH$_2$CH$_3$). Analysis calculated for C$_{13}$H$_{13}$ClN$_2$O$_2$: C 58.99; H 4.95; N 10.58. Found: C 59.03; H 5.06; N 10.58.

(b) A solution of the product obtained in section (a) (1.91 g, 7.21 mmol) in EtOH (50 mL) and H$_2$O (10 mL) was treated with KOH (85%, 3.35 g, 50 mmol) at 60° C. for 20 h. Then, the reaction mixture was concentrated and partitioned between H$_2$O and CHCl$_3$. The organic phase was discarded and the aqueous phase was acidified to pH 1 with 3N HCl. The precipitate formed was filtered, washed with water and dried to give the title compound as a white solid (1.42 g, 83%): mp 195°–198° C.; $^1$H NMR (80 MHz, CDCl$_3$) δ (TMS) 8.39 (s, 1H, pyrazole), 7.50 (d, J=9, 2H, arom), 7.34 (d, J=9, 2H, arom), 2.59 (s, 3H, Me-pyrazole). Analysis calculated for C$_{11}$H$_9$ClN$_2$O$_2$: C 55.83; H 3.83; N 11.84. Found: C 56.10; H 3.82; N 11.54.

REFERENCE EXAMPLE 3

1-(4-Chlorophenyl)-5-isopropyl-1H-pyrazole-4-carboxylic acid (a) Following a similar procedure to that described in section a of reference example 2 ethyl 1-(4-chlorophenyl)-5-isopropyl-1H-pyrazole-4-carboxylate was obtained as a white solid: mp 86°–87° C.; 1H NMR (80 MHz, CDCl$_3$) δ (TMS) 8.01 (s, 1H, pyrazole), 7.48 (dt,$J_t$=2,$J_d$=9, 2H, arom), 7.28 (dt,$J_t$=2,$J_d$=9, 2H, arom), 4.33 (q, J=7, 2H, OCH$_2$), 3.28 (quint, J=7, 1H, Me$_2$CH), 1.38 (t, J=7, 3H, OCH$_2$CH$_3$), 1.35 (d, J=7, 6H, Me$_2$CH). Analysis calculated for C$_{15}$H$_{17}$ClN$_2$O$_2$: C 61.54; H 5.85; N 9.57. Found: C 61.23; H 5.94; N 9.42.

(b) Following a similar procedure to that described in section b of reference example 2 the title compound was obtained as a white solid: mp 211°–212° C.; $^1$H NMR (80 MHz, CDCl$_3$) δ (TMS) 8.11 (s, 1H, pyrazole), 7.48 (dt,$J_t$=2,$J_d$=9, 2H, arom), 7.30 (dt,$J_t$=2,$J_d$=9, 2H, arom), 3.29 (quint, J=7,1H, Me$_2$CH), 1.37 (t,J=7, 6H, Me$_2$CH). Analysis calculated for C$_{13}$H$_{13}$ClN$_2$O$_2$: C 58.99; H 4.95; N 10.58. Found: C 59.23; H 4.93; N 10.47.

REFERENCE EXAMPLE 4

5-tertButyl-1-(4-chlorophenyl)-1H-pyrazole-4-carboxylic acid (a) Following a similar procedure to that described in section a of reference example 2 ethyl 5-tertbutyl-1-(4-chlorophenyl)-1H-pyrazole-4-carboxylate was obtained as a white solid: mp 104°–105° C.; $^1$H NMR (80 MHz, CDCl$_3$) δ (TMS) 7.96 (s, 1H, pyrazole), 7.43 (dt,$J_t$=2,$J_d$=9, 2H, arom), 7.24 (dt,$J_t$=2,$J_d$=9, 2H, arom), 4.31 (q, J=7, 2H, OCH$_2$), 1.37 (t, J=7, 3H, OCH$_2$CH$_3$), 1.31 (s, 9H, Me$_3$C). Analysis calculated for C$_{16}$H$_{19}$ClN$_2$O$_2$: C 62.64; H 6.24; N 9.13. Found: C 62.67; H 6.28; N 9.12.

(b) Following the procedure described in section b of reference example 2 the title compound was obtained as a white solid: $^1$H NMR (80 MHz, CDCl$_3$) δ (TMS) 8.09 (s, 1H, pyrazole), 7.45 (dt,$J_t$=2,$J_d$=9, 2H, arom), 7.26 (dt,$J_t$=2, $J_d$=9, 2H, arom), 1.34 (s, 9H, Me$_3$C). Analysis calculated for C$_{14}$H$_{15}$ClN$_2$O$_2$: C 60.33; H 5.42; N 10.05. Found: C 60.41; H 5.41; N 10.12.

REFERENCE EXAMPLE 5

1-(4-Chlorophenyl)-5-cyclopropyl-1H-pyrazole-4-carboxylic acid (a) Following a similar procedure to that described in section a of reference example 2 ethyl 1-(4-chlorophenyl)-5-cyclopropyl-1H-pyrazole-4-carboxylate was obtained as a white solid: mp 64°–65° C.; 1H NMR (80 MHz, CDCl$_3$) δ

(TMS) 8.00 (s, 1H, pyrazole), 7.46 (s, 4H, arom), 4.33 (q, J=7, 2H, OCH$_2$), 2.2–1.8 (m, 1H, c-prop), 1.37 (t, J=7, 3H, OCH$_2$CH$_3$), 1.3–0.8 (m, 2H, c-prop), 0.8–0.5 (m, 2H, c-prop). Analysis calculated for C$_{15}$H$_{15}$ClN$_2$O$_2$: C 61.97; H 5.20; N 9.63. Found: C 61.64; H 5.26; N 9.65.

(b) Following the procedure described in section b of reference example 2 the title compound was obtained as a white solid: mp 186°–187° C.; $^1$H NMR (80 MHz, CDCl$_3$) δ (TMS) 8.09 (s, 1H, pyrazole), 7.46 (s, 4H, arom), 2.2–1.8 (m, 1H, c-prop), 1.3–0.8 (m, 2H, c-prop), 0.8–0.5 (m, 2H, c-prop). Analysis calculated for C$_{13}$H$_{11}$ClN$_2$O$_2$: C 59.44; H 4.22; N 10.66. Found: C 59.37; H 4.17; N 10.46.

REFERENCE EXAMPLE 6

5-Methyl-1-(4-trifluoromethylphenyl)-1H-pyrazole-4-carboxylic acid (a) Following a similar procedure to that described in section a of reference example 2 ethyl 5-methyl-1-(4-trifluoromethylphenyl)-1H-pyrazole-4-carboxylate was obtained as a white solid: mp 60°–61° C.; $^1$H NMR (80 MHz, CDCl$_3$) δ (TMS) 8.05 (s, 1H, pyrazole), 7.79 (d, J=9, 2H, arom), 7.58 (d, J=9, 2H, arom), 4.33 (q, J=7, 2H, OCH$_2$), 2.62 (s, 3H, Me-pyrazole), 1.38 (t, J=7, 3H, OCH$_2$CH$_3$). Analysis calculated for C$_{14}$H$_{13}$F$_3$N$_2$O$_2$: C 56.38; H 4.39; N 9.39. Found: C 56.34; H 4.36; N 9.32.

(b) Following the procedure described in section b of reference example 2 the title compound was obtained as a white solid: mp 186°–187° C.; $^1$H NMR (80 MHz, CDCl$_3$) δ (TMS) 8.14 (s, 1H, pyrazole), 7.80 (d, J=9, 2H, arom), 7.60 (d, J=9, 2H, arom), 2.64 (s, 3H, Me-pyrazole). Analysis calculated for C$_{12}$H$_9$F$_3$N$_2$O$_2$: C 53.34; H 3.36; N 10.37. Found: C 53.68; H 3.38; N 10.22.

REFERENCE EXAMPLE 7

1-(4-Bromophenyl)-5-methyl-1H-pyrazole-4-carboxylic acid (a) Following a similar procedure to that described in section a of reference example 2 ethyl 1-(4-bromophenyl)-5-methyl-1H-pyrazole-4-carboxylate was obtained as a thick oil: $^1$H NMR (80 MHz, CDCl$_3$) δ (TMS) 8.02 (s, 1H, pyrazole), 7.63 (dt, J$_t$=2, J$_d$=9, 2H, arom), 7.31 (dt, J$_t$=2, J$_d$=9, 2H, arom), 4.33 (q, J=7, 2H, OCH$_2$), 2.56 (s, 3H, Me-pyrazole), 1.37 (t, J=7, 3H, OCH$_2$CH$_3$). Analysis calculated for C$_{13}$H$_{13}$BrN$_2$O$_2$: C 50.51; H 4.24; N 9.06. Found: C 50.34; H 4.57; N 8.93.

(b) Following the procedure described in section b of reference example 2 the title compound was obtained as a white solid: mp 213°–214° C.; 1H NMR (80 MHz, CDCl$_3$) δ (TMS) 8.10 (s, 1H, pyrazole), 7.65 (dt, J$_t$=1.5, J$_d$=9, 2H, arom), 7.31 (dt, J$_t$=1.5, J$_d$=9, 2H, arom), 2.59 (s, 3H, Me-pyrazole). Analysis calculated for C$_{11}$H$_9$BrN$_2$O$_2$: C 47.00; H 3.23; N 9.97. Found: C 47.01; H 3.21; N 9.99.

REFERENCE EXAMPLE 8

5-Trifluoromethyl-1-(4-trifluoromethylphenyl)-1H-pyrazole-4-carboxylic acid (a) Following a similar procedure to that described in section a of reference example 2 ethyl 5-trifluoromethyl-1-(4-trifluoromethylphenyl)-1H-pyrazole-4-carboxylate was obtained as a white solid: mp 45°–46° C.; $^1$H NMR (80 MHz, CDCl$_3$) δ (TMS) 8.14 (s, 1H, pyrazole), 7.90 (d, J=9, 2H, arom), 7.56 (d, J=9, 2H, arom), 4.38 (q, J=7, 2H, OCH$_2$), 1.39 (t, J=7, 3H, OCH$_2$CH$_3$). Analysis calculated for C$_{14}$H$_{10}$F$_6$N$_2$O$_2$: C 47.74; H 2.86; N 7.95. Found: C 47.89; H 2.92; N 7.95.

(b) Following the procedure described in section b of reference example 2 the title compound was obtained as a white solid: mp 157°–158° C.; $^1$H NMR (80 MHz, CDCl$_3$) δ (TMS) 8.23 (s, 1H, pyrazole), 7.82 (d, J=9, 2H, arom), 7.58 (d, J=9, 2H, arom). Analysis calculated for C$_{12}$H$_6$F$_6$N$_2$O$_2$: C 44.46 H 1.87; N 8.64. Found: C 44.76; H 1.82; N 8.50.

REFERENCE EXAMPLE 9

1-(3,5-Dichlorophenyl)-5-methyl-1H-pyrazole-4-carboxylic acid (a) Following a similar procedure to that described in section a of reference example 2 ethyl 1-(3,5-dichlorophenyl)-5-methyl-1H-pyrazole-4-carboxylate was obtained as a pale yellow solid: mp 85°–86° C.; $^1$H NMR (80 MHz, CDCl$_3$) δ (TMS) 8.02 (s, 1H, pyrazole), 7.5–7.3 (m, 3H, arom), 4.34 (q, J=7, 2H, OCH$_2$), 2.61 (s, 3H, Me-pyrazole), 1.37 (t, J=7, 3H, OCH$_2$CH$_3$). Analysis calculated for C$_{13}$H$_{12}$Cl$_2$N$_2$O$_2$: C 52.19; H 4.04; N 9.36. Found: C 52.20; H 3.99; N 9.97.

(b) Following the procedure described in section b of reference example 2 the title compound was obtained as a white solid: mp 229°–230° C.; $^1$H NMR (300 MHz, CDCl$_3$) δ (TMS) 7.98 (s, 1H, pyrazole), 7.40 (t, J=1.8, 1H, arom), 7.33 (t, J=1.8, 2H, arom), 2.54 (s, 3H, Me-pyrazole). Analysis calculated for C$_{11}$H$_8$Cl$_2$N$_2$O$_2$: C 48.73; H 2.97; N 10.33. Found: C 48.92; H 2.89; N 10.40.

REFERENCE EXAMPLE 10

1-(2,6-Dichlorophenyl)-5-methyl-1H-pyrazole-4-carboxylic acid (a) Following a similar procedure to that described in section a of reference example 2 ethyl 1-(2,6-dichlorophenyl)-5-methyl-1H-pyrazole-4-carboxylate was obtained as colourless oil: $^1$H NMR (80 MHz, CDCl$_3$) δ (TMS) 8.12 (s, 1H, pyrazole), 7.6–7.4 (m, 3H, arom), 4.34 (q, J=7, 2H, OCH$_2$), 2.36 (s, 3H, Me-pyrazole), 1.38 (t, J=7, 3H, OCH$_2$CH$_3$). Analysis calculated for C$_{13}$H$_{12}$Cl$_2$N$_2$O$_2$: C 52.19; H 4.04; N 9.36. Found: C 52.56; H 3.81; N 9.14.

(b) Following the procedure described in section b of reference example 2 the title compound was obtained as a white solid: mp 180°–182° C.; $^1$H NMR (300 MHz, CDCl$_3$) δ (TMS) 8.20 (s, 1H, pyrazole), 7.6–7.4 (m, 3H, arom), 2.40 (s, 3H, Me-pyrazole). Analysis calculated for C$_{11}$H$_8$Cl$_2$N$_2$O$_2$: C 48.73; H 2.97; N 10.33. Found: C 48.82; H 2.90; N 10.20.

REFERENCE EXAMPLE 11

1-(2-Chlorophenyl)-5-methyl-1H-pyrazole-4-carboxylic acid (a) Following a similar procedure to that described in section a of reference example 2 ethyl 1-(2-chlorophenyl)-5-methyl-1H-pyrazole-4-carboxylate was obtained as a colourless oil: $^1$H NMR (300 MHz, CDCl$_3$) δ (TMS) 8.05 (s, 1H, pyrazole), 7.6–7.4 (m, 4H, arom), 4.32 (q, J=7, 2H, OCH$_2$), 2.39 (s, 3H, Me-pyrazole), 1.37 (t, J=7, 3H, OCH$_2$CH$_3$). Analysis calculated for C$_{13}$H$_{13}$ClN$_2$O$_2$: C 58.99; H 4.95; N 10.58. Found: C 59.20; H 4.91; N 10.38.

(b) Following the procedure described in section b of reference example 2 the title compound was obtained as a white solid: mp 150°–151° C.; $^1$H NMR (300 MHz, CDCl$_3$) δ (TMS) 8.14 (s, 1H, pyrazole), 7.6–7.4 (m, 4H, arom), 2.42 (s, 3H, Me-pyrazole). Analysis calculated for C$_{11}$H$_9$ClN$_2$O$_2$: C 55.83; H 3.83; N 11.84. Found: C 56.03; H 3.91; N 11.93.

REFERENCE EXAMPLE 12

1-(4-Chlorophenyl)-3,5-dimethyl-1H-pyrazole-4-carboxylic acid (a) Following a similar procedure to that described in section a of reference example 2 but reacting ethyl diacetylacetate with 4-chlorophenylhydrazine hydrochloride, ethyl 1-(4-chlorophenyl)-3,5-dimethyl-1H-pyrazole-4-carboxylate was directly obtained as a white solid: mp 79°–80° C.; $^1$H NMR (80 MHz, CDCl$_3$) δ (TMS) 7.47 (d, J=9, 2H, arom), 7.32 (d, J=9, 2H, arom), 4.32 (q, J=7, 2H, OCH$_2$), 2.51 (s, 3H, Me-pyrazole), 2.49 (s, 3H, Me-pyrazole), 1.38 (t, J=7, 3H, OCH$_2$CH$_3$). Analysis calculated for C$_{14}$H$_{15}$ClN$_2$O$_2$: C 60.33; H 5.42; N 10.05. Found: C 60.44; H 5.48; N 10.29.

(b) Following the procedure described in section b of reference example 2 the title compound was obtained as a white solid: mp 220°–223° C.; $^1$H NMR (80 MHz, CDCl$_3$) δ (TMS) 7.48 (d, J=9, 2H, arom), 7.34 (d, J=9, 2H, arom), 2.55 (s, 3H, Me-pyrazole), 2.52 (s, 3H, Me-pyrazole). Analysis calculated for C$_{12}$H$_{11}$ClN$_2$O$_2$: C 57.50; H 4.42; N 11.17. Found: C 57.60; H 4.43; N 11.19.

REFERENCE EXAMPLE 13

5-Amino-1-(4-chlorophenyl)-1H-pyrazole-4-carboxylic acid (a) A solution of ethyl ethoxymethylenecyanoacetate (3 g, 17.7 mmol) and 4-chlorophenylhydrazine hydrochloride (3.33 g, 18.6 mmol) in ethanol (60 mL) was refluxed for 2 days, following the procedure described in Schmidt, P. et al. Helv.Chim.Acta, 1959, 349. The reaction mixture was then allowed to cool to room temperature, whereupon a precipitate was formed. Cold CHCl$_3$ was added, the precipitate was filtered and washed with more CHCl$_3$. The filtrate and the washings were evaporated to dryness, precipitated with ether, filtered and dried to give ethyl 5-amino-1-(4-chlorophenyl)-1H-pyrazole-4-carboxylate (2.25 g, 48%) as a white solid: mp 150°–156° C.; 1H NMR (80 MHz, CDCl$_3$) δ (TMS) 7.77 (s, 1H, pyrazole), 7.48 (s, 4H, arom), 4.30 (q, J=7, 2H, OCH$_2$), 1.36 (t, J=7, 3H, OCH$_2$CH$_3$). Analysis calculated for C$_{12}$H$_{12}$ClN$_3$O$_2$: C 54.25; H 4.55; N 15.81. Found: C 54.77; H 4.49; N 15.65.

(b) Following the procedure described in section b of reference example 2 the title compound was obtained as a white solid: mp 169°–171° C.; $^1$H NMR (80 MHz, CDCl$_3$+ MeOH—d$_4$) δ (TMS) 7.78 (s, 1H, pyrazole), 7.50 (s, 4H, arom), 4.25 (br s, NH$_2$, OH). Analysis calculated for C$_{10}$H$_8$ClN$_3$O$_2$: C 50.54; H 3.39; N 17.68. Found: C 50.54; H 3.39; N 17.44.

REFERENCE EXAMPLE 14

5-Amino-1-(4-trifluoromethylphenyl)-1H-pyrazole-4-carboxylic acid (a) Following the procedure described in the reference example 13 ethyl 5-amino-1-(4-trifluoromethylphenyl)-1H-pyrazole-4-carboxylate was obtained as an amorphous white solid: $^1$H NMR (80 MHz, CDCl$_3$) δ (TMS) 7.76 (s, 1H, pyrazole), 7.90 (d, J=9, 2H, arom), 7.56 (d, J=9, 2H, arom), 4.31 (q, J=7, 2H, OCH$_2$), 1.35 (t, J=7, 3H, OCH$_2$CH$_3$). Analysis calculated for C$_{13}$H$_{12}$F$_3$N$_3$O$_2$: C 52.18; H 4.04; N 14.04. Found: C 52.13; H 4.22; N 14.02

(b) Following the procedure described in section b of reference example 2 the title compound was obtained as a white solid: mp 169°–171° C.; $^1$H NMR (80 MHz, CDCl$_3$+ MeOH—d$_4$) δ (TMS) 7.78 (s, 1H, pyrazole), 7.90 (d, J=9, 2H, arom), 7.56 (d, J=9, 2H, arom), 4.32 (s, NH$_2$, OH). Analysis calculated for C$_{11}$H$_8$F$_3$N$_3$O$_2$: C 48.72; H 2.97; N 15.49. Found: C 48.52; H 3.18; N 15.28.

REFERENCE EXAMPLE 15

5-Methyl-1-(3-trifluoromethylphenyl)-1H-pyrazole-4-carboxylic acid (a) Following a similar procedure to that described in section a or reference example 2 ethyl 5-methyl-1-(3-trifluoromethylphenyl)-1H-pyrazole-4-carboxylate was obtained as a colourless oil: $^1$H NMR (80 MHz, CDCl$_3$) δ (TMS) 8.05 (s, 1H, pyrazole), 7.8–7.5 (m, 4H, arom), 4.34 (q, J=7, 2H, OCH$_2$), 2.61 (s, 3H, Me-pyrazole), 1.38 (t, J=7, 3H, OCH$_2$CH$_3$). Analysis calculated for C$_{14}$H$_{13}$F$_3$N$_2$O$_2$: C 56.38; H 4.39; N 9.39. Found: C 56.42; H 4.67; N 9.13.

(b) Following the procedure described in section b of reference example 2 the title compound was obtained as a white solid: mp 122°–123° C.; $^1$H NMR (300 MHz, CDCl$_3$) δ (TMS) 8.20 (s, 1H, pyrazole), 7.8–7.7 (m, 4H, arom), 2.69 (s, 3H, Me-pyrazole). Analysis calculated for Cl$_2$H$_9$F$_3$N$_2$O$_2$: C 53.34; H 3.36; N 10.37. Found: C 53.36; H 3.50; N 10.44.

REFERENCE EXAMPLE 16

5-Methyl-1-(4-trifluoromethoxyphenyl)-1H-pyrazole-4-carboxylic acid (a) Following a similar procedure to that described in section a of reference example 2 ethyl 5-methyl-1-(4-trifluoromethoxyphenyl)-1H-pyrazole-4-carboxylate was obtained as a colourless oil: $^1$H NMR (80 MHz, CDCl$_3$) δ (TMS) 8.02 (s, 1H, pyrazole), 7.52 (d, J=9, 2H, arom), 7.32 (d, J=9, 2H, arom), 4.33 (q, J=7, 2H, OCH$_2$), 2.57 (s, 3H, Me-pyrazole), 1.38 (t, J=7, 3H, OCH$_2$CH$_3$). Analysis calculated for C$_{14}$H$_{13}$F$_3$N$_2$O$_3$: C 53.51; H 4.17; N 8.91. Found: C 53.43; H 4.28; N 8.55.

(b) Following the procedure described in section b of reference example 2 the title compound was obtained as a white solid: mp 176°–178° C.; $^1$H NMR (300 MHz, CDCl$_3$) δ (TMS) 8.46 (s, 1H, pyrazole), 7.55 (dt, J$_t$=2.8, J$_d$=8.8, 2H, arom), 7.43 (d, J=8.8, 2H, arom), 2.67 (s, 3H, Me-pyrazole). Analysis calculated for C$_{12}$H$_9$F$_3$N$_2$O$_3$: C 50.36; H 3.17; N 9.79. Found: C 50.52; H 3.13; N 9.76.

REFERENCE EXAMPLE 17

1-(4-Methoxyphenyl)-5-methyl-1H-pyrazole-4-carboxylic acid (a) Following a similar procedure to that described in section a of reference example 2 ethyl 1-(4-methoxyphenyl)-5-methyl-1H-pyrazole-4-carboxylate was obtained as a colourless oil: $^1$H NMR (300 MHz, CDCl$_3$) δ (TMS) 7.99 (s, 1H, pyrazole), 7.31 (d, J=9, 2H, arom), 6.99 (d, J=9, 2H, arom), 4.31 (q, J=7, 2H, OCH$_2$), 3.85 (s, 3H, OMe), 2.51 (s, 3H, Me-pyrazole), 1.34 (t, J=7, 3H, OCH$_2$CH$_3$). Analysis calculated for C$_{14}$H$_{16}$N$_2$O$_3$: C 64.60; H 6.20; N 10.76. Found: C 64.89; H 6.41; N 10.51.

(b) Following the procedure described in section b of reference example 2 the title compound was obtained as a white solid: mp 212°–213° C.; $^1$H NMR (300 MHz, CDCl$_3$) δ (TMS) 8.08 (s, 1H, pyrazole), 7.33 (d, J=8.8, 2H, arom), 7.01 (d, J=8.8, 2H, arom), 3.87 (s, 3H, OMe), 2.54 (s, 3H, Me-pyrazole). Analysis calculated for C$_{12}$H$_{12}$N$_2$O$_3$: C 62.06; H 5.21; N 12.06. Found: C 62.23; H 2.13; N 12.06.

REFERENCE EXAMPLE 18

2-(4-Chlorophenyl)thiazole-5-carboxylic acid (a) A solution of ethyl formylchloroacetate (1.45 g, 9.6 mmol; obtained according to Panizzi, L. Gazz. Chim.Ital., 1946, 76, 56) and 4-chlorothiobenzamide (1.76 g, 9.6 mmol) in EtOH (50 mL) was refluxed for 48 h. The reaction mixture was then cooled to –20° C. and the solid formed was filtered and dried to give ethyl 2-(4-chlorophenyl)thiazole-5-carboxylate (0.59 g, 23%): mp 144°–145° C.; $^1$H NMR (300 MHz, CDCl$_3$) δ (TMS) 8.40 (s, 1H, thiazole), 7.92 (dt, J$_t$=1.8, J$_d$=8.6, 2H, arom), 7.44 (dt, J$_t$=1.8, J$_d$=8.6, 2H, arom), 4.39 (q, J=7, 2H, OCH$_2$), 1.40 (t, J=7, 3H, OCH$_2$CH$_3$). Analysis calculated for C$_{12}$H$_{10}$ClNO$_2$S: C 53.84; H 3.76; N 5.23; S 11.97. Found: C 54.22; H 3.52; N 5.25; S 11.46.

(b) Following the hydrolysis procedure described in section b of reference example 2 the title compound was obtained as a white solid: mp 233°–234° C.; $^1$H NMR (300 MHz, CDCl$_3$+MeOH—d$_4$) δ (TMS) 8.31 (s, 1H, thiazole), 7.83 (dt, J$_t$=1.8, J$_d$=8.8, 2H, arom), 7.37 (dt, J$_t$=1.8, J$_d$=8.8, 2H, arom). Analysis calculated for C$_{10}$H$_6$ClNO$_2$S: C 50.11; H 2.52; N 5.84; S 13.38. Found: C 49.37; H 2.41; N 5.54; S 11.90.

REFERENCE EXAMPLE 19

4-Methyl-2-phenylthiazole-5-carboxylic acid (a) A solution of methyl 2-chloroacetoacetate (1.86 g, 12.4 mmol) and thiobenzamide (1.7 g, 12.4 mmol) in EtOH (50 mL) was refluxed for 18 h. The mixture was evaporated to dryness and the resulting oil was purified by flash chromatography to give methyl 4-methyl-2-phenylthiazole-5-carboxylate (1.21 g, 42%) as a colourless oil: $^1$H NMR (300 MHz, CDCl$_3$) δ (TMS) 8.0–7.9 (m, 2H, arom), 7.5–7.4 (m, 3H, arom), 3.87 (s, 3H, OMe), 2.76 (s, 3H, Me-thiazole). Analysis calculated for C$_{12}$H$_{11}$NO$_2$S: C 61.78; H 4.75; N 6.00; S 13.74. Found: C 61.56; H 4.71; N 5.82; S 14.61.

(b) Following the hydrolysis procedure described in section b of reference example 2 but using MeOH as solvent and heating at 80° C. for 4 h the title compound was obtained as a white solid: mp 215°–218° C,; $^1$H NMR (300 MHz, CDCl$_3$+MeOH—d$_4$) δ (TMS) 7.9–7.8 (m, 2H, arom), 7.4–7.3 (m, 3H, arom), 2.66 (s, 3H, Me-thiazole). Analysis calculated for C$_{11}$H$_9$NO$_2$S: C 60.26 H 4.14; N 6.39; S 14.62. Found: C 60.37; H 4.07; N 6.14; S 14.91.

REFERENCE EXAMPLE 20

2-(4-Chlorophenyl)-4-methylthiazole-5-carboxylic acid (a) Following the procedure described in section a of reference example 19 methyl 2-(4-chlorophenyl)-4-methylthiazole-5-carboxylate was obtained as a white solid: mp 132°–133° C.; $^1$H NMR (80 MHz, CDCl$_3$) δ (TMS) 7.89 (dt, J$_t$=1.8, J$_d$=8.8, 2H, arom), 7.40 (dt, J$_t$=1.8, J$_d$=8.8, 2H, arom), 3.89 (s, 3H, OMe), 2.77 (s, 3H, Me-thiazole). Analysis calculated for C$_{12}$H$_{10}$ClNO$_2$S: C 53.84; H 3.76; N 5.23; S 11.97. Found: C 54.09; H 3.78; N 5.10; S 12.27.

(b) Following the hydrolysis procedure described in section b of reference example 19 the title compound was obtained as a white solid: mp 256°–263° C.; $^1$H NMR (300 MHz, CDCl$_3$+MeOH—d$_4$) δ (TMS) 7.84 (dt, J$_t$=1.8, J$_d$=8.8, 2H, arom), 7.40 (dt, J$_t$=1.8, J$_d$=8.8, 2H, arom), 2.70 (s, 3H, Me-thiazole). Analysis calculated for C$_{11}$H$_8$ClNO$_2$S: C 52.08; H 3.18; N 5.52; S 12.64. Found: C ) 49.88; H 2.93; N 5.15; S 11.20.

REFERENCE EXAMPLE 21

2-(4-Bromophenyl)-4-methylthiazole-5-carboxylic acid (a) Following the procedure described in section a of reference example 19 methyl 2-(4-bromophenyl)-4-methylthiazole-5-carboxylate was obtained as a white solid: mp 144°–146° C.; $^1$H NMR (80 MHz, CDCl$_3$) δ (TMS) 7.84 (dt, J$_t$=2, J$_d$=8.6, 2H, arom), 7.57 (dt, J$_t$=2, J$_d$=8.6, 2H, arom), 3.89 (s, 3H, OMe), 2.77 (s, 3H, Me-thiazole). Analysis calculated for C$_{12}$H$_{10}$BrNO$_2$S: C 46.17; H 3.23; N 4.49; S 10.27. Found: C 45.95; H 3.27; N 4.52; S 10.34.

(b) Following the hydrolysis procedure described in section b of reference example 19 the title compound was obtained as a white solid: mp 227° C. (dec); $^1$H NMR (80 MHz, CDCl$_3$+MeOH—d$_4$) δ (TMS) 7.85 (dt, J$_t$=1.8, J$_d$=8.8, 2H, arom), 7.40 (dt, J$_t$=1.8, J$_d$=8.8, 2H, arom), 2.79 (s, 3H, Me-thiazole). Analysis calculated for C$_{11}$H$_8$BrNO$_2$S: C 44.31; H 2.70; N 4.70; S 10.75. Found: C 44.02; H 3.09; N 4.45; S 10.36.

REFERENCE EXAMPLE 22

4-Methyl-2-(4-trifluoromethoxyphenyl)thiazole-5-carboxylic acid (a) Following the procedure described in section a of reference example 19 methyl 4-methyl-2-(4-trifluoromethoxyphenyl)thiazole-5-carboxylate was obtained as a white solid: mp 76°–77° C.; $^1$H NMR (80 MHz, CDCl$_3$) δ (TMS) 8.00 (dt, J$_t$=2, J$_d$=8.8, 2H, arom), 7.30 (dt, J$_t$=2, J$_d$=8.8, 2H, arom), 3.90 (s, 3H, OMe), 2.78 (s, 3H, Me-thiazole). Analysis calculated for C$_{13}$H$_{10}$F$_3$NO$_3$S: C 49.21; H 3.18; N 4.41; S 10.10. Found: C 49.23; H 3.40; N 4.36; S 10.37.

(b) Following the hydrolysis procedure described in section b of reference example 19 the title compound was obtained as a white solid: mp 179°–181° C.; $^1$H NMR (80 MHz, CDCl$_3$) δ (TMS) 8.00 (dt, J$_t$=1.8, J$_d$=8.8, 2H, arom), 7.30 (dt, J$_t$=1.8, J$_d$=8.8, 2H, arom), 2.81 (s, 3H, Me-thiazole). Analysis calculated for C$_{12}$H$_8$F$_3$NO$_3$S: C 47.53; H 2.66; N 4.62; S 10.57. Found: C 47.59; H 2.68; N 4.62; S 10.26.

REFERENCE EXAMPLE 23

4-Methyl-2-[4-(2,2,3,3-tetrafluoropropoxy)phenyl]thiazole-5carboxylic acid (a) Following the procedure described in section a of reference example 19 methyl 4-methyl-2-[4-(2,2,3,3-tetrafluoropropoxy)phenyl]thiazole-5-carboxylate was obtained as a white solid: mp 102°–103° C.; $^1$H NMR (80 MHz, CDCl$_3$) δ (TMS) 7.95 (dt, J$_t$=2, J$_d$=8.8, 2H, arom), 7.00 (dt, J$_t$=2, J$_d$=8.8, 2H, arom), 6.06 (tt, J=4.6, J=53, 1H, CHF$_2$), 4.41 (tt, J=1.5, J=11.8, 2H, CH$_2$), 3.89 (s, 3H, OMe), 2.77 (s, 3H, Me-thiazole). Analysis calculated for C$_{15}$H$_{13}$F$_4$NO$_3$S: C 49.59; H 3.61; N 3.86; S 8.82. Found: C 49.76; H 3.73; N 3.89; S 8.66.

(b) Following the hydrolysis procedure described in section b of reference example 19 the title compound was obtained as a white solid: mp 167°–168° C.; $^1$H NMR (80 MHz, CDCl$_3$) δ (TMS) 7.95 (dt, J$_r$=1.8, J$_d$=8.8, 2H, arom), 7.00 (dt, J$_r$=1.8, J$_d$=8.8, 2H, arom), 6.05 (tt, J=4.6, J=53, 1H, CHF$_2$), 4.41 (tt, J=1.5, J=11.8, 2H, CH$_2$), 2.79 (s, 3H, Me-thiazole). Analysis calculated for C$_{14}$H$_{11}$F$_4$NO$_3$S: C 48.14; H 3.17; N 4.01; S 9.18. Found: C 48.20; H 3.19; N 3.71; S 8.72.

REFERENCE EXAMPLE 24

2-(4-Cyanophenyl)-4-methylthiazole-5-carboxylic acid (a) A suspension of methyl 2-chloroacetoacetate (30 g, 0.19 mol) and 4-cyanothiobenzamide (21.5 g, 0.13 mol) in MeOH (250 mL) was refluxed for 15 h. The reaction mixture was then cooled to 0° C., filtered after 20 h and washed with cooled (−20° C.) MeOH and with ether. The resulting off-white solid was dried to give methyl 2-(4-cyanophenyl)-4-methylthiazole-5-carboxylate (18.7 g, 55%). If desired, additional product may be recovered by flash chromatography of the washings: mp 186°–187° C.; $^1$H NMR (300 MHz, CDCl$_3$) δ (TMS) 8.07 (dt, J$_r$=1.6, J$_d$=8.3, 2H, arom), 7.74 (dt, J$_r$=1.6, J$_d$=8.3, 2H, arom), 3.91 (s, 3H, OMe), 2.79 (s, 3H, Me-thiazole). Analysis calculated for C$_{13}$H$_{10}$N$_2$O$_2$S: C 60.45; H 3.90; N 10.85; S 12.41. Found: C 60.31; H 3.80; N 10.53; S 11.79.

(b) The product obtained in section (a) (18.7 g, 72.4 mmol) was dissolved in a mixture of MeOH (0.6L) and THF (0.3L). Next, a solution of LiOH.H$_2$O (15.2 g, 0.36 mol) in 60 mL of water was slowly added and the resulting reddish mixture was stirred at 30° C. for 8 h. The mixture was then evaporated to dryness, water was added to the residue, then it was filtered through celite and was acidified with 3N HCl to pH 1.0–1.2, resulting in the appearance of an orange foamy material. This product, which was difficult to filter, was centrifuged, washed with cold water, centrifuged again and then dried to give the title compound as a yellowish solid (18 g, 100%): mp 235–250° C.; $^1$H NMR (300 MHz, CDCl$_3$) δ (TMS) 8.15 (dt, J$_r$=1.6, J$_d$=8.3, 2H, arom), 7.84 (dt, J$_r$=1.6, J$_d$=8.3, 2H, arom), 2.74 (s, 3H, Me-thiazole). Analysis calculated for C$_{12}$H$_8$N$_2$O$_2$S: C 59.01; H 3.30; N 11.47; S 13.12. Found: C 59.31; H 3.18; N 11.68; S 13.01.

REFERENCE EXAMPLE 25

2-[2-(4-Chlorophenyl)-4-methylthiazol-5-yl]-4-methylthiazole-5-carboxylic acid (a) A solution of 2-(4-chlorophenyl)-4-methylthiazole-5-carboxylic acid (0.78 g, 3 mmol; obtained in reference example 20) in thionyl chloride (10 mL) was refluxed for 4 h. The reaction mixture was evaporated to dryness, the resulting residue (0.93 g) was taken up in THF (15 mL) and then was slowly added to a cooled (0° C.) 40% ammonium hydroxide solution. Volatiles were removed in vacuo and the resulting aqueous residue was filtered and dried to give 2-(4-chlorophenyl)-4-methylthiazole-5-carboxamide (0.63 g, 79%) as a white solid: mp 236°–237° C.; $^1$H NMR (300 MHz, CDCl$_3$+MeOH—d$_4$) δ (TMS) 7.80 (d, J=8.4, 2H, arom), 7.36 (d, J=8.4, 2H, arom), 2.66 (s, 3H, Me-thiazole).

(b) To a solution of the product obtained in section (a) (0.89 g, 3.52 mmol) in a mixture of toluene (15 mL) and THF (15 mL) was added Lawesson's reagent (0.85 g, 2.11 mmol) and the resulting yellow solution was refluxed for 2 h. The reaction mixture was evaporated to dryness and the resulting product (2-(4-chlorophenyl)-4-methylthiazole-5-carbothioamide, 2.19 g) was then allowed to react with methyl 2-chloroacetoacetate in a similar manner to that described in section a of reference example 19. Methyl 2-[2-(4-chlorophenyl)-4-methylthiazol-5-yl]-4-methylthiazole-5-carboxylate was isolated by flash chromatography as a yellow solid (0.59 g, 46%): mp 174°–175° C.; $^1$H NMR (300 MHz, CDCl$_3$+MeOH—d$_4$) δ (TMS) 7.90 (d, J=8.4, 2H, arom), 7.42 5 (d, J=8.4, 2H, arom), 3.91 (s, 3H, OMe)), 2.766 (s, 3H, Me-thiazole), 2.761 (s, 3H, Me-thiazole). Analysis calculated for C$_{16}$H$_{13}$ClN$_2$O$_2$S$_2$: C 52.67; H 3.59; N 7.68; S 17.57. Found: C 52.53; H 3.87; N 7.29; S 17.01.

(c) Following the hydrolysis procedure described in section b of reference example 2 the title compound was obtained as a slightly yellowish solid: mp 265°–268° C.; $^1$H NMR (300 MHz, CDCl$_3$) δ (TMS) 8.15 (dt, J$_r$=1.6, J$_d$=8.3, 2H, arom), 7.84 (dt, J$_r$=1.6, J$_d$=8.3, 2H, arom), 2.74 (s, 6H, Me-thiazole). Analysis calculated for C$_{15}$H$_{11}$ClN$_2$O$_2$S$_2$: C 51.35; H 3.16; N 7.98; S 18.28. Found: C 51.32; H 3.12; N 7.78; S 17.43.

REFERENCE EXAMPLE 26

2-(4-Chlorophenyl)-4-trifluoromethylthiazole-5-carboxylic acid (a) Following the procedure described in section a of reference example 19 but using ethyl 2-chloro-4,4,4-trifluoroacetoacetate and 4-chlorophenylthiobenzamide, ethyl 2-(4-chlorophenyl)-4-trifluoromethyl-thiazole-5-carboxylate was obtained as a white solid, unpurified with a small amount of starting material: $^1$H NMR (300 MHz, CDCl$_3$) δ (TMS) 7.81 (dt, J$_r$=2.4, J$_d$=8.7, 2H, arom), 7.42 (dt, J$_r$=2.4, J$_d$=8.7, 2H, arom), 4.3–4.2 (m, 2H, OCH$_2$), 1.32 (t, J=7, 3H, OCH$_2$CH$_3$).

(b) Following the hydrolysis procedure described in section b of reference example 19 the title compound was obtained as a white solid: mp 235°–250° C.; $^1$H NMR (300 MHz, CDCl$_3$) δ (TMS) 7.95 (dt, J$_r$=2.4, J$_d$=8.7, 2H, arom), 7.43 (d, J=8.3, 2H, arom). Analysis calculated for C$_{11}$H$_5$ClF$_3$NO$_2$S: C 42.94; H 1.64; N 4.55; S 10.42. Found: C 43.34; H 1.66; N 4.48; S 9.93.

REFERENCE EXAMPLE 27

4-Trifluoromethyl-2-(4-trifluoromethylphenyl) thiazole-5-carboxylic acid (a) Following the procedure described in section a of reference example 19 but using ethyl 2-chloro-4,4,4-trifluoroacetoacetate and 4-trifluoromethylphenylthiobenzamide, ethyl 4-trifluoromethyl-2-(4-trifluoromethylphenyl)thiazole-5-carboxylate was obtained as a white solid, which still contained a small amount of starting material: $^1$H NMR (300 MHz, CDCl$_3$) δ (TMS) 8.01 (d, J=8.1, 2H, arom), 7.71 (d, J=8.1, 2H, arom), 4.3–4.2 (m, 2H, OCH$_2$), 1.34 (t, J=7, 3H, OCH$_2$CH$_3$).

(b) Following the hydrolysis procedure described in section b of reference example 19 the title compound was obtained as a white solid: mp 177°–179° C.; $^1$H NMR (300 MHz, CDCl$_3$) δ (TMS) 8.14 (d, J=8.2, 2H, arom), 7.75 (d, J=8.2, 2H, arom). Analysis calculated for C$_{12}$H$_5$F$_6$NO$_2$S: C 42.24; H 1.48; N 4.10; S 9.40. Found: C 41.86; H 1.33; N 4.03; S 8.92.

REFERENCE EXAMPLE 28

2-(4-Cyanophenyl)-4-trifluoromethylthiazole-5-carboxylic acid (a) Following the procedure described in section a of reference example 24 but using ethyl 2-chloro-4,4,4- trifluoroacetoacetate, ethyl 2-(4-cyanophenyl)-4-trifluoromethylthiazole-5-carboxylate was obtained as a white solid, which still contained a small amount of starting material.

(b) Following the hydrolysis procedure described in section b of reference example 24 the title compound was obtained as a white solid: mp 195°–196° C.; $^1$H NMR (300 MHz, CDCl$_3$+MeOH—d$_4$) δ (TMS) 8.10 (d, J=8.1, 2H, arom), 7.78 (d, J=8.1, 2H, arom). Analysis calculated for C$_{12}$H$_5$F$_3$N$_2$O$_2$S: C 48.33; H 1.69; N 9.39; S 10.75. Found: C 48.36; H 1.88; N 9.08; S 9.97.

REFERENCE EXAMPLE 29

2-[(4-Chlorophenoxy)methyl]-4-methylthiazole-5-carboxylic acid (a) Following the procedure described in section a of reference example 19 methyl 2-[(4-chlorophenoxy)methyl]-4-methylthiazole-5-carboxylate was obtained as a white solid: mp 88°–89° C.; $^1$H NMR (300 MHz, CDCl$_3$) δ (TMS) 7.25 (dt, J$_t$=2.1, J$_d$=8.9, 2H, arom), 6.90 (dt, J$_t$=2.1, J$_d$=8.9, 2H, arom), 5.27 (s, 2H, CH$_2$O), 3.86 (s, 3H, OMe), 2.73 (s, 3H, Me-thiazole). Analysis calculated for C$_{13}$H$_{12}$ClNO$_3$S: C 52.44; H 4.06; N 4.70; S 10.77. Found: C 51.09; H 4.03; N 5.18; S 10.19.

(b) Following the hydrolysis procedure described in section b of reference example 24, but allowing the reaction to proceed overnight, the title compound was obtained as a white solid: mp 233°–234° C.; $^1$H NMR (300 MHz, CDCl$_3$+MeOH—d$_4$) δ (TMS) 7.21 (dt, J$_t$=2.2, J$_d$=9, 2H, arom), 6.88 (dt, J$_t$=2.2, J$_d$=9, 0 2H, arom), 5.22 (s, 2H, CH$_2$O), 2.66 (s, 3H, Me-thiazole). Analysis calculated for C$_{12}$H$_{10}$ClNO$_3$S: C 50.80; H 3.55; N 4.94; S 11.30. Found: C 51.13; H 3.57; N 4.97; S 11.12.

REFERENCE EXAMPLE 30

2-[N-(4-Chlorophenyl)amino]-4-methylthiazole-5-carboxylic acid (a) Following the procedure described in section a of reference example 19, but using 4-chlorophenylthiourea, methyl 2-[N-(4-chlorophenyl)amino]-4-methylthiazole-5-carboxylate was obtained as a white solid: mp 172°–173° C.; $^1$H NMR (300 MHz, CDCl$_3$+MeOH—d$_4$) δ (TMS) 7.43 (dt, J$_t$=2.3, J$_d$=8.9, 2H, arom), 7.34 (dt, J$_t$=2.3, J$_d$=8.9, 2H, arom), 4.07 (br s, 1H, NH), 3.83 (s, 3H, OMe), 2.64 (s, 3H, Me-thiazole). Analysis calculated for C$_{12}$H$_{11}$ClN$_2$O$_2$S: C 50.98; H 3.92; N 9.91; S 11.34. Found: C 51.21; H 3.80; N 9.81; S 10.11.

(b) Following the hydrolysis procedure described in section b of reference example 2 but heating the reaction at reflux overnight the title compound was obtained as a white solid: mp>250° C.; $^1$H NMR (300 MHz, CDCl$_3$+MeOH—d$_4$) δ (TMS) 7.40 (dt, J$_t$=2.1, J$_d$=9, 2H, arom), 7.30 (dt, J$_t$=2.1, J$_d$=9, 2H, arom), 2.58 (s, 3H, Me-thiazole). Analysis calculated for C$_{11}$H$_9$ClN$_2$O$_2$S: C 49.17; H 3.38; N 10.42; S 11.93. Found: C 49.29; H 3.31; N 10.32; S 11.32.

REFERENCE EXAMPLE 31

2-(4-Chlorophenyl)thiazole-4-carboxylic acid (a) A solution of ethyl bromopyruvate (354 mg, 1.8 mmol) and 4-chlorothiobenzamide (283 g, 1.65 mmol) in EtOH (40 mL) was refluxed for 3 h. The mixture was evaporated to dryness and the resulting oil was purified by flash chromatography to give ethyl 2-(4-chlorophenyl)thiazole-4-carboxylate as a colourless oil: $^1$H NMR (80 MHz, CDCl$_3$) δ (TMS) 8.15 (s, 1H, thiazole), 7.95 (dt, J$_t$=2, J$_d$=8.5, 2H, arom), 7.42 (dt, J$_t$=2, J$_d$=8.5, 2H, arom), 4.45 (q, J=7, 2H, OCH$_2$), 1.43 (t, J=7, 3H, OCH$_2$CH$_3$). Analysis calculated for C$_{12}$H$_{10}$ClNO$_2$S: C 53.84; H 3.76; N 5.23; S 11.97. Found: C 53.65; H 3.77; N 5.23; S 11.51.

(b) Following the hydrolysis procedure described in section b of reference example 2 but heating the solution overnight, the title compound was obtained as a white solid: mp 189°–190° C.; $^1$H NMR (80 MHz, CDCl$_3$) δ (TMS) 8.29 (s, 1H, thiazole), 7.93 (dt, J$_t$=2, J$_d$=8.5, 2H, arom), 7.45 (dt, J$_t$=2, J$_d$=8.5, 2H, arom). Analysis calculated for C$_{10}$H$_6$ClNO$_2$S: C 50.11 H 2.52; N 5.84; S 13.35. Found: C 50.21; H 2.45; N 5.79; S 13.21.

REFERENCE EXAMPLE 32

2-(4-Trifluoromethylphenyl)thiazole-4-carboxylic acid (a) Following the procedure described in section a of reference example 31 ethyl 2-(4-trifluoromethylphenyl)thiazole-4-carboxylate was obtained as a white solid: mp 102°–103° C.; $^1$H NMR (80 MHz, CDCl$_3$) δ (TMS) 8.21 (s, 1H, thiazole), 8.15 (d, J=8.3, 2H, arom), 7.71 (d, J=8.3, 2H, arom), 4.47 (q, J=7, 2H, OCH$_2$), 1.44 (t, J=7, 3H, OCH$_2$CH$_3$). Analysis calculated for C$_{13}$H$_{10}$F$_3$NO$_2$S: C 51.83; H 3.35; N 4.65; S 10.64. Found: C 51.91; H 3.34; N 4.61; S 10.29.

(b) Following the hydrolysis procedure described in section b of reference example 31 the title compound was obtained as a white solid: mp 188°–189° C.; $^1$H NMR (80 MHz, CDCl$_3$) δ (TMS) 8.37 (s, 1H, thiazole), 8.13 (d, J=8.5, 2H, arom), 7.73 (d, J=8.5, 2H, arom). Analysis calculated for C$_{11}$H$_6$F$_3$NO$_2$S: C 48.36 H 2.21; N 5.13; S 11.73. Found: C 48.46; H 2.22; N 5.17; S 11.75.

REFERENCE EXAMPLE 33

2-Phenylthiazole-4-carboxylic acid (a) Following the procedure described in section a of reference example 31 ethyl 2-phenylthiazole-4-carboxylate was obtained as a colourless oil: $^1$H NMR (80 MHz, CDCl$_3$) δ (TMS) 8.14 (s, 1H, thiazole), 8.1–7.8 (m, 2H, arom), 7.6–7.2 (m, 3H, arom), 4.45 (q, J=7, 2H, OCH$_2$), 1.42 (t, J=7, 3H, OCH$_2$CH$_3$).

(b) Following the hydrolysis procedure described in section b of reference example 31 the title compound was obtained as an amorphous white solid: $^1$H NMR (80 MHz, CDCl$_3$) δ (TMS) 8.27 (s, $^1$H, thiazole), 8.2–7.8 (m, 2H, arom), 7.6–7.4 (m, 3H, arom).

REFERENCE EXAMPLE 34

2-[4-(2,2,3,3-Tetrafluoropropoxy)phenyl]thiazole-4-carboxylic acid (a) Following the procedure described in section a of reference example 31 ethyl 2-[4-(2,2,3,3-tetrafluoropropoxy)phenyl]thiazole-4-carboxylate was obtained as a colourless oil: $^1$H NMR (80 MHz, CDCl$_3$) δ (TMS) 8.11 (s, $^1$H, thiazole), 7.98 (dt, J$_t$=2, J$_d$=8.8, 2H, arom), 6.98 (dt, J$_t$=2, J$_d$=8.8, 2H, arom), 6.06 (tt, J=4.6,J=53, 1H, CHF$_2$), 4.41 (tt, J=1.5, J=11.8, 2H, CH$_2$), 4.35 (q,J=7, 2H, OCH$_2$), 1.42 (t, J=7, 3H, OCH$_2$CH$_3$).

(b) Following the hydrolysis procedure described in section b of reference example 31 the title compound was obtained as a white solid: mp 170°–173° C.; $^1$H NMR (80 MHz, CDCl$_3$) δ (TMS) 8.95 (s, 1H, thiazole), 8.70 (dt, J$_t$=2, J$_d$=8.8, 2H, arom), 7.75 (dt, J$_t$=2, J$_d$=8.8, 2H, arom), 6.79 (tt, J=4.6, J=53, 1H, CHF$_2$), 5.16 (tt, J=1.5, J=11.8, 2H, CH$_2$).

REFERENCE EXAMPLE 35

5-(4-Cyanophenyl)thiophene-2-carboxylic acid (a) Following the procedure described in Hauptmann et al, *Tetrahedron Lett.* 1968, 1317, ethyl 5-(4-cyanophenyl) thiophene-2-carboxylate was obtained as a white solid: mp 133°–134° C.; $^1$H NMR (300 MHz, CDCl$_3$) δ (TMS) 7.83 (d, J=4, 1H, thiophene), 7.81 (dt, J$_t$=1.6, J$_d$=8.3, 2H, arom), 7.70 (dt, J$_t$=1.6, J$_d$=8.3, 2H, arom), 7.43 (d, J=4, 1H, thiophene), 4.44 (q, J=7, 2H, OCH$_2$), 1.45 (t, J=7, 3H, OCH$_2$CH$_3$). Analysis calculated for C$_{14}$H$_{11}$NO$_2$S: C 65.35; H 4.31; N 5.44; S 12.46. Found: C 64.92; H 4.19; N 5.34; S 12.19.

(b) Following the hydrolysis procedure described in section b of reference example 24 the title compound was obtained as a white solid: mp>300° C.; $^1$H NMR (300 MHz, DMSO—d$_6$) δ (TMS) 7.99 (d, J=8.3, 2H, arom), 7.87 (d, J=8.3, 2H, arom), 7.74 (s, 2H, thiophene).

REFERENCE EXAMPLE 36

5-(4-Chlorophenyl)-3-methylthiophene-2-carboxylic acid (a) To a cooled (–78° C.) solution of 3-(4-chlorophenyl) -3-chloroacrolein (2.0 g, 10.4 mmol, obtained according to Hauptmann et al, *Tetrahedron Lett.* 1968, 1317) in dry THF (30 mL) was added dropwise a 3M solution of methylmagnesium bromide in THF (3.47 mL, 10.4 mmol). After the addition was complete, the reaction mixture was stirred at –78° C. for 0.5 h. Next, saturated aqueous NH$_4$Cl solution was added and the mixture was concentrated. The resulting aqueous residue was extracted with CHCl$_3$, dried, filtered, concentrated and purified by flash chromatography to give 4-(4-chlorophenyl)-4-chloro-3-buten-2-ol (1.54 g, 71%) as a colourless oil: $^1$H NMR (300 MHz, CDCl$_3$) δ (TMS) 7.51 (dt, J$_t$=2.6, J$_d$=8.6, 2H, arom), 7.33 (dt, J$_t$=2.6, J$_d$=8.6, 2H, arom), 6.18 (d, J=7.5, 1H, =CH), 4.93 (quint, J=6.4, 1H, CHOH), 1.39 (d, J=6.4, 3H, CHCH$_3$).

(b) CH$_2$Cl$_2$ (160 mL), pyridine (14 mL, 0.175mol) and CrO$_3$ (8.76 g, 87 mmol) were placed in a flask. The resulting reddish solution was cooled to 0° C., stirred for 0.5 h, and a solution of 4-(4-chlorophenyl)-4-chloro-3-buten-2-ol (2.8 g, 14.6 mmol, obtained in the preceding section) in CH$_2$Cl$_2$ (20 mL) was added dropwise. The reaction mixture was then stirred at room temperature for 4 h, filtered through celite, washed, concentrated and purified by flash chromatography to afford 4-(4-chlorophenyl)-4-chloro-3-buten-2-one as a colourless oil (1.3 g, 45%): $^1$H NMR (300 MHz, CDCl$_3$) δ (TMS) 7.61 (dt, J$_t$=2.6, J$_d$=8.6, 2H, arom), 7.39 (dt, J$_t$=2.6, J$_d$=8.6, 2H, arom), 6.75 (s, 1H, =CH), 2.47 (5, 3H, Me).

(c) Following the procedure described in the literature (see reference example 35), the compound obtained in section (b) was allowed to react with the sodium salt of ethyl mercaptoacetate to give ethyl 5-(4-chlorophenyl)-3-methylthiophene-2-carboxylate as an amorphous solid: $^1$H NMR (300 MHz, CDCl$_3$) δ (TMS) 7.54 (dt, J$_t$=2.5, J$_d$=9, 2H, arom), 7.37 (dt, J$_t$=2.5, J$_d$=9, 2H, arom), 7.11 (s, 1H, thiophene), 4.35 (q, J=7, 2H, OCH$_2$), 2.57 (s, 3H, Me-thiophene), 1.40 (t, J=7, 3H, OCH$_2$CH$_3$).

(d) Following the hydrolysis procedure described in section b of reference example 2 the title compound was obtained as a white solid: mp 245°–246° C.; $^1$H NMR (300 MHz, MeOH—d$_4$) δ (MeOH) 7.63 (dt, J$_t$=2, J$_d$=8.6, 2H, arom), 7.39 (dt, J$_t$=2, J$_d$=8.6, 2H, arom), 7.25 (s, 1H, thiophene), 2.52 (s, 3H, Me-thiophene). Analysis calculated for C$_{12}$H$_9$ClO$_2$S: C 57.03; H 3.59; S 12.69. Found: C 56.94; H 3.20; S 12.39.

REFERENCE EXAMPLE 37

5-(4-Cyanophenyl)-3-methylthiophene-2-carboxylic acid (a) Following the procedure described in reference example 36a 4-(4-cyanophenyl)-4-chloro-3-buten-2-ol was obtained as a colourless oil: $^1$H NMR (300 MHz, CDCl$_3$) δ (TMS) 7.70 (dt, J$_t$=2.1, J$_d$=8.7, 2H, arom), 7.64 (dt, J$_t$=2.1, J$_d$=8.7, 2H, arom), 6.33 (d, J=7.5, 1H, =CH), 4.95 (quint, J=6.5, 1H, CHOH), 1.41 (d, J=6.5, 3H, CHCH$_3$).

(b) Following the procedure described in reference example 36b 4-(4-cyanophenyl)-4-chloro-3-buten-2-one was obtained as a colourless oil: $^1$H NMR (300 MHz, CDCl$_3$) δ (TMS) 7.79 (dt, J$_t$=2.2, J$_d$=8.7, 2H, arom), 7.71 (dt, J$_t$=2.2, J$_d$=8.7, 2H, arom), 6.79 (s, 1H, =CH), 2.49 (s, 3H, Me).

(c) Following the procedure described in reference example 36c ethyl 5 -(4-cyanophenyl)-3-methylthiophene-2-carboxylate was obtained as a white solid: mp 129°–130° C.; $^1$H NMR (300 MHz, CDCl$_3$) δ (TMS) 7.68 (s, 4H, arom), 7.19 (s, 1H, thiophene), 4.35 (q, J=7, 2H, OCH$_2$), 2.57 (s, 3H, Me-thiophene), 1.39 (t, J=7, 3H, OCH$_2$CH$_3$).

(d) Following the hydrolysis procedure described in section b of reference example 24 the title compound was obtained as a white solid: mp 248°–253° C.; $^1$H NMR (300 MHz, CDCl$_3$) δ (TMS) 7.68 (d, J=9, 2H, arom), 7.66 (d, J=9, 2H, arom), 7.20 (s, 1H, thiophene), 2.53 (s, 3H, Me-thiophene). Analysis calculated for C$_{13}$H$_9$NO$_2$S: C 64.18; H 3.73; N 5.76; S 13.18. Found: C 64.18; H 3.71; N 5.60; S 13.00.

REFERENCE EXAMPLE 38

2-(4-Chlorophenyl)-5-methyl-3H-imidazole-4-carboxylic acid (a) A solution of ethyl 2-oximinoacetoacetate (6 g, 38 mmol; obtained according to *Org.Synth.* 1941, 21, 67) in MeCN (75 mL) was treated with 4-chlorobenzylamine (5.6 g, 40 mmol) at reflux for 18 h. Next, the reaction mixture was allowed to cool and the yellow solid formed was collected by filtration to give ethyl 2-(4-chlorophenyl)-5-methyl-3H-imidazole-4-carboxylate as a white solid (4.1 g, 40%): mp 237°–238° C.; $^1$H NMR (300 MHz, DMSO—d$_6$) δ (DMSO) 7.96 (d, J=8, 2H, arom), 7.57 (d, J=8, 2H, arom), 4.27 (q, J=7, 2H, OCH$_2$), 2.54 (s, 3H, Me-imidazole), 1.33 (t, J=7, 3H, OCH$_2$CH$_3$). Analysis calculated for C$_{13}$H$_{13}$ClN$_2$O$_2$: C 58.99; H 4.95; N 10.58. Found: C 59.20; H 4.95; N 10.59.

(b) Following the hydrolysis procedure described in section b of reference example 2 the title compound was obtained as a white solid: $^1$H NMR (300 MHz, DMSO—d$_6$) δ (DMSO) 7.98 (br), 7.50 (d, J=8.5, 2H, arom), 2.49 (s, 3H, Me-imidazole).

REFERENCE EXAMPLE 39

Mixture of 2-(4-chlorophenyl)-3,5-dimethyl-3H-imidazole-4-carboxylic acid and 2-(4-chlorophenyl) -1,5-dimethyl-1H-imidazole-4-carboxylic acid A solution of ethyl 2-(4-chlorophenyl)-5-methyl-3H-imidazole-4-carboxylate (2.7 g, 10 mmol, obtained in reference example 38) in DMF (50 mL) was treated with K$_2$CO$_3$ (1.4 g, 10 mmol) and MeI (0.95 mL, 15.3 mmol) at 60° C. for 2 h. The mixture was then evaporated to dryness and the resulting residue partitioned between EtOAc and water. The organic phase was separated, dried over Na$_2$SO$_4$, filtered and concentrated to afford a ca. 1:1 mixture of N-methylimidazole derivatives. This mixture was then hydrolyzed as described above to give a mixture of acids N-methylated on the imidazole ring. This mixture was directly used in the next step as obtained.

REFERENCE EXAMPLE 40

5-(4-Chlorophenyl)-1,3,4-oxadiazole-2-carboxylic acid (a) This product was prepared by a modification of the general procedure described in Dost, J. et al. *J.Prakt.Chem.*1985, 327, 109. To a cooled (0° C.) solution of 4-chlorobenzhydrazide (5 g, 29 mmol) and triethylamine (7.4 mL, 51 mmol) in CH$_2$Cl$_2$ (100 mL) was added dropwise ethyl oxalyl chloride (4 g, 29 mmol) and the mixture was stirred for 3 h. Next, saturated NaHCO$_3$ solution (50 mL) and CHCl$_3$ were added. The organic phase was dried over anhydrous Na$_2$SO$_4$, filtered and concentrated to give ethyl 4-chlorobenzoylhydrazinooxalate as a colourless oil which was purified by flash chromatography to yield 1.1 g of a white solid. This product was then dissolved in POCl$_3$ (30 mL) and heated at 100° C. for 15 h. The reaction mixture was evaporated to dryness and partitioned between 10% aqueous NaHCO$_3$ and CHCl$_3$. The organic phase was separated, dried over anhydrous Na$_2$SO$_4$, filtered and concentrated. The residue was purified by flash chromatography to afford ethyl 5-(4-chlorophenyl)-1,3,4-oxadiazole-2-carboxylate as a white solid (450 mg): mp 117°–118° C.; $^1$H NMR (300 MHz, CDCl$_3$) δ (TMS) 8.11 (dt, J$_r$=2.3, J$_d$=8.6, 2H, arom), 7.54 (dt, J$_r$=2.3, J$_d$=8.6, 2H, arom), 4.56 (q, J=7.1, 2H, OCH$_2$), 1.49 (t, J=7.1, 3H, OCH$_2$CH$_3$). Analysis calculated for C$_{11}$H$_9$ClN$_2$O$_3$: C 52.29; H 3.59; N 11.09. Found: C 52.70; H 3.42; N 10.89.

(b) Following the hydrolysis procedure described in section b of reference example 2, the title compound was obtained as a white solid: mp 277°–284° C.; $^1$H NMR (300 MHz, MeOH—d$_4$) δ (MeOH) 7.87 (d, J=8.5, 2H, arom), 7.51 (d, J=8.5, 2H, arom).

REFERENCE EXAMPLE 41

3-(4-Chlorophenyl)-1,2,4-oxadiazole-5-carboxylic acid (a) This product was prepared by a modification of the general procedure described in Diana et al. *J.Med.Chem.* 1995, 38, 1355. A mixture of 4-chlorobenzonitrile (5 g, 36.34 mmol), EtOH (90 mL), hydroxylamine hydrochloride (2.52 g, 36.34 mmol) and K$_2$CO$_3$ (2.51 g, 18.17 mmol) was refluxed for 20 h. The reaction mixture was concentrated, cold water was added, and it was filtered and dried to give 4-chlorobenzoamidoxime as a white solid (3.5 g, 56%). Next, this product (1.7 g, 10 mmol) was taken up in pyridine (34 mL) and treated with ethyl oxalyl chloride (2.22 mL, 20 mmol) at 0° C. The reaction mixture was stirred for 1 h, then poured into pH 7 phosphate buffer, concentrated and partitioned between CHCl$_3$ and water. The organic phase was washed with 10% aqueous NaHCO$_3$ solution, dried over Na$_2$SO$_4$, filtered, concentrated and purified by flash chromatography to give ethyl 3-(4-chlorophenyl)-1,2,4-oxadiazole-5-carboxylate as an amorphous solid (2.14 g, 85%): $^1$H NMR (300 MHz, CDCl$_3$) δ (TMS) 8.18 (dt, J$_r$=2.2, J$_d$=8.6, 2H, arom), 7.56 (dt, J$_r$=2.2, J$_d$=8.6, 2H, arom), 4.66 (q, J=7.1, 2H, OCH$_2$), 1.57 (t, J=7.1, 3H, OCH$_2$CH$_3$).

(b) This product was subjected to the hydrolysis procedure described in reference example 24 for 1 h to give the title compound as a white solid, which contained a small amount of the decarboxylated product: mp 43°–44° C.; $^1$H NMR (300 MHz, CDCl$_3$+MeOH—d$_4$) δ (TMS) 7.63 (d, J=9, 2H, arom), 7.50 (d, J=9, 2H, arom).

REFERENCE EXAMPLE 42

5-(4-Chlorophenyl)-1,2,4-oxadiazole-3-carboxylic acid (a) This product was prepared by a modification of the general procedure described in Shimizu, T. et al. *Bull.Chem. Soc.Jpn.* 1985, 58, 2519. A mixture of 4-chlorobenzonitrile (1.7 g, 12.2 mmol), and diethyl nitromalonate (2.5 g, 12.2 mmol) in dodecane (20 mL) was heated at 150° C. for 15 h. After the reaction was complete, the mixture was allowed to cool to room temperature and was then concentrated in vacuo. The residue was purified by flash chromatography to yield ethyl 5-(4-chlorophenyl)-1,2,4-oxadiazole-3-carboxylate as a light brown solid: mp 88°–89° C.; $^1$H NMR (300 MHz, CDCl$_3$) δ (TMS) 8.15 (dt, J$_r$=2.3, J$_d$=8.7, 2H, arom), 7.54 (dt, J$_r$=2.3, J$_d$=8.7, 2H, arom), 4.55 (q, J=7.1, 2H, OCH$_2$), 1.47 (t, J=7.1, 3H, OCH$_2$CH$_3$).

(b) Following the hydrolysis procedure described in section b of reference example 2 the title compound was obtained as a white solid, contaminated with a small amount of the decarboxylated product: $^1$H NMR (300 MHz, CDCl$_3$+MeOH—d$_4$) δ (TMS) 8.11 (d, J=9, 2H, arom), 7.51 (d, J=9, 2H, arom).

REFERENCE EXAMPLE 43

2-(4-tert-Butylphenyl)-4-methylthiazole-5-carboxylic acid (a) Following the procedure described in section a of reference example 19 methyl 2-(4-tert-butylphenyl)-4-methylthiazole-5-carboxylate was obtained as a colourless oil: $^1$H NMR (300 MHz, CDCl$_3$) δ (TMS) 7.89 (dt, J$_r$=2.2, J$_d$=8.6, 2H, arom), 7.46 (dt, J$_r$=2.2, J$_d$=8.6, 2H, arom), 3.89 (s, 3H, OMe), 2.78 (s, 3H, Me-thiazole), 1.35 (s, 9H, CMe$_3$).

(b) Following the hydrolysis procedure described in section b of reference example 2 the title compound was obtained as a white solid: mp 190°–193° C.; $^1$H NMR (300 MHz, MeOH—d$_4$) δ (MeOH) 7.89 (dt, J$_r$=2.2, J$_d$=8.6, 2H, arom), 7.53 (dt, J$_r$=2.2, J$_d$=8.6, 2H, arom), 2.72 (s, 3H, Me-thiazole), 1.36 (s, 9H, CMe$_3$). Analysis calculated for C$_{15}$H$_{17}$NO$_2$S: C 65.43; H 6.22; N 5.09; S 11.64. Found: C 65.41; H 6.22; N 4.92; S 10.84.

EXAMPLE 1

(1R,2R)-1-(4-Chlorophenyl)-N-[2-(2,4-difluorophenyl)-2-hydroxy-1-methyl-3-(1H-1,2,4-triazol-1-yl)propyl]-1H-pyrazole-4-carboxamide To a solution of (2R,3R)-3-amino-2-(2,4-difluorophenyl) -1-(1H-1,2,4-triazol-1-yl)-2-butanol (340 mg, 1.26 mmol, prepared as described in *J. Org. Chem.*, 1995, 60, 3000–3012) in DMF (6 mL) was added 1-hydroxybenzotriazole (207 mg, 1.32 mmol). Next, 1-(4-chlorophenyl)-1H-pyrazole-4-carboxylic acid (280 mg, 1.26 mmol, obtained in reference example 1) and DCC (272 mg, 1.32 mmol) were added and the mixture was stirred at room temperature for 18 h. The reaction mixture was then cooled to 0° C. and the dicyclohexylurea formed was filtered, washed with CHCl$_3$ and the remaining solution was evaporated to dryness and partitioned between 10% aqueous NaHCO$_3$ solution and CHCl$_3$. The layers were separated and the organic phase was dried over Na$_2$SO$_4$, filtered and concentrated. The residue was purified by flash chromatography (hex: EtOAc 1:1 then 1:3) to afford the title product, which was recrystallized from EtOAc: ether: hexane to yield a white solid (560 mg, 94%): mp 212°–213° C.; $^1$H NMR (80 MHz, CDCl$_3$) δ (TMS) 8.39 (s, 1H, pyrazole), 8.02 (s, 1H, pyrazole), 7.9–7.2 (m, 7H, arom), 7.0–6.6 (m, 2H, arom), 6.43 (br d, J=9, 1H, NH), 5.35 (d, J=1.3, 1H, OH), 5.06 (d, J=14.5, 1H, TrCH(H)), 5.1–4.8 (m, 1H, CHMe), 4.50 (d, J=14.5, 1H, TrCH(H)), 1.02 (d, J=7, 3H, MeCH); $[\alpha]^D$=–106.3° (c 1, CHCl$_3$). Analysis calculated for C$_{22}$H$_{19}$ClF$_2$N$_6$O$_2$: C 55.88; H 4.05; N 17.77. Found: C 55.96; H 4.06; N 17.55.

EXAMPLE 2

(1R,2R)-1-(4-Chlorophenyl)-N-[2-(2,4-difluorophenyl)-2-hydroxy-1-methyl-3-(1H-1,2,4-triazol-1-yl)propyl]-5-methyl-1H-pyrazole-4-carboxamide Following a similar procedure to that described in example 1 but using 1-(4-chlorophenyl)-5-methyl-1H-pyrazole-4-carboxylic acid (reference example 2) the title compound was obtained as a white solid: mp 154°–155° C.; $^1$H NMR (80 MHz, CDCl$_3$) δ (TMS) 7.90 (s, 1H, triazole), 7.79 (s, 2H, triazole, pyrazole), 7.6–7.2 (m, 5H, arom), 7.0–6.6 (m, 2H, arom), 6.37 (br d, J=9, 1H, NH), 5.35 (d, J=1.3, 1H, OH), 5.06 (d, J=14.5, 1H, TrCH(H)), 5.1–4.8 (m, 1H, CHMe), 4.50 (d, J=14.5, 1H, TrCH(H)), 2.61 (s, 3H, Me-pyrazole), 1.02 (d, J=7, 3H, MeCH); $[\alpha]^D$=–91.4° (c 1, CHCl$_3$). Analysis calculated for C$_{23}$H$_{21}$ClF$_2$N$_6$O$_2$: C 56.74; H 4.35; N 17.26. Found: C 56.79; H 4.62; N 17.15.

EXAMPLE 3

(1R,2R)-1-(4-Chlorophenyl)-N-[2-(2,4-difluorophenyl)-2-hydroxy-1-methyl-3-(11H-1,2,4-triazol-1-yl)propyl]-5-trifluoromethyl-1H-pyrazole-4-carboxamide Following a similar procedure to that described in example 1 but using 1-(4-chlorophenyl)-5-trifluoromethyl-1H-pyrazole-4-carboxylic acid the title compound was obtained as a white solid: mp 138°–139° C.; $^1$H NMR (80 MHz, CDCl$_3$) δ (TMS) 7.98 (s, 1H, triazole), 7.79 (s, 2H, triazole, pyrazole), 7.6–7.2 (m, 5H, arom), 7.0–6.6 (m, 2H, arom), 6.48 (br d, J=9, 1H, NH), 5.31 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 1.02 (d, J=7, 3H, MeCH); $[\alpha]^D$=–103.6° (c 1, CHCl$_3$). Analysis calculated for C$_{23}$H$_{18}$N$_6$ClF$_5$N$_6$O$_2$: C 51.07; H 3.35; N 15.54. Found: C 50.66; H 3.41; N 15.39.

EXAMPLE 4

(1R,2R)-1-(4-Chlorophenyl)-N-[2-(2,4-difluorophenyl)-2-hydroxy-1-methyl-3-(1H-1,2,4-triazol-1-yl)propyl]-5-propyl-1H-pyrazole-4-carboxamide Following a similar procedure to that described in example 1 but using 1-(4-chlorophenyl)-5-propyl-1H-pyrazole-4-carboxylic acid the title compound was obtained as an amorphous solid: $^1$H NMR (80 MHz, CDCl$_3$) δ (TMS) 7.88 (s, 1H, triazole), 7.79 (s, 2H, triazole, pyrazole), 7.6–7.2 (m, 5H, arom), 7.0–6.6 (m, 2H, arom), 6.38 (br d, J=9, 1H, NH), 5.35 (d, 3=1.3, 1H, OH), 5.05 (d, J=14.5, 1H, TrCH(H)), 5.1–4.8 (m, 1H, CHMe), 4.50 (d, J=14.5, 1H, TrCH(H)), 3.2–2.8 (m, 2H, Pr), 1.7–1.5 (m, 2H, Pr), 1.02 (d, J=7, 3H, MeCH), 0.87 (t, 3H, Pr); $[\alpha]^D$=–79.5° (c 1, CHCl$_3$). Analysis calculated for C$_{25}$H$_{25}$ClF$_2$N$_6$O$_2$: C 58.31; H 4.89; N 16.32. Found: C 58.14; H 5.14; N 16.36.

EXAMPLE 5

(1R,2R)-1-(4-Chlorophenyl)-N-[2-(2,4-difluorophenyl)-2-hydroxy-1-methyl-3-(1H-1,2,4-triazol-1-yl)propyl]-5-isopropyl-1H-pyrazole-4-carboxamide Following a similar procedure to that described in example 1 but using 1-(4-chlorophenyl)-5-isopropyl-1H-pyrazole-4-carboxylic acid (reference example 3) the title compound was obtained as an amorphous solid: mp 85°–92° C.; $^1$H NMR (80 MHz, CDCl$_3$) δ (TMS) 7.83 (s, 1H, pyrazole), 7.79 (s, 2H, triazole), 7.6–7.2 (m, 5H, arom), 7.0–6.6 (m, 2H, arom), 6.41 (br d, J=10, 1H, NH), 5.32 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 3.4–3.1 (m, 1H, CHMe$_2$), 1.38 (d, J=7, 6H, CHMe$_2$), 1.02 (d, J=7, 3H, MeCH); $[\alpha]^D$=–82.5° (c 1, CHCl$_3$). Analysis calculated for C$_{25}$H$_{25}$ClF$_2$N$_6$O$_2$.½H$_2$O: C 57.30; H 5.00; N 16.04. Found: C 57.04; H 5.27; N 15.73.

EXAMPLE 6

(1R,2R)-5-tertButyl-1-(4-chlorophenyl)-N-[2-(2,4-difluorophenyl)-2-hydroxy-1-methyl-3-(1H-1,2,4-triazol-1-yl)propyl]-1H-pyrazole-4-carboxamide Following a similar procedure to that described in example 1 but using 5-tertbutyl-1-(4-chlorophenyl)-1H-pyrazole-4-carboxylic acid (reference example 4) the title compound was obtained as a white solid: mp 191°–192° C.; $^1$H NMR (80 MHz, CDCl$_3$) δ (TMS) 7.80 (s, 2H, triazole), 7.68 (s, 1H, pyrazole), 7.6–7.2 (m, 5H, arom), 7.0–6.6 (m, 2H, arom), 6.45 (br d, J=10, 1H, NH), 5.31 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 1.31 (s, 9H, t-Bu), 1.02 (d, J=7, 3H, MeCH); $[\alpha]^D$=–92.0° (c 1, CHCl$_3$). Analysis calculated for C$_{26}$H$_{27}$ClF$_2$N$_6$O$_2$: C 59.03; H 5.14; N 15.89. Found: C 59.36; H 5.66; N 15.87.

EXAMPLE 7

(1R,2R)-1-(4-Chlorophenyl)-5-cyclopropyl-N-[2-(2,4-difluorophenyl)-2-hydroxy-1-methyl-3-(1H-1,2,4-triazol-1-yl)propyl]-1H-pyrazole-4-carboxamide Following a similar procedure to that described in example 1 but using 1-(4-chlorophenyl)-5-cyclopropyl-1H-pyrazole-4-carboxylic acid (reference example 5) the title compound was obtained as a white solid: mp 181°–182° C.; $^1$H NMR (80 MHz, CDCl$_3$) δ (TMS) 8.06 (s, 1H, pyrazole), 7.79 (s, 2H, triazole), 7.49 (s, 4H, arom), 7.6–7.2 (m, 1H, arom), 7.0–6.6 (m, 3H, arom, NH), 5.33 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 2.2–1.8 (m, 1H, c-prop), 1.3–1.0 (m, 2H, c-Pr), 1.04 (d, J=7, 3H, MeCH), 0.8–0.5 (m, 2H, c-pr); $[\alpha]^D$=–112.6° (c 1, CHCl$_3$). Analysis calculated for C$_{25}$H$_{23}$ClF$_2$N$_6$O$_2$: C 58.54; H 4.52; N 16.38. Found: C 58.90; H 4.87; N 16.27.

EXAMPLE 8

(1R,2R)-N-[2-(2,4-Difluorophenyl)-2-hydroxy-1-methyl-3-(1H-1,2,4-triazol-1-yl)propyl]-5-methyl-1-(4-trifluoromethylphenyl)-1H-pyrazole-4-carboxamide Following a similar procedure to that described in example 1 but using 5-methyl-1-(4-trifluoromethylphenyl)-1H-pyrazole-4-carboxylic acid (reference example 6) the title compound was obtained as a white solid: mp 180°–181° C.; $^1$H NMR (80 MHz, CDCl$_3$) δ (TMS) 8.02 (s, 1H), 7.9–7.2 (m, arom), 7.0–6.6 (m, 2H, arom), 6.37 (br d, J=10, 1H, NH), 5.37 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 2.69 (s, 3H, Me-pyrazole), 1.04 (d, J=7, 3H, MeCH); $[α]^D$=−90.8° (c 1, CHCl$_3$). Analysis calculated for C$_{24}$H$_{21}$F$_5$N$_6$O$_2$: C 55.39; H 4.07; N 16.15. Found: C 55.57; H 4.27; N 16.01.

EXAMPLE 9

(1R,2R)-1-(4-Bromophenyl)-N-[2-(2,4-difluorophenyl)-2-hydroxy-1-methyl-3-(1H-1,2,4-triazol-1-yl)propyl]-5-methyl-1H-pyrazole-4-carboxamide Following a similar procedure to that described in example 1 but using 1-(4-bromophenyl)-5-methyl-1H-pyrazole-4-carboxylic acid (reference example 7) the title compound was obtained as a white solid: mp 153°–154° C.; $^1$H NMR (300 MHz, CDCl$_3$) δ (TMS) 7.91 (s, 1H, pyrazole), 7.81 (s, 1H, triazole), 7.80 (s, 1H, triazole), 7.66 (d, J=8.7, 2H, arom), 7.4 (dt, J$_d$=6.5, J$_t$=8.8, 1H, arom), 7.32 (d, J=8.7, 2H, arom), 6.8–6.6 (m, 2H, arom), 6.35 (br d, J=9.5, 1H, NH), 5.36 (d, J=1.3, 1H, OH), 5.05 (d, J=14.5, 1H, TrCH(H)), 5.1–4.8 (m, 1H, CHMe), 4.53 (d, J=14.5, 1H, TrCH(H)), 2.63 (s, 3H, Me-pyrazole), 1.03 (d, J=6.8, 3H, MeCH); MS 306 and 308 (ethylaminoacyl group, C$_{13}$H$_{13}$BrN$_3$O), 263 and 265 (acyl group, C$_{11}$H$_8$BrN$_2$O), 224 (Tr—CH$_2$COHAr, C$_{10}$H$_8$F$_2$N$_3$O); $[α]^D$=−86.8° (c 1, CHCl$_3$). Analysis calculated for C$_{23}$H$_{21}$BrF$_2$N$_6$O$_2$: C 51.99; H 3.98; N 15.82. Found: C 52.10; H 4.01; N 15.76.

EXAMPLE 10

(1R,2R)-N-[2-(2,4-Difluorophenyl)-2-hydroxy-1-methyl-3-(1H-1,2,4-triazol-1-yl)propyl]-5-trifluoromethyl-1-(4-trifluoromethylphenyl)-1H-pyrazole-4-carboxamide Following a similar procedure to that described in example 1 but using 5-trifluoromethyl-(4-trifluoromethylphenyl)-1H-pyrazole-4-carboxylic acid (reference example 8) the title compound was obtained as a white solid: mp 141°–143° C.; $^1$H NMR (80 MHz, CDCl$_3$) δ (TMS) 8.02 (s, 1H), 7.9–7.2 (m, arom), 7.0–6.4 (m, 3H, arom, NH), 5.31 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 1.02 (d, J=7, 3H, MeCH); $[α]^D$=−86.3° (c 1, CHCl$_3$). Analysis calculated for C$_{24}$H$_{18}$F$_8$N$_6$O$_2$: C 50.18; H 3.16; N 14.63. Found: C 49.75; H 3.20; N 14.45.

EXAMPLE 11

(1R,2R)-N-[2-(2,4-Difluorophenyl)-2-hydroxy-1-methyl-3-(1H-1,2,4-triazol-1-yl)propyl]-1-(2,4-difluorophenyl)-5-methyl-1H-pyrazole-4-carboxamide Following a similar procedure to that described in example 1 but using 1-(2,4-difluorophenyl)-5-methyl-1H-pyrazole-4-carboxylic acid the title compound was obtained as a white solid: mp 208°–209° C.; $^1$H NMR (80 MHz, CDCl$_3$) δ (TMS) 7.93 (s, 1H, triazole), 7.78 (s, 2H, triazole, pyrazole), 7.6–7.0 (m, 3H, arom), 7.0–6.6 (m, 3H, arom), 6.35 (br d, J=9, 1H, NH), 5.34 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 2.49 (s, 3H, Me-pyrazole), 1.02 (d, J=7, 3H, MeCH); $[α]^D$=−89.6° (c 1, CHCl$_3$). Analysis calculated for C$_{23}$H$_{20}$F$_4$N$_6$O$_2$: C 56.56; H 4.13; N 17.21. Found: C 56.88; H 4.36; N 16.83.

EXAMPLE 12

(1R,2R)-1-(3,5-Dichlorophenyl)-N-[2-1,2,4-difluorophenyl)-2-hydroxy-1-methyl-3-(1H-1,2,4-triazol-1-yl)propyl]-5-methyl-1H-pyrazole-4-carboxamide Following a similar procedure to that described in example 1 but using 1-(3,5-dichlorophenyl)-5-methyl-1H-pyrazole-4-carboxylic acid (reference example 9) the title compound was obtained as a white solid: mp 220°–221° C.; $^1$H NMR (300 MHz, CDCl$_3$) δ (TMS) 7.92 (s, 1H, pyrazole), 7.81 (s, 1H, triazole), 7.80 (s, 1H, triazole), 7.5–7.3 (m, 4H, arom), 6.8–6.6 (m, 2H, arom), 6.36 (br d, J=9.5, 1H, NH), 5.36 (d, J=1.3, 1H, OH), 5.05 (d, J=14.5, 1H, TrCH(H)), 4.96 (br quint, 1=7, 1H, CHMe), 4.53 (d, J=14.5, 1H, TrCH(H)), 2.68 (s, 3H, Me-pyrazole), 1.03 (d, J=6.8, 3H, MeCH); MS 296 and 298 (ethylaminoacyl group, C$_{13}$H$_{12}$Cl$_2$N$_3$O), 253 and 255 (acyl group, C$_{11}$H$_7$Cl$_2$N$_2$O), 224 (Tr—CH$_2$COHAr, C$_{10}$H$_8$F$_2$N$_3$O); $[α]^D$=−83.10° (c 1, CHCl$_3$). Analysis calculated for C$_{23}$H$_{20}$Cl$_2$F$_2$N$_6$O$_2$: C 52.99; H 3.87; N 16.12. Found: C 53.58; H 4.08; N 15.90.

EXAMPLE 13

(1R,2R)-1-(2,6-Dichlorophenyl)-N-[2-(2,4-difluorophenyl)-2-hydroxy-1-methyl-3-(1H-1,2,4-triazol-1-yl)propyl]-5-methyl-1H-pyrazole-4-carboxamide Following a similar procedure to that described in example 1 but using 1-(2,6-dichlorophenyl)-5-methyl-1H-pyrazole-4-carboxylic acid (reference example 10) the title compound was obtained: mp 226°–227° C.; $^1$H NMR (300 MHz, CDCl$_3$) δ (TMS) 8.03 (s, 1H, pyrazole), 7.81 (s, 2H, triazole), 7.6–7.3 (m, 4H, arom), 6.8–6.6 (m, 2H, arom), 6.42 (br d, J=9.5, 1H, NH), 5.38 (d, J=1.3, 1H, OH), 5.07 (d, J=14.5, 1H, TrCH(H)), 4.97 (br quint, J=7, 1H, CHMe), 4.57 (d, J=14.5, 1H, TrCH(H)), 2.44 (s, 3H, Me-pyrazole), 1.04 (d, J=6.8, 3H, MeCH); MS 296 and 298 (ethylaminoacyl group, C$_{13}$H$_{12}$Cl$_2$N$_3$O), 253 and 255 (acyl group, C$_{11}$H$_7$Cl$_2$N$_2$O), 224 (Tr—CH$_2$COHAr, ClOH$_8$F$_2$N$_3$O); $[α]^D$=−80.3° (c 1, CHCl$_3$). Analysis calculated for C$_{23}$H$_{20}$Cl$_2$F$_2$N$_6$O$_2$: C 52.99; H 3.87; N 16.12. Found: C 53.29; H 3.91; N 15.93.

EXAMPLE 14

(1R,2R)-1-(2-Chlorophenyl)-N-[2-(2,4-difluorophenyl)-2-hydroxy-1-methyl-3-(1H-1,2,4-triazol-1-yl)propyl]-5-methyl-1H-pyrazole-4-carboxamide Following a similar procedure to that described in example 1 but using 1-(2-chlorophenyl)-5-methyl-1H-pyrazole-4-carboxylic acid (reference example 11) the title compound was obtained as a white solid: mp 232°–233° C.; $^1$H NMR (300 MHz, CDCl$_3$) δ (TMS) 7.97 (s, 1H, pyrazole), 7.81 (s, 2H, triazole), 7.6–7.3 (m, 5H, arom), 6.8–6.6 (m, 2H, arom), 6.39 (br d, J=9.5, 1H, NH), 5.38 (d, J=1.5, 1H, OH), 5.07 (d, J=14.4, 1H, TrCH(H)), 4.97 (br quint, J=7, 1H, CHMe), 4.57 (d, J=14.4, 1H, TrCH(H)), 2.48 (s, 3H, Me-pyrazole), 1.05 (d, J=6.8, 3H, MeCH); $[\alpha]^D = -85.20$ (c 1, CHCl$_3$). Analysis calculated for C$_{23}$H$_{21}$ClF$_2$N$_6$O$_2$: C 56.74; H 4.35; N 17.26. Found: C 56.87; H 4.56; N 17.03.

EXAMPLE 15

(1R,2R)-1-(4-Chlorophenyl)-N-[2-(2,4-difluorophenyl)-2-hydroxy-1-methyl-3-(1H-1,2,4-triazol-1-yl)propyl]-3,5-dimethyl-1H-pyrazole-4-carboxamide Following a similar procedure to that described in example 1 but using 1-(4-chlorophenyl)-3,5-dimethyl-1H-pyrazole-4-carboxylic acid (reference example 12) the title compound was obtained : mp 144°–145° C.; $^1$H NMR (80 MHz, CDCl$_3$) δ (TMS) 7.978 (s, 2H, triazole), 7.6–7.2 (m, 5H, arom), 7.0–6.6 (m, 2H, arom), 6.28 (br d, J=10, 1H, NH), 5.35 (d, J=1.3, 1H, OH), 5.07 (d, J=14.5, 1H, TrCH(H)), 5.1–4.8 (m, 1H, CHMe), 4.50 (d, J=14.5,1 H, TrCH(H)), 2.56 (s, 3H, Me-pyrazole), 2.54 (s, 3H, Me-pyrazole), 1.02 (d, J=7, 3H, MeCH); $[\alpha]^D = -93.9°$ (c 1, CHCl$_3$). Analysis calculated for C$_{24}$H$_{23}$ClF$_2$N$_6$O$_2$: C 57.55; H 4.63; N 16.78. Found: C 57.91; H 4.80; N 16.53.

EXAMPLE 16

(1R,2R)-5-Amino-1-(4-chlorophenyl)-N-[2-(2,4-difluorophenyl)-2-hydroxy-1-methyl-3-(1H-1,2,4-triazol-1-yl)propyl]-1H-pyrazole-4-carboxamide Following a similar procedure to that described in example 1 but using 5-amino-1-(4-chlorophenyl)-1H-pyrazole-4-carboxylic acid (reference example 13) the title compound was obtained as a white solid: mp 181°–182° C.; $^2$H NMR (80 MHz, CDCl$_3$) δ (TMS) 7.78 (s, 2H, triazole), 7.69 (s, 1H, pyrazole), 7.50 (br 5, 4H, arom), 7.6–7.2 (m, 1H, arom), 7.0–6.6 (m, 2H, arom), 6.15 (br d, J=9, 1H, NH), 5.55 (br s, 2H, NH$_2$), 5.36 (s, 1H, OH), 5.06 (d, J=14.5, 1H, TrCH(H)), 5.1–4.8 (m, 1H, CHMe), 4.50 (d, J=14.5, 1H, TrCH(H)), 1.02 (d, J=7, 3H, MeCH); $[\alpha]^D = -86.7°$ (c 1, CHCl$_3$). Analysis calculated for C$_{22}$H$_{20}$ClF$_2$N$_7$O$_2$: C 54.16; H 4.13; N 20.10. Found: C 54.28; H 4.35; N 19.76.

EXAMPLE 17

(1R,2R)-5-Amino-N-[2-(2,4-difluorophenyl)-2-hydroxy-1-methyl-3-(1H-1,2,4-triazol-1-yl)propyl]-1-(4-trifluoromethylphenyl)-1H-pyrazole-4-carboxamide Following a similar procedure to that described in example 1 but using 5-amino-1-(4-trifluoromethylphenyl)-1H-pyrazole-4-carboxylic acid (reference example 14) the title compound was obtained as a white solid: mp 208°–210° C.; $^1$H NMR (80 MHz, CDCl$_3$) δ (TMS) 7.76 (m, 7H, triazole, arom, pyrazole), 7.6–7.3 (m, 1H, arom), 7.0–6.6 (m, 2H, arom), 6.18 (br d, J=9, 1H, NH), 5.6 (br s, 2H, NH$_2$), 5.37 (s, 1H, OH), 5.06 (d, J=14.5, 1H, TrCH(H)), 5.1–4.8 (m, 1H, CHMe), 4.50 (d, J=14.5, 1H, TrCH(H)), 1.02 (d, J=7, 3H, MeCH); $[\alpha]^D = -69.6°$ (c 1, CHCl$_3$). Analysis calculated for C$_{23}$H$_{20}$F$_5$N$_7$O$_2$.2H$_2$O: C 49.55; H 4.34; N 17.59. Found: C 49.33; H 3.99; N 17.58.

EXAMPLE 18

(1R,2R)-N-[2-(2,4-Difluorophenyl)-2-hydroxy-1-methyl-3-(1H-1,2,4-triazol-1-yl)propyl]-5-methyl-1-(3-trifluoromethylphenyl)-1H-pyrazole-4-carboxamide Following a similar procedure to that described in example 1 but using 5-methyl-1-(3-trifluoromethylphenyl)-1H-pyrazole-4-carboxylic acid (reference example 15) the title compound was obtained as a white solid: mp 146°–147° C.; $^1$H NMR (300 MHz, CDCl$_3$) δ (TMS) 7.95 (s, 1H, pyrazole), 7.82 (s, 2H, triazole), 7.6–7.5 (m, 4H, arom), 7.40 (dt, J$_d$=6.5, J$_r$=8.8, 1H, arom), 6.8–6.6 (m, 2H, arom), 6.41 (br d, J=9.5, 1H, NH), 5.37 (d, J=1.3, 1H, OH), 5.06 (d, J=14.5, 1H, TrCH(H)), 4.96 (br quint, J=7, 1H, CHMe), 4.53 (d, J=14.5, 1H, TrCH(H)), 2.67 (s, 3H, Me-pyrazole), 1.03 (d, J=6.8, 3H, MeCH); MS 296 (ethylaminoacyl group, C$_{14}$H$_{13}$F$_3$N$_3$O), 253 (acyl group, C$_{12}$H$_8$F$_3$N$_2$O), 224 (Tr—CH$_2$COHAr, C$_{10}$H$_8$F$_2$N$_3$O); $[\alpha]^D = 90.5°$ (c 1, CHCl$_3$). Analysis calculated for C$_{24}$H$_{21}$F$_5$N$_6$O$_2$: C 55.39; H 4.07; N 16.15. Found: C 55.33; H 3.97; N 16.12.

EXAMPLE 19

(1R,2R)-N-[2-(2,4-Difluorophenyl)-2-hydroxy-1-methyl-3-(1H-1,2,4-triazol-1-yl)propyl]-5-methyl-1-(4-trifluoromethoxyphenyl)-1H-pyrazole-4-carboxamide Following a similar procedure to that described in example 1 but using 5-methyl-1-(4-trifluoromethoxyphenyl)-1H-pyrazole-4-carboxylic acid (reference example 16) the title compound was obtained as a white solid: mp 134°–135° C.; $^1$H NMR (300 MHz, CDCl$_3$) δ (TMS) 7.93 (s, 1H, pyrazole), 7.815 (s, 1H, triazole), 7.810 (s, 1H, triazole), 7.6–7.3 (m, 5H, arom), 6.8–6.6 (m, 2H, arom), 6.38 (br d, J=9.5, 1H, NH), 5.37 (d, J=1.3, 1H, OH), 5.07 (d, J=14.5, 1H, TrCH(H)), 4.97 (br quint, J=7, 1H, CHMe), 4.54 (d, J=14.5, 1H, TrCH(H)), 2.65 (s, 3H, Me-pyrazole), 1.04 (d, J=6.8, 3H, MeCH); MS 312 (ethylaminoacyl group, C$_{14}$H$_{13}$F$_3$N$_3$O$_2$), 269 (acyl group, C$_{12}$H$_8$F$_3$N$_2$O$_2$), 224 (Tr—CH$_2$COHAr, C$_{10}$H$_8$F$_2$N$_3$O); $[\alpha]^D = 83.1°$ (c 1, CHCl$_3$). Analysis calculated for C$_{24}$H$_{21}$F$_5$N$_6$O$_3$: C 53.73; H 3.95; N 15.67. Found: C 53.99; H 3.94; N 15.46.

EXAMPLE 20

(1R,2R)-N-[2-(2,4-Difluorophenyl)-2-hydroxy-1-methyl-3-(1H-1,2,4-triazol-1-yl)propyl]-1-(4-methoxyphenyl)-5-methyl-1H-pyrazole-4-carboxamide Following a similar procedure to that described in example 1 but using 1-(4-methoxyphenyl)-5-methyl-1H-pyrazole-4-carboxylic acid (reference example 17) the title compound was obtained: mp 176°–177° C.; $^1$H NMR (300 MHz, CDCl$_3$) δ (TMS) 7.89 (s, 1H, pyrazole), 7.81 (s, 2H, triazole), 7.41 (dt, J$_d$=0 6.5, J$_r$=8.8, 1H, arom), 7.33 (dt, J$_r$=2.5, J$_d$=6.6, 2H, arom), 7.02 (dt, J$_r$=2.5, J$_d$=6.6, 2H, arom), 6.8–6.6 (m, 2H, arom), 6.35 (br d, J=9.5, 1H, NH), 5.37 (d, J=1.3, 1H, OH), 5.07 (d, J=14.5, 1H, TrCH(H)), 4.97 (br quint, J=7, 1H, CHMe), 4.55 (d, J=14.5, 1H, TrCH(H)), 3.88 (s, 3H, OMe), 2.59 (s, 3H, Me-pyrazole), 1.04 (d, J=6.8, 3H, MeCH); MS 258 (ethylaminoacyl group, C$_{14}$H$_{16}$N$_3$O$_2$), 215 (acyl group, C$_{12}$H$_{11}$N$_2$O$_2$), 224 (Tr—CH$_2$COHAr, C$_{10}$H$_8$F$_2$N$_3$O); $[\alpha]^D = -90.3°$ (c 1, CHCl$_3$). Analysis calculated for C$_{24}$H$_{24}$F$_2$N$_6$O$_3$: C 59.75; H 5.01; N 17.42. Found. C 59.88; H 4.91; N 17.30.

EXAMPLE 21

(1R,2R)-1-(4-Chlorophenyl)-N-[2-(2,4-difluorophenyl)-2-hydroxy-1-methyl-3-(1H-1,2,4-triazol-1-yl)propyl]pyrrole-3-carboxamide Following a similar procedure to that described in example 1 but using 1-(4-chlorophenyl)pyrrole-3- carboxylic acid (prepared as described in Fabis et al, *Org.Prep.Proced.Int.* 1995, 27, 236) the title compound was obtained as an amorphous solid: $^1$H NMR (80 MHz, CDCl$_3$) δ (TMS) 7.79 (s, 2H, triazole), 7.63 (t, J=2, 1H, pyrrole), 7.6–7.3 (m, 5H, arom), 7.02 (t, J=2, 1H, pyrrole), 7.0–6.6 (m, 2H, arom), 6.63 (t, J=2, 1H, pyrrole), 6.35 (br d, 1H, NH), 5.36 (d, J=1.3, 1H, OH), 5.06 (d, J=14.5, 1H, TrCH(H)), 5.1–4.8 (m, 1H, CHMe), 4.50 (d, J=14.5, 1H, TrCH(H)), 1.03 (d, J=7, 3H, MeCH); $[\alpha]^D$=−95.2° (c 1, CHCl$_3$). Analysis calculated for C$_{23}$H$_{20}$ClF$_2$N$_5$O$_2$: C 58.54; H 4.27; N 14.84. Found: C 58.42; H 4.26; N 14.65.

EXAMPLE 22

(1R,2R)-2-(4-Chlorophenyl)-N-[2-(2,4-difluorophenyl)-2-hydroxy-1-methyl-3-(1H-1,2,4-triazol-1-yl)propyl]thiazole-5-carboxamide Following a similar procedure to that described in example 1 but using 2-(4-chlorophenyl)thiazole-5-carboxylic acid (reference example 18) the title compound was obtained as a white solid: mp 194–195° C.; $^1$H NMR (300 MHz, CDCl$_3$) δ (TMS) 8.25 (s, 1H, thiazole), 7.93 (dt, J$_t$=2, J$_d$=9, 2H, arom), 7.81 (s, 1H, triazole), 7.79 (s, 1H, triazole), 7.45 (dt, J$_t$=2, J$_d$=9, 2H, arom), 7.39 (dt, J$_d$=6.5, J$_t$=8.8, 1H, arom), 6.8–6.6 (m, 2H, arom), 6.55 (br d, J=9.3, 1H, NH), 5.40 (d, J=1.6, 1H, OH), 5.03 (d, J=14.5, 1H, TrCH(H)), 4.95 (br quint, J=7, 1H, CHMe), 4.52 (d, J=14.5, 1H, TrCH(H)), 1.04 (d, J=6.8, 3H, MeCH); HPLC-MS 265 and 267 (ethylaminoacyl group, C$_{12}$H$_{10}$ClN$_2$OS), 222 (acyl group, C$_{10}$H$_5$ClNOS), 224 (Tr—CH$_2$COHAr, C$_{10}$OH$_8$F$_2$N$_3$O); $[\alpha]^D$=−105.6° (c 1, CHCl$_3$). Analysis calculated for C$_{22}$H$_{18}$ClF$_2$N$_5$O$_2$S: C 53.94; H 3.70; N 14.29; S 6.54. Found: C 54.04; H 3.78; N 14.16; S 6.12.

EXAMPLE 23

(1R,2R)-N-[2-(2,4-difluorophenyl)-2-hydroxy-1-methyl-3-(1H-1,2,4-triazol-1-yl)propyl]-4-methyl-2-phenylthiazole-5-carboxamide Following a similar procedure to that described in example 1 but using 4-methyl-2-phenylthiazole-5-carboxylic acid (reference example 19) the title compound was obtained as an amorphous solid: $^1$H NMR (300 MHz, CDCl$_3$) δ (TMS) 8.0–7.9 (m, 2H, arom), 7.81 (s, 1H, triazole), 7.79 (s, 1H, triazole), 7.5–7.4 (m, 3H, arom), 7.38 (dt, J$_d$=6.5, J$_t$=8.8, 1H, arom), 6.9–6.7 (m, 2H, arom), 6.40 (br d, J=9.5, 1H, NH), 5.38 (d, J=1.3, 1H, OH), 5.05 (d, J=14.2, 1H, TrCH(H)), 4.93 (br quint, J=7, 1H, CHMe), 4.53 (d, J=14.2, 1H, TrCH(H)), 2.82 (s, 3H, Me-thiazole), 1.03 (d, J=6.8, 3H, MeCH); [60 ]$^D$=−114.2° (c 1, CHCl$_3$). Analysis calculated for C$_{23}$H$_{21}$F$_2$N$_5$O$_2$S: C 58.84; H 4.51; N 14.92; S 6.83. Found: C 58.59; H 4.78; N 15.02; S 6.50.

EXAMPLE 24

(1R,2R)-N-[2-(2,4-Difluorophenyl)-2-hydroxy-1-methyl-3-(-1,2,4-triazol-1-yl)propyl]-4-methyl-2-(4-trifluoromethylphenyl)thiazole-5-carboxamide Following a similar procedure to that described in example 1 but using 4-methyl-2-(4-trifluoromethylphenyl)thiazole-5-carboxylic acid and recrystallizing the product obtained from DMF-H$_2$O, the title compound was obtained as a white solid: mp 79°–82 ° C.; $^1$H NMR (80 MHz, CDCl$_3$) δ(TMS) 8.1 (s, 1H, triazole), 8.03 (s, 1H, triazole), 7.78 (br s, arom), 7.66 (s, arom), 7.6–7.2 (1H, arom), 7.0–6.6 (m, 2H, arom), 6.4 (br d, J=9, 1H, NH), 5.38 (d, J=1.3, 1H, OH), 5.06 (d, J=14.5, 1H, TrCH(H)), 5.1–4.8 (m, 1H, CHMe), 4.50 (d, J=14.5, 1H, TrCH(H)), 2.82 (s, 3H, Me-thiazole), 1.02 (d, J=7, 3H, MeCH); $[\alpha]^D$=−103.2° (c 1, CHCl$_3$). Analysis calculated for C$_{24}$H$_{20}$F$_5$N$_5$O$_2$S: C 53.63; H 3.75; N 13.03; S 5.96. Found: C 53.77; H 3.97; N 13.51; S 5.51.

EXAMPLE 25

(1R,2R)-2-(4-Chlorophenyl)-N-[2-(2,4-difluorophenyl)-2-hydroxy-1-methyl-3-(1H-1,2,4-triazol-1-yl)propyl]-4-methylthiazole-5-carboxamide Following a similar procedure to that described in example 1 but using 2-(4-chlorophenyl)-4-methylthiazole-5-carboxylic acid (reference example 20) the title compound was obtained as a white solid: mp 159°–160° C.; $^1$H NMR (80 MHz, CDCl$_3$) δ (TMS) 8.0–7.8 (m, 4H, arom, triazole), 7.6–7.2 (m, 3H, arom), 7.0–6.6 (m, 2H, arom), 6.4 (br d, J=10, 1H, NH), 5.37 (d, J=1.3, 1H, OH), 5.06 (d, J=14.5, 1H, TrCH(H)), 5.1–4.8 (m, 1H, CHMe), 4.50 (d, J=14.5, 1H, TrCH(H)), 2.80 (s, 3H, Me-thiazole), 1.02 (d, J=7, 3H, MeCH); MS 281 and 283 (ethylaminoacyl group, C$_{13}$H$_{14}$ClN$_2$OS), 236 and 238 (acyl group, C$_{11}$H$_7$ClNOS), 224 (Tr—CH$_2$COHAr, C$_{10}$H$_8$F$_2$N$_3$O); $[\alpha]^D$=−117.1° (c 1, CHCl$_3$). Analysis calculated for C$_{23}$H$_{20}$ClF$_2$N$_5$O$_2$S: C 54.82; H 4.00; N 13.90; S 6.36. Found: C 55.13; H 3.93; N 13.86; S 6.09.

EXAMPLE 26

(1R,2R)-2-(4-Bromophenyl)-N-[2-(2,4-difluorophenyl)-2-hydroxy-1-methyl-3-(1H-1,2,4-triazol-1-yl)propyl]-4-methylthiazole-5-carboxamide Following a similar procedure to that described in example 1 but using 2-(4-bromophenyl)-4-methylthiazole-5-carboxylic acid (reference example 21) the title compound was obtained as a white solid: mp 165°–166° C.; $^1$H NMR (80 MHz, CDCl$_3$) δ (TMS) 7.71 (d, J=7.5, 2H, arom), 7.79 (s, 2H, triazole), 7.57 (d, J=7.5, 2H, arom), 7.6–7.2 (m, 1H, arom), 7.0–6.6 (m, 2H, arom), 6.43 (br d, J=10, 1H, NH), 5.39 (d, J=1.3, 1H, OH), 5.05 (d, J=14.5, 1H, TrCH(H)), 5.1–4.8 (m, 1 H, CHMe), 4.50 (d, J=14.5, 1H, TrCH(H)), 2.80 (s, 3H, Me-thiazole), 1.02 (d, J=7, 3H, MeCH); MS 323 and 325 (ethylaminoacyl group, C$_{13}$H$_{12}$BrN$_2$OS), 280 and 282 (acyl group, C$_{11}$H$_7$BrNOS), 224 (Tr—CH$_2$COHAr, C$_{10}$H$_8$F$_2$N$_3$O); $[\alpha]^D$=−108.7° (c 1, CHCl$_3$). Analysis calculated for C$_{23}$H$_{20}$BrF$_2$N$_5$O$_2$S: C 50.37; H 3.68; N 12.77; S 5.85. Found: C 50.61; H 3.66; N 12.81; S 5.62.

EXAMPLE 27

(1R,2R)-N-[2-(2,4-Difluorophenyl)-2-hydroxy-1-methyl-3-(1H-1,2,4-triazol-1-yl)propyl]-4-methyl-2-(4-trifluoromethoxyphenyl)thiazole-5carboxamide Following a similar procedure to that described in example 1 but using 4-methyl-2-(4-trifluoromethoxyphenyl)thiazole-5-carboxylic acid (reference example 22) the title compound was obtained as an amorphous solid: $^1$H NMR (300 MHz, CDCl$_3$) δ (TMS) 8.01 (dt, J$_t$=2, J$_d$=9, 2H, arom), 7.83 (s, 1H, triazole), 7.81 (s, 1H, triazole), 7.39 (dt, J$_d$=6.5, J$_t$=8.8, 1H, arom), 7.32 (d, J=9, 2H, arom), 6.8–6.6 (m, 2H, arom), 6.44 (br d, J=9.5, 1H, NH), 5.40 (d, J=1.3, 1H, OH), 5.06 (d, J=14.5, 1H, TrCH(H)), 4.95 (br quint, J=7, 1H, CHMe), 4.53 (d, J=1 4.5, 1H, TrCH(H)), 2.83 (s, 3H, Me-thiazole), 1.04 (d, J=6.8, 3H, MeCH); MS 329 (ethylaminoacyl group, C$_{14}$H$_{12}$F$_3$N$_2$O$_2$S), 286 (acyl group, C$_{12}$H$_7$F$_3$NO$_2$S), 224 (Tr—CH$_2$COHAr, C$_{10}$H$_8$F$_2$N$_3$O);

$[\alpha]^D = -105.4°$ (c 1, CHCl$_3$). Analysis calculated for C$_{24}$H$_{20}$F$_5$N$_5$O$_3$S: C 52.08; H 3.64; N 12.65; S 5.79. Found: C 52.27; H 3.88; N 12.26; S 5.40.

EXAMPLE 28

(1R,2R)-N-[2-(2,4-Difluorophenyl)-2-hydroxy-1-methyl-3-(1H-1,2,4-triazol-1-yl)propyl]-4-methyl-2-[4-(2,2,3,3-tetrafluoropropoxy)phenyl]thiazole-5-carboxamide Following a similar procedure to that described in example 1 but using 4-methyl-2-[4-(2,2,3,3-tetrafluoropropoxy)phenyl] thiazole-5-carboxylic acid (reference example 23) the title compound was obtained as an amorphous solid: $^1$H NMR (300 MHz, CDCl$_3$) δ (TMS) 7.95 (dt, $J_r$=2, $J_d$=9, 2H, arom), 7.82 (s, 1H, triazole), 7.80 (s, 1H, triazole), 7.39 (dt, $J_d$=6.5, $J_r$=8.8, 1H, arom), 7.02 (dt, $J_r$=2, $J_d$=9, 2H, arom), 6.8–6.6 (m, 2H, arom), 6.41 (br d, J=9.5, 1H, NH), 6.08 (tt, J=4.7, J=53, 1H, CF$_2$H), 5.39 (d, J=1.3, 1H, OH), 5.06 (d, J=14.5, 1H, TrCH(H)), 4.95 (br quint, J=7, 1H, CHMe), 4.53 (d, J=14.5, 1H, TrCH(H)), 4.35 (tt, J=1.3, J=12, 2H, OCH$_2$), 2.81 (s, 3H, Me-thiazole), 1.03 (d, J=6.8, 3H, MeCH); MS 375 (ethylaminoacyl group, C$_{16}$H$_{15}$F$_4$N$_2$O$_2$S), 332 (acyl group, C$_{14}$H$_{10}$F$_4$NO$_2$S), 224 (Tr—CH$_2$COHAr, C$_{10}$H$_8$F$_2$N$_3$O); $[\alpha]^D$=−85.7° (c 1, CHCl$_3$). Analysis calculated for C$_{26}$H$_{23}$F$_6$N$_5$O$_3$S: C 52.09; H 3.87; N 11.68; S 5.35. Found: C 52.23; H 3.60; N 11.62: S 5.24.

EXAMPLE 29

(1R,2R)-2-(4-Cyanophenyl)-N-[2-(2,4-difluorophenyl)-2-hydroxy-1-methyl-3 -(1H-1,2,4-triazol-1-yl)propyl]-4-methylthiazole-5carboxamide Following a similar procedure to that described in example 1 but using 2-(4-cyanophenyl)-4-methylthiazole-5-carboxylic acid (reference example 24) the title compound was obtained as a white solid: mp 109°–111° C.; $^1$H NMR (300 MHz, CDCl$_3$) δ (TMS) 8.07 (d, J=8.3, 2H, arom), 7.81 (s, 1H, triazole), 7.79 (s, 1H, triazole), 7.75 (d, J=8.3, 2H, arom), 7.37 (dt, $J_d$=6.5, $J_r$=8.8, 1H, arom), 6.8–6.6 (m, 2H, arom), 6.46 (br d, J=9.5, 1H, NH), 5.40 (s, 1H, OH), 5.03 (d, J=14.5, 1H, TrCH(H)), 4.94 (br quint, J=7, 1H, CHMe), 4.50 (d, J=14.5, 1H, TrCH(H)), 2.83 (s, 3H, Me-thiazole), 1.02 (d, J=6.8, 3H, MeCH); MS 270 (ethylaminoacyl group, C$_{14}$H$_{12}$N$_3$OS), 227 (acyl group, C$_{12}$H$_7$N$_2$OS), 224 (Tr—CH$_2$COHAr, C$_{10}$H$_8$F$_2$N$_3$O); $[\alpha]^D$=−120.80 (c 1, CHCl$_3$). Analysis calculated for C$_{24}$H$_{20}$F$_2$N$_6$O$_2$S: C 58.29; H 4.08; N 16.99; S 6.48 Found: C 57.83; H 3.96; N 16.70; S 6.16.

EXAMPLE 30

(1R,2R)-2-(4-Cyanophenyl)-N-[2-(2,4-difluorophenyl)-2-hydroxy-1-methyl-3-(1H-1,2,4-triazol-1-yl)propyl]-4-methylthiazole-5-carboxamide, oxalate To a solution of (1R,2R)-2-(4-cyanophenyl)-N-[2-(2,4-difluorophenyl)-2-hydroxy-1-methyl-3-(1H-1,2,4-triazol-1-yl)propyl]-4-methyl thiazole-5-carboxamide (obtained in example 29) in EtOH was added 2 equivalents of oxalic acid and some diethyl ether. The solution was cooled to −20° C. and the precipitate formed was collected by filtration and dried to give the title compound as a white solid: mp 104°–108° C.; $^1$H NMR (300 MHz, MeOH—d$_4$) δ (TMS) 8.28 (s, 1H, triazole), 8.14 (d, J=8.3, 2H, arom), 8.1–7.9 (m, 1H), 7.84 (d, J=8.3, 2H, arom), 7.73 (s, 1H, triazole), 7.37 (dt, $J_d$=6.5, $J_r$=8.8, 1H, arom), 7.0–6.9 (m, 1H, arom), (6.9–6.8 (m, 1H, arom), 5.1–4.9 (m, 2H, TrCH(H), CHMe), 4.59 (d, J=14.5, 1H, TrCH(H)), 2.73 (s, 3H, Me-thiazole), 1.05 (d, J=6.8, 3H, MeCH); $[\alpha]^D$ =−72° (c 1, MeOH). Analysis calculated for C$_{24}$H$_{20}$F$_2$N$_6$O$_2$S.C$_2$H$_4$O$_2$.½H$_2$O: C 52.61; H 3.90; N 14.16; S 5.39. Found: C 52.74; H 3.80; N 13.88; S 5.01.

EXAMPLE 31

(1R,2R)-2-(4-Cyanophenyl)-N-[2-(2,4-difluorophenyl)-2-hydroxy-1-methyl-3-(1H-1,2,4-triazol-1-yl)propyl]-4-methylthiazole-5-carboxamide, methane-sulfonate To a solution of (1R,2R)-2-(4-cyanophenyl)-N-[2-(2,4-difluorophenyl)-2-hydroxy-1-methyl-3-(1H-1,2,4-triazol-1-yl)propyl]-4-methylthiazole-5-carboxamide (obtained in example 29) in MeOH was added 2 equivalents of methanesulfonic acid diluted in MeOH. The solution was cooled to 0° C. and the precipitate formed was collected by filtration and dried to give the title compound as white needles: mp 126°–138° C.; $^1$H NMR (300 MHz, DMSO—d$_6$) δ (DMSO) 8.55 (s, 1H, triazole), 8.15 (d, J=9.2, 1H, NH), 8.13 (d, J=8.3, 2H, arom), 7.98 (d, J=8.3, 2H, arom), 7.87 (s, 1H, triazole), 7.30 (br q, J=8.5, 1H, arom), 7.20 (ddd, J=2.4, J=9.2, J=11.8, 1H, arom), 6.92 (dt, $J_d$=2.4, $J_r$=8.5, 1H, arom), 4.9–4.8 (m, 2H, TrCH(H), CHMe), 4.54 (d, J=14.5, 1H, TrCH(H)), 2.68 (5, 3H, Me-thiazole), 2.38 (s, 3H, MeSO$_3$H), 0.93 (d, J=6.8, 3H, MeCH); $[\alpha]^D$=−71° (c 1, DMF). Analysis calculated for C$_{24}$H$_{20}$F$_2$N$_6$O$_2$S.CH$_4$O$_3$S.H$_2$O: C 49.34; H 4.31; N 13.81; S 10.53. Found: C 49.35; H 4.11; N 13.72; S 10.30.

EXAMPLE 32

(1R,2R)-2-(4-Carbamoylphenyl)-N-[2-(2,4-difluorophenyl)-2-hydroxy-1-methyl-3-(1H-1,2,4-triazol-1-yl)propyl]-4-methylthiazole-5-carboxamide To a solution of NH$_4$OH in a H$_2$O—THF mixture was added (1R,2R)-2-(4-cyanophenyl)-N-[2-(2,4-difluorophenyl)-2-hydroxy-1-methyl-3-(1H-1,2,4-triazol-1-yl)propyl]-4-methyl thiazole-5-carboxamide methane-sulfonate (0.5 g, 0.84 mmol, obtained in example 31). The mixture was refluxed for 2 days, then was concentrated and the aqueous residue was extracted with CHCl$_3$. The organic layer was separated, dried over Na$_2$SO$_4$, filtered and the filtrate was concentrated to a solid (0.53 g). This was purified by flash chromatography to give the title compound as a white solid: 133°–135° C.; $^1$H NMR (300 MHz, CDCl$_3$) δ (TMS) 7.98 (d, J=8.3, 2H, arom), 7.87 (d, J=8.3, 2H, arom), 7.81 (s, 1H, triazole), 7.71 (s, 1H, triazole), 7.40 (dt, $J_d$=6.5, $J_r$=8.8, 1H, arom), 6.8–6.6 (m, 2H, ) arom), 6.57 (br d, J=9.5, 1H, NH), 6.27 (br s, 2H, NH$_2$), 5.63 (s, 1H, OH), 5.05 (d, J=14.5, 1H, TrCH(H)), 4.98 (br quint, J=7, 1H, CHMe), 4.57 (d, J=14.5, 1H, TrCH(H)), 2.81 (s, 3H, Me-thiazole), 1.05 (d, J=6.8, 3H, MeCH); MS 288 and 289 (ethylaminoacyl group, C$_{14}$H$_{15}$N$_3$O$_2$S), 245 (acyl group, C$_{12}$H$_9$N$_2$O$_2$S), 224 (Tr—CH$_2$COHAr, C$_{10}$H$_8$F$_2$N$_3$O); $[\alpha]^D$= −74.5° (c 1, MeOH). Analysis calculated for C$_{24}$H$_{22}$F$_2$N$_6$O$_3$S: C 56.24; H 4.33; N 16.40; S 6.26. Found: C 55.90; H 4.64; N 15.29; S 5.62.

EXAMPLE 33

(1R,2R)-2-[2-(4-Chlorophenyl)-4-methylthiazol-5-yl]-N-[2-(2,4-difluorophenyl)-2-hydroxy-1-methyl-3-(1H-1,2,4-triazol-1-yl)propyl]-4-methylthiazole-5-carboxamide Following a similar procedure to that described in example 1 but using 2-[2-(4-chlorophenyl)-4-methylthiazol- 5-yl]-4-methylthiazole-5-carboxylic acid (reference example 25) the title compound was obtained as a yellow solid: mp 110°–114° C.; $^1$H NMR (300 MHz, CDCl$_3$) δ (TMS) 7.92 (dt, J$_t$=2, J$_d$=9, 2H, arom), 7.81 (s, 1H, triazole), 7.79 (s, 1H, triazole), 7.39 (dt, J$_d$=6.5, J$_t$=8.8, 1H, arom), 7.32 (dt, J$_t$=2, J$_d$=9, 2H, arom), 6.8–6.6 (m, 2H, arom), 6.42 (br d, J=9.5, 1H, NH), 5.40 (d, J=1.1, 1H, OH), 5.05 (d, J=14.3, 1H, TrCH(H)), 4.95 (br quint, J=7, 1H, CHMe), 4.52 (d, J=14.3, 1H, TrCH(H)), 2.80 (s, 3H, Me-thiazole), 2.78 (s, 3H, Me-thiazole), 1.03 (d, J=6.8, 3H, MeCH); HPLC-MS 376 and 378 (ethylaminoacyl group, C$_{17}$H$_{15}$ClN$_3$OS$_2$), 333 and 335 (acyl group, Cl$_5$H$_{10}$ClN$_2$OS$_2$), 224 (Tr—CH$_2$COHAr, C$_1$OH$_8$F$_2$N$_3$O); [α]$^D$=–98° (c 1, CHCl$_3$). Analysis calculated for C$_{27}$H$_{23}$ClF$_2$N$_6$O$_2$S$_2$: C 53.95; H 3.86; N 13.98; S 10.67. Found: C 54.21; H 4.02; N 13.60; S 9.78.

EXAMPLE 34

(1R,2R)-2-(4-Chlorophenyl)-N-[2-(2,4-difluorophenyl)-2-hydroxy-1-methyl-3-(1H-1,2,4-triazol-1-yl)propyl]-4-trifluoromethylthiazole-5-carboxamide Following a similar procedure to that described in example 1 but using 2-(4-chlorophenyl)-4-trifluoromethylthiazole-5-carboxylic acid (reference example 26), the title compound was obtained as a white solid: mp 78°–79° C.; $^1$H NMR (300 MHz, CDCl$_3$) δ (TMS) 7.91 (dt, J$_t$=2.5, J$_d$=8.5, 2H, arom), 7.81 (s, 1H, triazole), 7.79 (s, 1H, triazole), 7.48 (dt, J$_d$=2.5, J$_t$=8.5, 2H, arom), 7.39 (dt, J$_d$=6.5, J$_t$=8.8, 1H, arom), 6.87 (br d, J=9.0, 1H, NH), 6.8–6.6 (m, 2H, arom), 5.38 (br s, 1H, OH), 5.01 (d, J=14.2, 1H, TrCH(H)), 4.91 (br quint, J=7, 1H, CHMe), 4.51 (d, J=14.2, 1H, TrCH(H)), 1.02 (d, J=6.8, 3H, MeCH); [α]$^D$=–88.8° (c 1, CHCl$_3$). Analysis calculated for C$_{23}$H$_{17}$ClF$_5$N$_5$O$_2$S: C 49.51; H 3.07; N 12.55; S 5.75. Found: C 49.86; H 3.08; N 12.36; S 5.38.

EXAMPLE 35

(1R,2R)-N-[2-(24-Difluorophenyl)-2-hydroxy-1-methyl-3-(1H-1,2,4-triazol-1-yl)propyl]-4-trifluoromethyl-2-(4-trifluoromethylphenyl) thiazole-5-carboxamide Following a similar procedure to that described in example 1 but using 4-trifluoromethyl-2-(4-trifluoromethylphenyl)thiazole-5-carboxylic acid (reference example 27), the title compound was obtained as a white solid: mp 83°–86° C.; $^1$H NMR (300 MHz, CDCl$_3$) δ (TMS) 8.12 (d, J=8.1, 2H, arom), 7.84 (5, 1H, triazole), 7.80 (s, 1H, triazole), 7.77 (d, J=8.1, 2H, arom), 7.38 (dt, J$_d$=6.5, J$_t$=8.8, 1H, arom), 6.95 (br d, J=9.0, 1H, NH), 6.8–6.6 (m, 2H, arom), 5.42 (d, J=1.6, 1H, OH), 5.03 (d, J=14.2, 1H, TrCH(H)), 4.96 (br quint, J=7, 1H, CHMe), 4.51 (d, J=14.2, 1H, TrCH(H)), 1.04 (d, J=6.8, 3H, MeCH); [α]$^D$=–79° (c 1, CHCl$_3$). Analysis calculated for C$_{24}$H$_{17}$F$_8$N$_5$O$_2$S: C 48.74; H 2.90; N 11.84; S 5.42. Found: C 49.16; H 3.19; N 11.47; S 5.03.

EXAMPLE 36

(1R,2R)-2-(4-Cyanophenyl)-N-[2-(2,4-difluorophenyl)-2-hydroxy-1-methyl-3-(1H-1,2,4-triazol-1-yl)propyl]-4-trifluoromethylthiazole-5-carboxamide Following a similar procedure to that described in example 1 but using 2-(4-cyanophenyl)-4-trifluoromethylthiazole-5-carboxylic acid (reference example 28), the title compound was obtained as a white solid: mp 101°–108° C.; $^1$H NMR (300 MHz, CDCl$_3$) δ (TMS) 8.13 (d, J=8.1, 2H, arom), 7.86 (s, 1H, triazole), 7.83 (d, J=8.1, 2H, arom), 7.83 (s, 1H, triazole), 7.40 (dt, J$_d$=6.5, J$_t$=8.8, 1H, arom), 6.98 (br d, J=9.0, 1H, NH), 6.8–6.6 (m, 2H, arom), 5.44 (d, J=1.6, 1H, OH), 5.05 (d, J=14.2, 1H, TrCH(H)), 4.96 (br quint, J=7, 1H, CHMe), 4.55 (d, J=14.2, 1H, TrCH(H)), 1.07 (d, J=6.8, 3H, MeCH); [α]$^D$=–79.9° (c 1, CHCl$_3$). Analysis calculated for C$_{24}$H$_{17}$F$_5$N$_6$O$_2$S: C 52.56; H 3.12; N 15.32; S 5.85. Found: C 51.98; H 3.51; N 11.29; S 5.16.

EXAMPLE 37

(1R,2R)-N-[2-(2,4-difluorophenyl)-2-hydroxy-1-methyl-3-(1H-1,2,4-triazol-1-yl)propyl]-2-[4-(1H-tetrazol-5yl)phenyl]-4-trifluoromethylthiazole-5-carboxamide, hydrochloride The compound obtained in the previous example (400 mg, 0.73 mmol) was treated with sodium azide (143 mg, 2.18 mmol) and triethylammonium hydrochloride (151 mg, 1.09 mmol) in NMP (5 mL) at 150° C. for 2 h. The mixture was cooled to room temperature, H$_2$O was added and it was made acidic with 6N HCl. A creamy solid (350 mg) was obtained, which was recrystallized from isopropanol to give the title compound as a creamy solid: mp>250° C.; $^1$H NMR (300 MHz, MeOH—d$_4$) δ (MeOH—d$_4$) 9.32 (s, 1H, triazole), 8.39 (s, 1H, triazole), 8.28 (d, J=8.8, 2H, arom), 8.24 (d, J=8.8, 2H, arom), 7.36 (dt, J$_d$=6.5, J$_t$=8.8, 1H, arom), 7.06 (ddd, J=2.4, J=8.7, J=11.5, 1H, arom), 6.90 (dt, J$_d$=2.1, J$_t$=8.0, 1H, arom), 5.13 (d, J=14.3, 1H, TrCH(H)), 5.01 (q, J=7, 1H, CHMe), 4.77 (d, J=14.3, 1H, TrCH(H)), 1.10 (d, J=7, 3H, MeCH); DIP/MS 367 (ethylaminoacyl group, C$_{14}$H$_{10}$F$_3$N$_6$OS), 324 (acyl group, C$_{12}$H$_5$F$_3$N$_5$OS), 224 (Tr—CH$_2$COHAr, ClOH$_8$F$_2$N$_3$O). Analysis calculated for C$_{24}$H$_{18}$F$_5$N$_9$O$_2$S.HCl.H$_2$O: C 44.62; H 3.28; N 19.51; S 4.96. Found: C 44.12; H 2.89; N 19.01; S 4.71.

EXAMPLE 38

(1R,2R)-N-[2-(2,4-Difluorophenyl)-2-hydroxy-1-methyl-3-(1H-1,2,4-triazol-1-yl)propyl]-2-[4-(2-methyl-2H-tetrazol-5-yl)phenyl]-4-trifluoromethyl thiazole-5-carboxamide The compound obtained in the preceding example (162 mg, 0.27 mmol) was treated with methyl iodide (48 mg, 0.34 mmol) and K$_2$CO$_3$ (38 mg, 0.28 mmol) in DMF (2 mL) at 25° C. for 2 h. The reaction mixture was then evaporated to dryness, and the residue partitioned between H$_2$O and CHCl$_3$. The organic phase was separated, dried and concentrated. The residue was flash chromatographed to afford mainly the title compound (38 mg) as a white solid: $^1$H NMR (300 MHz, CDCl$_3$) δ (TMS) 8.29 (d, J=8.3, 2H, arom), 8.13 (d, J=8.3, 2H, arom), 7.84 (s, 1H, triazole), 7.81 (s, 1H, triazole), 7.39 (dt, J$_d$=6.5, J$_t$=8.8, 1H, arom), 6.91 (br d, J=9.0, 1 H, NH), 6.8–6.6 (m, 2H, arom), 5.41 (d, J=1.6, 1H, OH), 5.05 (d, J=14.2, 1H, TrCH(H)), 4.94 (br quint, J=7, 1H, CHMe), 4.55 (d, J=14.2, 1H, TrCH(H)), 4.45 (s, 3H, Me-tetrazol), 1.05 (d, J=6.8, 3H, MeCH); DIP/MS 381 (ethylaminoacyl group, C$_{15}$H$_{12}$F$_3$N$_6$OS), 338 (acyl group, C$_{13}$H$_{17}$F$_3$N$_5$OS), 224 (Tr—CH$_2$COHAr, C$_{10}$H$_8$F$_2$N$_3$O).

EXAMPLE 39

(1R,2R)-2-[(4-Chlorophenoxy)methyl]-N-[2-(2,4-difluorophenyl)-2-hydroxy-1-methyl-3-(1H-1,2,4-triazol-1-yl)propyl]-4-methylthiazole-5carboxamide Following a similar procedure to that described in example 1 but using 2-[(4-chlorophenoxy)methyl]-4- methylthiazole-5-carboxylic acid (reference example 29) the title compound was obtained as a white solid: mp 134°–135° C.; $^1$H NMR (300 MHz, CDCl$_3$) δ (TMS) 7.80 (s, 1H, triazole), 7.77 (s, 1H, triazole), 7.36 (dt, J$_d$=6.5, J$_t$=8.8, 1H, arom), 7.28 (dt, J$_t$=2, J$_d$=9, 2H, arom), 6.93 (dt, J$_t$=2, J$_d$=9, 2H, arom), 6.8–6.6 (m, 2H, arom), 6.35 (br d, J=9.5, 1H, NH), 5.34 (d, J=1.3, 1H, OH), 5.30 (s, 2H, CH$_2$O), 5.02 (d, J=14.3, 1H, TrCH(H)), 4.91 (br quint, J=7, 1H, CHMe), 4.48 (d, J=14.3, 1H, TrCH(H)), 2.76 (s, 3H, Me-thiazole), 0.99 (d, J=6.8, 3H, MeCH); GC/MS 309 and 310 (ethylaminoacyl group, C$_{14}$H$_{14}$ClN$_2$O$_2$S), 266 and 268 (acyl group, C$_{12}$H$_9$ClNO$_2$S), 224 (Tr—CH$_2$COHAr, C$_{10}$H$_8$F$_2$N$_3$O); [α]$^D$=−94° (c 1, CHCl$_3$). Analysis calculated for C$_{24}$H$_{22}$ClF$_2$N$_5$O$_3$S: C 53.98; H 4.15; N 13.12; S 6.00 Found: C 54.04; H 4.48; N 12.35; S 5.27.

EXAMPLE 40

(1R,2R)-2-[N-(4-Chlorophenyl)amino]-N-[2-(2,4-difluorophenyl)-2-hydroxy-1-methyl-3-(1H-1,2,4-triazol-1-yl)propyl]-4-methylthiazole-5-carboxamide Following a similar procedure to that described in example 1 but using 2-[N-(4-chlorophenyl)amino]-4-methylthiazole-5-carboxylic acid (reference example 30) the title compound was obtained as a white amorphous solid: HPLC-MS 295 and 267 (ethylaminoacyl group, C$_{13}$H$_{14}$ClN$_3$OS), 251 and 253 (acyl group, C$_{11}$H$_8$ClN$_2$OS), 224 (Tr—CH$_2$COHAr, C$_{10}$H$_8$F$_2$N$_3$O).

EXAMPLE 41

(1R,2R)-2-(4-Chlorophenoxy)-N-[2-(2,4-difluorophenyl)-2-hydroxy-1-methyl-3-(1H-1,2,4-triazol-1-yl)propyl]-4-methylthiazole-5-carboxamide (a) Following a similar procedure to that described in example 1 but using 2-bromo-4-methylthiazole-5-carboxylic acid (obtained as described in Singh, *J.M. J.Med. Chem.* 1969, 12, 1553), (1R,2R)-2-bromo-N-[2-(2,4-difluorophenyl)-2-hydroxy-1-methyl-3-(1H-1,2,4-triazol-1-yl)propyl]-4-methyl-thiazole-5-carboxamide was obtained as a white solid: mp 155°–163° C.; $^1$H NMR (300 MHz, CDCl$_3$) δ (TMS) 7.81 (s, 1H, triazole), 7.78 (s, 1H, triazole), 7.35 (dt, J$_d$=6.5, J$_t$=8.8, 1H, arom), 6.8–6.6 (m, 2H, arom), 6.36 (br d, J=9.5, 1H, NH), 5.4 (br s, 1H, OH), 5.00 (d, J=14.2, 1H, TrCH(H)), 4.90 (br quint, J=7, 1H, CHMe), 4.46 (d, J=14.2, 1H, TrCH(H)), 2.74 (s, 3H, Me-thiazole), 0.99 (d, J=6.8, 3H, MeCH); [α]$^D$=−97.8° (c 1, CHCl$_3$). Analysis calculated for C$_{17}$H$_{16}$BrF$_2$N$_5$O$_2$S: C 43.23; H 3.41; N 14.83: S 6.79. Found: C 43.23; H 3.64; N 14.58; S 6.29.

(b) To a solution of the product obtained in section (a) (375 mg, 0.79 mmol) in N-methylpyrrolidone (5 mL) was added 4-chlorophenol (117 mg, 0.91 mmol) and anhydrous K$_2$CO$_3$ (109 mg, 0.79 mmol). The mixture was stirred at 130° C. for 18 h and then water and EtOAc were added. The organic phase was separated and the aqueous residue was extracted with EtOAc. The combined organic extracts were dried over Na$_2$SO$_4$, concentrated and purified by flash chromatography to give the title compound as an amorphous solid (159 mg): $^1$H NMR (300 MHz, CDCl$_3$) δ (TMS) 7.80 (s, 1H, triazole), 7.77 (s, 1H, triazole), 7.41 (d, J=9, 2H, arom), 7.36 (dt, J$_d$=6.5, J$_t$=8.8, 1H, arom), 7.25 (d, J=9, 2H, arom), 6.8–6.6 (m, 2H, arom), 6.20 (br d, J=9.5, 1H, NH), 5.33 (d, J=1.5, 1H, OH), 5.00 (d, J=14.2, 1H, TrCH(H)), 4.91 (br quint, J=7, 1H, CHMe), 4.46 (d, J=14.2, 1H, TrCH(H)), 2.62 (s, 3H, Me-thiazole), 0.98 (d, J=6.8, 3H, MeCH); GC—MS 295 and 297 (ethylaminoacyl group, C$_{13}$H$_{12}$ClN$_2$O$_2$S), 252 and 254 (acyl group, C$_{11}$H$_7$ClNO$_2$S), 224 (Tr—CH$_2$COHAr, C$_{10}$H$_8$F$_2$N$_3$O); [α]$^D$=−93° (c 1, CHCl$_3$).

EXAMPLE 42

(1R,2R)-2-(4-Chlorobenzenesulfonyl)-N-[2-(2,4-difluorophenyl)-2-hydroxy-1-methyl-3-(1H-1,2,4-triazol-1-yl)propyl]-4-methylthiazole-5-carboxamide Following the procedure described in example 41 but using the sodium salt of 4-chlorobenzenesulfinic acid (obtained as described in *Org.Synth.Coll.Vol IV*, 674, from 4-chlorobenzenesulfonyl chloride and sodium sulfite) instead of the mixture of 4-chlorophenol and K$_2$CO$_3$, the title compound was obtained as a white amorphous solid: $^1$H NMR (300 MHz, CDCl$_3$) δ (TMS) 8.04 (dt, J$_t$=1.9, J$_d$=8.7, 2H, arom), 7.81 (s, 1H, triazole), 7.76 (s, 1H, triazole), 7.56 (dt, J$_t$=1.9, J$_d$=8.7, 2H, arom), 7.34 (dt, J$_d$=6.5, J$_t$=8.8, 1H, arom), 6.8–6.6 (m, 2H, arom), 6.20 (br d, J=9.5, 1H, NH), 5.41 (d, J=1.5, 1H, OH), 4.97 (d, J=14.2, 1H, TrCH(H)), 4.86 (br quint, J=7, 1H, CHMe), 4.42 (d, J=14.2, 1H, TrCH(H)), 2.74 (s, 3H, Me-thiazole), 0.99 (d, J=6.8, 3H, MeCH);GC—MS 343 and 345 (ethylaminoacyl group, C$_{13}$H$_{12}$ClN$_2$O$_3$S$_2$), 300 and 302 (acyl group, C$_{11}$H$_7$ClNO$_3$S$_2$), 224 (Tr—CH$_2$COHAr, C$_{10}$H$_8$F$_2$N$_3$O).

EXAMPLE 43

(1R,2R)-5-(4-Chlorophenyl)-N-[2-(2,4-difluorophenyl)-2-hydroxy-1-m ethyl-3-(1H-1,2,4-triazol-1-yl)propyl]-2-methylfuran-3-carboxamide Following a similar procedure to that described in example 1 but using 5-(4-chlorophenyl)-2-methylfuran-3-carboxylic acid the title compound was obtained as a white solid: mp 189°–190° C.; $^1$H NMR (300 MHz, CDCl$_3$) δ (TMS) 7.80 (s, 1H, triazole), 7.79 (s, 1H, triazole), 7.59 (dt, J$_t$=2, J$_d$=8.4, 2H, arom), 7.39 (dt, J$_d$=6.5, J$_t$=8.8, 1H, arom), 7.37 (dt, J$_t$=2, J$_d$=8.4, 2H, arom), 6.8–6.6 (m, 2H, arom), 6.27 (s, 1H, furan), 6.29 (br d, J=9.5, 1H, NH), 5.35 (s, 1H, OH), 5.04 (d, J=14.2, 1H, TrCH(H)), 4.93 (br quint, J=7, 1H, CHMe), 4.51 (d, J=14.2, 1H, TrCH(H)), 2.71 (s, 3H, Me-furan), 1.01 (d, J=6.8, 3H, MeCH); HPLC-MS 262 and 264 (ethylaminoacyl group, C$_{14}$H$_{13}$ClNO$_2$), 219 and 221 (acyl group, C$_{12}$H$_8$ClO$_2$), 224 (Tr—CH$_2$COHAr, C$_{10}$H$_8$F$_2$N$_3$O); [α]$^D$=−131.2° (c 1, CHCl$_3$). Analysis calculated for C$_{24}$H$_{21}$ClF$_2$N$_4$O$_3$: C 59.20; H 4.35; N 11.51. Found: C 59.22; H 4.34; N 11.58.

EXAMPLE 44

(1R,2R)-5-(4-Chlorophenyl)-N-[2-(2,4-difluorophenyl)-2-hydroxy-1-methyl-3-(1H-1,2,4-triazol-1-yl)propyl]-2-trifluoromethylfuran-3-carboxamide Following a similar procedure to that described in example 1 but using 5-(4-chlorophenyl)-2-trifluoromethylfuran-3-carboxylic acid the title compound was obtained as a white amorphous solid: $^1$H NMR (300 MHz, CDCl$_3$) δ (TMS) 7.81 (s, 1H, triazole), 7.78 (s, 1H, triazole), 7.66 (dt, J$_t$=2, J$_d$=8.4, 2H, arom), 7.43 (dt, J$_t$=2, J$_d$=8.4, 2H, arom), 7.36 (dt, J$_d$=6.5, J$_t$=8.8, 1H, arom), 6.98 (s, 1H, furan), 6.8–6.6 (m, 2H, arom), 6.60 (br d, J=9.3, 1H, NH), 5.34 (s, 1H, OH), 5.03 (d, J=14.2, 1H, TrCH(H)), 4.93 (br quint, J=7, 1H, CHMe), 4.50 (d, J=14.2, 1H, TrCH(H)), 1.00 (d, J=6.8, 3H, MeCH); GC/MS 316 and 318 (ethylaminoacyl group, C$_{14}$H$_{10}$ClF$_3$NO$_2$), 273 and 275 (acyl group, C$_{12}$H$_5$ClF$_3$O$_2$), 224 (Tr—CH$_2$COHAr, C$_{10}$H$_8$F$_2$N$_3$O); [α]$^P$=−84.6° (c 1, CHCl$_3$). Analysis calculated for C$_{24}$H$_{18}$ClF$_5$N$_4$O$_3$: C 53.30; H 3.35; N 10.36. Found: C 53.12; H 3.82; N 10.36.

EXAMPLE 45

(1R,2R)-2-(4-Chlorophenyl)-N-[2-(2,4-difluorophenyl)-2-hydroxy-1-methyl-3-(1H-1,2,4-triazol-1-yl)propyl]-4-methyloxazole-5-carboxamide A solution of N-(4-chlorobenzoyl)-L-alanine (1.46 g, 6.41 mmol) in benzene (35 mL) was treated with oxalyl chloride (0.55 mL, 6.41 mmol) at 45° C. for 3 h. Next, a solution of (2R,3R)-3-amino-2-(2,4-difluorophenyl)-1-(1H-1,2,4-triazol-1-yl)-2-butanol (1.72 g, 6.41 mmol) and triethylamine (2.2 mL) in CHCl$_2$ (20 mL) was slowly added and the reaction mixture was stirred at 0° C. for 0.5 h. The crude product was then poured into cold water and extracted with CHCl$_3$. The organic solution was dried over Na$_2$SO$_4$, filtered and the filtrate was concentrated in vacuo to give a mixture of several products (TLC) from which the title compound was isolated by flash chromatography as a white solid (140 mg): mp 89°–93° C.; $^1$H NMR (300 MHz, CDCl$_3$) δ (TMS) 8.04 (d, J=8.5, 2H, arom), 7.79 (s, 1H, triazole), 7.78 (s, 1H, triazole), 7.49 (d, J=8.5, 2H, arom), 7.37 (dt, J$_d$=6.5, J$_t$=8.8, 1H, arom), 6.8–6.6 (m, 3H, arom, NH), 5.38 (d, J=1.1, 1H, OH), 5.04 (d, J=14.3, 1H, TrCH(H)), 4.96 (br quint, J=7, 1H, CHMe), 4.53 (d, J=14.3, 1H, TrCH(H)), 2.60 (s, 3H, Me-oxazole), 1.04 (d, J=6.8, 3H, MeCH); HPLC-MS 263 and 265 (ethylaminoacyl group, C$_{13}$H$_{12}$ClN$_2$O$_2$), 220 and 222 (acyl group, C$_{11}$H$_7$ClNO$_2$), 224 (Tr—CH$_2$COHAr, C$_{10}$H$_8$F$_2$N$_3$O); [α]$^P$=−141° (c 0.5, CHCl$_3$). Analysis calculated for C$_{23}$H$_{20}$ClF$_2$N$_5$O$_3$: C 56.62; H 4.13; N 14.35. Found: C 56.41; H 4.19; N 14.50.

EXAMPLE 46

(1R,2R)-2-(4-Chlorophenyl)-N-[2-(2,4-difluorophenyl)-2-hydroxy-1-methyl-3-(1H-1,2,4-triazol-1-yl)propyl]-thiazole-4-carboxamide Following a similar procedure to that described in example 1 but using 2-(4-chlorophenyl)thiazole-4-carboxylic acid (reference example 31) the title compound was obtained as a white solid: mp 201°–204° C.; $^1$H NMR (80 MHz, CDCl$_3$) δ (TMS) 8.15 (s, 1H, thiazole), 8.0–7.7 (m, 4H, triazole, arom), 7.6–7.2 (3H, arom), 7.0–6.6 (m, 2H, arom), 5.33 (d, J=1.3, 1H, OH), 5.06 (d, J=14.5, 1H, TrCH(H)), 5.1–4.8 (m, 1H, CHMe), 4.5 (d, J=14.5, 1H, TrCH(H)), 1.07 (d, J=7, 3H, MeCH); [α]$^P$=−130.7° (c 1, CHCl$_3$). Analysis calculated for C$_{22}$H$_{18}$ClF$_2$N$_5$O$_2$S: C 53.94; H 3.70; N 14.29; S 6.54. Found: C 54.03; H 4.05; N 13.85; S 6.51.

EXAMPLE 47

(1R,2R)-N-[2-(2,4-Difluorophenyl)-2-hydroxy-1-methyl-3-(-1,2,4-triazol-1-yl)propyl]-2-(4-trifluoromethylphenyl)thiazole-4-carboxamide Following a similar procedure to that described in example 1 but using 2-(4-trifluoromethylphenyl)thiazole-4-carboxylic acid (reference example 32) the title compound was obtained as a white solid: mp 167°–168° C.; $^1$H NMR (80 MHz, CDCl$_3$) δ (TMS) 8.21 (s), 8.16 (s), 8.07 (s), 8.1–7.6 (m, arom), 7.6–7.3 (1H, arom), 7.0–6.6 (m, 2H, arom), 5.34 (d, J=1.3, 1H, OH), 5.06 (d, J=14.5, 1H, TrCH(H)), 5.1–4.8 (m, 1H, CHMe), 4.5 (d, J=14.5, 1H, TrCH(H)), 1.08 (d, J=7, 3H, MeCH); [α]$^P$=−136.7° (c 1, CHCl$_3$). Analysis calculated for C$_{23}$H$_{18}$F$_5$N$_5$O$_2$S: C 52.77; H 3.47; N 13.38; S 6.12. Found: C 52.92; H 3.47; N 13.42; S 6.08.

EXAMPLE 48

(1R,2R)-N-[2-(2,4-Difluorophenyl)-2-hydroxy-1-methyl-3-(1H-1,2,4-triazol-1-yl)propyl]-2-phenylthiazole-4-carboxamide Following a similar procedure to that described in example 1 but using 2-phenylthiazole-4-carboxylic acid (reference example 33) the title compound was obtained as a white solid: mp 174°–175° C;. $^1$H NMR (80 MHz, CDCl$_3$) δ (TMS) 8.15 (s), 8.1–7.9 (m, arom), 7.81 (s), 7.75 (s), 7.6–7.3 (m, 4H, arom), 7.0–6.6 (m, 2H, arom), 5.35 (d, J=1.3, 1H, OH), 5.06 (d, J=14.5, 1H, TrCH(H)), 5.1–4.8 (m, 1H, CHMe), 4.5 (d, J=14.5, 1H, TrCH(H)), 1.08 (d, J=7, 3H, MeCH); [α]$^P$=−145.5° (c 1, CHCl$_3$). Analysis calculated for C$_{22}$H$_{19}$F$_2$N$_5$O$_2$S: C 58.01; H 4.20; N 15.38; S 7.04. Found: C 58.11; H 4.59; N 15.34; S 6.85.

EXAMPLE 49

(1R,2R)-N-[2-(2,4-Difluorophenyl)-2-hydroxy-1-methyl-3-(1H-1,2,4-triazol-1-yl)propyl]-2-[4-(2,2,3,3-tetrafluoropropoxy)phenyl]thiazole-4-carboxamide Following a similar procedure to that described in example 1 but using 2-[4-(2,2,3,3-tetrafluoropropoxy)phenyl]thiazole-4-carboxylic acid (reference example 34) the title compound was obtained as an amorphous solid: $^1$H NMR (80 MHz, CDCl$_3$) δ (TMS) 8.10 (s), 8.1–7.8 (m, arom), 7.6–7.4 (m, 1H, arom), 7.2–6.7 (m, 2+¼H, arom, CHF$_2$), 6.07 (t, J=4.3, ½H, CHF$_2$), 5.41 (t, J=4.3, ¼H, CHF$_2$), 5.34 (d, J=1.3, 1H, OH), 5.06 (d, J=14.5, 1H, TrCH(H)), 5.1–4.8 (m, 1H, CHMe), 4.5 (d, J=14.5, 1H, TrCH(H)), 4.44 (tt, J=0.8, J=12, 2H, OCH$_2$),1.07 (d, J=7, 3H, MeCH); [α]$^P$=−123.8° (c 1, CHCl$_3$). Analysis calculated for C$_{25}$H$_{21}$F$_6$N$_5$O$_3$S: C 51.28; H 3.62; N 11.96; S 5.48. Found: C 50.89; H 3.90; N 11.34; S 5.34.

EXAMPLE 50

(1R,2R)-N-[2-(2,4-Difluorophenyl)-2-hydroxy-1-methyl-3-(1H-1,2,4-triazol-1-yl)propyl]-2-(3-pyridyl)thiazole-4-carboxamide Following a similar procedure to that described in example 1 but using 2-(3-pyridyl)thiazole-4-carboxylic acid the title compound was obtained as a white solid: mp 182°–183° C.; $^1$H NMR (80 MHz, CDCl$_3$) δ (TMS) 9.23 (br s, 1H, pyridine), 8.7 (br s, 1H, pyridine), 8.34 (br s, ½H, pyridine), 8.21 (s, 1.5H, thiazole, pyridine), 8.1–7.7 (m, triazole), 7.6–7.3 (m, 2H, arom, pyridine), 7.0–6.6 (m, 2H, arom), 5.34 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 1.08 (d, J=7, 3H, MeCH); [α]$^P$=−151.30 (c 1, CHCl$_3$). Analysis calculated for C$_{21}$H$_{18}$F$_2$N$_6$O$_2$S: C 55.26; H 3.97; N 18.41; S 7.02 Found: C 55.14; H 3.93; N 18.41; S 6.81.

EXAMPLE 51

(1R,2R)-5-(4-Chlorophenyl)-N-[2-(2,4-difluorophenyl)-2-hydroxy-1-methyl-3-(1H-1,2,4-triazol-1-yl)propyl]thiophene-2-carboxamide Following a similar procedure to that described in example 1 but using 5-(4-chlorophenyl)thiophene-2- carboxylic acid (prepared as described in Hauptmann et al, *Tetrahedron Lett.* 1968, 1317) the title compound was obtained as a white solid: mp 169°–170° C.; $^1$H NMR (300 MHz, CDCl$_3$) δ (TMS) 7.79 (s, 1H, triazole), 7.78 (s, 1H, triazole), 7.55 (dt, J$_t$=2.5, J$_d$=6.6, 2H, arom), 7.54 (d, J=3.5, 1H, thiophene), 7.38 (dt, J$_d$=6.5, J$_t$=8.8, 1H, arom), 7.38 (dt, J$_t$=2.5, J$_d$=6.6, 2H, arom), 7.25 (d, J=3.5, 1H, thiophene), 6.8–6.6 (m, 2H, arom), 6.53 (br d, J=9.5, 1H, NH), 5.35 (d, J=1.5, 1H, OH), 5.04 (d, J=14.3, 1H, TrCH(H)), 4.93 (br quint, J=7, 1H, CHMe), 4.51 (d, J=14.3, 1H, TrCH(H)), 1.02 (d, J=6.8, 3H MECH); MS 264 and 266 (ethylaminoacyl group, C$_{13}$H$_{11}$ClNOS), 221 and 223 (acyl group, C$_{11}$H$_6$ClOS), 224 (Tr—CH$_2$COHAr, ClOH$_8$F$_2$N$_3$O); [α]$^D$= –401.0° (c 1, CHCl$_3$). Analysis calculated for C$_{23}$H$_{19}$ClF$_2$N$_4$O$_2$S: C 56.50 H 3.92; N 11.46; S 6.56. Found: C 56.52; H 3.93; N 11.39; S 6.11.

EXAMPLE 52

(1R,2R)-5-(4-Cyanophenyl)-N-[2-(2,4-difluorophenyl)-2-hydroxy-1-methyl-3-(1H-1,2,4-triazol-1-yl)propyl]thiophene-2-carboxamide Following a similar procedure to that described in example 1 but using 5-(4-cyanophenyl)thiophene-2-carboxylic acid (reference example 35) the title compound was obtained as a white solid: mp 210°–211° C.; $^1$H NMR (300 MHz, CDCl$_3$) δ (TMS) 7.80 (s, 1H, triazole), 7.79 (s, 1H, triazole), 7.71 (d, J=8, 1H, arom), 7.70 (d, J=8, 2H, arom), 7.58 (d, J=3.9, 1H, thiophene), 7.41 (d, J=3.9, 1H, thiophene), 7.39 (dt, J$_d$=6.5, J$_t$=8.8, 1H, arom), 6.8–6.6 (m, 2H, arom), 6.57 (br d, J=9.4, 1H, NH), 5.37 (d, J=1.5, 1H, OH), 5.05 (d, J=14.3, 1H, TrCH(H)), 4.94 (br quint, J=7, 1H, CHMe), 4.52 (d, J=14.3, 1H, TrCH(H)), 1.03 (d, J=6.8, 3H, MeCH); HPLC-MS 212 (acyl group, C$_{12}$H$_6$NOS), 224 (Tr—CH$_2$COHAr, C$_{10}$H$_8$F$_2$N$_3$O); [α]$^D$=–105.6° (c 1, CHCl$_3$). Analysis calculated for C$_{24}$H$_{19}$F$_2$N$_5$O$_2$S: C 60.12 H 3.99; N 14.61; S 6.69. Found: C 58.98; H 3.90; N 14.26; S 6.28.

EXAMPLE 53

(1R,2R)-N-[2-(2,4-Difluorophenyl)-2-hydroxy-1-methyl-3-(1H-1,2,4-triazol-1-yl)propyl]-5-(2-pyridyl)thiophene-2-carboxamide Following a similar procedure to that described in example 1 but using 5-(2-pyridyl)thiophene-2-carboxylic acid the title compound was obtained as a white solid: mp 212°–213° C.; $^1$H NMR (80 MHz, CDCl$_3$) δ (TMS) 8.60 (dt, J$_t$=1, 1J$_t$=5, 1H, arom), 7.9–7.5 (m, arom), 7.5–7.2 (m, arom), 6.9–6.5 (m, arom, NH), 5.34 (d, J=1.3, 1H, OH), 5.05 (d, J=14.5, 1H, TrCH(H)), 5.1–4.8 (m, 1H, CHMe), 4.50 (d, J=14.5, 1H, TrCH(H)), 1.02 (d, J=7, 3H, MeCH); [α]$^D$=–116.8° (c 1, CHCl$_3$). Analysis calculated for C$_{22}$H$_{19}$F$_2$N$_5$O$_2$S: C 58.01; H 4.20; N 15.38; S 7.04. Found: C 58.20; H 4.55; N 15.82; S 6.85.

EXAMPLE 54

(1R,2R)-N-[2-(2,4-Difluorophenyl)-2-hydroxy-1-methyl-3-(1H-1,2,4-triazol-1-yl)propyl]-5-[1-methyl-3-trifluoromethyl-1H-pyrazol-5-yl]thiophene-2-carboxamide Following a similar procedure to that described in example 1 but using 5-[1-methyl-3-trifluoromethyl-1H-pyrazol-5-yl]thiophene-2-carboxylic acid the title compound was obtained as a white solid: mp 106°–110° C; $^1$H NMR (300 MHz, CDCl$_3$) δ (TMS) 7.79 (s, 1H, triazole), 7.77 (s, 1H, triazole), 7.54 (d, J=3.8, 1H, thiophene), 7.38 (dt, J$_d$=6.5, J$_t$=8.8, 1H, arom), 7.30 (d, J=3.8, 1H, thiophene), 6.84 (s, 1H, pyrazole), 6.8–6.6 (m, 2H, arom), 6.52 (br d, J=9.3, 1H, NH), 5.34 (d, J=1.5, 1H, OH), 5.03 (d, J=14.3, 1H, TrCH(H)), 4.93 (br quint, J=7, 1H, CHMe), 4.52 (d, J=14.3, 1H, TrCH(H)), 4.03 (s, 3H, Me-pyrazole), 1.01 (d, J=6.8, 3H, MeCH); MS 302 (ethylaminoacyl group, C$_{12}$H$_{11}$F$_3$N$_3$OS), 259 (acyl group, C$_{10}$H$_6$F$_3$N$_2$O$_5$), 224 (Tr—CH$_2$COHAr, C$_{10}$H$_8$F$_2$N$_3$O); [α]$^D$=–90.1° (c 1, CHCl$_3$). Analysis calculated for C$_{22}$H$_{19}$F$_5$N$_6$O$_2$S: C 50.19; H 3.64; N 15.96; S 6.09. Found: C 50.27; H 3.77; N 15.71; S 5.58.

EXAMPLE 55

(1R,2R)-5-(4-Chlorophenyl)-N-[2-(2,4-difluorophenyl)-2-hydroxy-1-methyl-3-(1H-1,2,4-triazol-1-yl)propyl]-3-methylthiophene-2-carboxamide Following a similar procedure to that described in example 1 but using 5-(4-chlorophenyl)-3-methylthiophene-2-carboxylic acid (reference example 36) the title compound was obtained as an amorphous solid: $^1$H NMR (300 MHz, CDCl$_3$) δ (TMS) 7.84 (s, 1H, triazole), 7.82 (s, 1H, triazole), 7.56 (dt, J$_t$=2.5, J$_d$=6.6, 2H, arom), 7.40 (dt, J$_d$=6.5, J$_t$=8.8, 1H, arom), 7.39 (d, J=7, 2H, arom), 7.14 (s, 1H, thiophene), 6.8–6.6 (m, 2H, arom), 6.42 (br d, J=9.3, 1H, NH), 5.38 (br s, 1H, OH), 5.08 (d, J=14.5, 1H, TrCH(H)), 4.95 (br quint, J=7, 1H, CHMe), 4.55 (d, J=14.5, 1H, TrCH(H)), 2.82 (s, 3H, Me-thiophene), 1.04 (d, J=6.8, 3H, MeCH); MS 278 and 280 (ethylaminoacyl group, C$_{14}$H$_{13}$ClNOS), 235 and 237 (acyl group, C$_{12}$H$_8$ClOS), 224 (Tr—CH$_2$COHAr, C$_{10}$H$_8$F$_2$N$_3$O); [α]$^D$=–114.9° (c 1, CHCl$_3$). Analysis calculated for C$_{24}$H$_{21}$ClF$_2$N$_4$O$_2$S: C 57.31 H 4.21; N 11.14; S 6.37. Found: C 57.39; H 4.21; N 11.21; S 6.59.

EXAMPLE 56

(1R,2R)-N-[2-(2,4-Difluorophenyl)-2-hydroxy-1-methyl-3-(1H-1,2,4-triazol-1-yl)propyl]-3-methyl-5-(4-trifluoromethylphenyl)thiophene-2-carboxamide Following a similar procedure to that described in example 1 but using 3-methyl-5-(4-trifluoromethylphenyl)thiophene-2-carboxylic acid (obtained by a similar procedure to that described in reference example 36) the title compound was obtained as an amorphous solid: MS 312 (ethylaminoacyl group, C$_{15}$H$_{13}$F$_3$NOS), 269 (acyl group, C$_{13}$H$_9$F$_3$OS), 224 (Tr—CH$_2$COHAr, C$_{10}$H$_8$F$_2$N$_3$O); [α]$^D$=–104.20 (c 1, CHCl$_3$). Analysis calculated for C$_{25}$H$_{21}$F$_5$N$_4$O$_2$S: C 55.97 H 3.95; N 10.44; S 5.98. Found: C 56.27; H 4.00; N 10.58; S 5.77.

EXAMPLE 57

(1R,2R)-5-(4-Cyanophenyl)-N-[2-(2,4-difluorophenyl)-2-hydroxy-1-methyl-3-(1H-1,2,4-triazol-1-yl)propyl]-3-methylthiophene-2-carboxamide Following a similar procedure to that described in example 1 but using 5-(4-cyanophenyl)-3-methylthiophene-2-carboxylic acid (reference example 37) the title compound was obtained as a white solid: mp 176°–177° C.; $^1$H NMR (300 MHz, CDCl$_3$) δ (TMS) 7.79 (s, 1H, triazole), 7.78 (s, 1H, triazole), 7.69 (s, 4H, arom), 7.39 (dt, J$_d$=6.5, J$_t$=8.8, 1H, arom), 7.23 (s, 1H, thiophene), 6.9–6.6 (m, 2H, arom), 6.43

(br d, J=9.4, 1H, NH), 5.35 (d, J=1.3, 1H, OH), 5.04 (d, J=14.2, 1H, TrCH(H)), 4.93 (br quint, J=7, 1H, CHMe), 4.52 (d, J=14.2, 1H, TrCH(H)), 2.60 (s, 3H, Me-thiophene), 1.02 (d, J=6.8, 3H, MeCH); GC/MS 269 (ethylaminoacyl group, $C_{15}H_{13}N_2OS$), 226 (acyl group, $C_{13}H_8NOS$), 224 (Tr—$CH_2COHAr$, $C_{10}H_8F_2N_3O$); $[\alpha]^D=-116.3°$ (c 1, $CHCl_3$). Analysis calculated for $C_{25}H_{21}F_2N_5O_2S$: C 60.84 H 4.29; N 14.19; S 6.50. Found: C 60.54; H 4.25; N 13.81; S 5.90.

EXAMPLE 58

(1R,2R)-3-Amino-5-(4-chlorophenyl)-N-[2-(2,4-difluorophenyl)-2-hydroxy-1-methyl-3-(1H-1,2,4-triazol-1-yl)propyl]thiophene-2-carboxamide Following a similar procedure to that described in example 1 but using 3-amino-5-(4-chlorophenyl)thiophene-2-carboxylic acid (obtained as described in Hartmann, *Synthesis* 1984, 275) the title compound was obtained as a yellow solid: mp 107°–111° C.; $^1H$ NMR (300 MHz, $CDCl_3$) δ (TMS) 7.79 (s, 2H, triazole), 7.61 (dt, $J_r=2$, $J_d=9$, 2H, arom), 7.39 (dt, $J_d=6.5$, $J_r=8.8$, 1H, arom), 7.37 (dt, $J_r=2$, $J_d=9$, 2H, arom), 6.9–6.6 (m, 2H, arom), 6.78 (s, 1H, thiophene), 5.93 (br d, J=9.3, 1H, NH), 5.69 (br s, 2H, $NH_2$), 5.35 (d, J=1.3, 1H, OH), 5.02 (d, J=14.3, 1H, TrCH(H)), 4.88 (br quint, J=7, 1H, CHMe), 4.52 (d, J=14.3, 1H, TrCH(H)), 1.01 (d, J=6.8, 3H, MeCH); HPLC-MS 279 and 281 (ethylaminoacyl group, $C_{13}H_{12}ClN_2OS$), 236 (acyl group, $C_{11}H_7ClNOS$); $[\alpha]^D=-137.8°$ (c 1, $CHCl_3$). Analysis calculated for $C_{23}H_{20}ClF_2N_5O_2S$: C 54.82; H 4.00; N 13.90; S 6.36. 2 5 Found: C 55.42; H 4.19; N 13.34; S 5.35.

EXAMPLE 59

(1R,2R)-3-Amino-4-[(4-chlorophenyl)sulfonyl]-N-[2-(2,4-difluorophenyl)-2-hydroxy-1-methyl-3-(1H-1,2,4-triazol-1-yl)propyl]thiophene-2-carboxamide Following a similar procedure to that described in example 1 but using 3-amino-4-[(4-chlorophenyl)sulfonyl] thiophene-2-carboxylic acid the title compound was obtained as a hygroscopic amorphous solid: $^1H$ NMR (80 MHz, $CDCl_3$) δ (TMS) 8.1–7.7 (m, arom), 7.9–7.5 (m, arom), 7.6–7.3 (m, arom), 6.9–6.5 (m, arom, $NH_2$), 6.00 (br d, J=9.5, 1H, NH), 5.31 (d, J=1.5, 1H, OH), 4.95 (d, J=14.5, 1H, TrCH(H)), 5.1–4.8 (m, 1H, CHMe), 4.44 (d, J=14.5, 1H, TrCH(H)), 0.96 (d, J=7, 3H, MeCH); $[\alpha]^D=-59.20$ (c 1, $CHCl_3$). Analysis calculated for $C_{23}H_{20}ClF_2N_5O_4S_2$: C 48.64 H 3.55; N 12.33; S 11.29. Found: C 48.27; H 3.91; N 12.60; S 10.65.

EXAMPLE 60

(1R,2R)-4-[(4-Chlorophenyl)sulfonyl]-N-[2-(2,4-difluorophenyl)-2-hydroxy-1-methyl-3-(1H-1,2,4-triazol-1-yl)propyl]-3-methylthiophene-2-carboxamide Following a similar procedure to that described in example 1 but using 4-[(4-chlorophenyl)sulfonyl]-3-methylthiophene-2-carboxylic acid the title compound was obtained as a white amorphous solid: $^1H$ NMR (80 MHz, $CDCl_3$) δ (TMS) 8.33 (s, 1H, thiophene), 7.85 (d, J=8.8, 2H, arom), 7.78 (s, 1H, triazole), 7.75 (s, 1H, triazole), 7.50 (d, J=8.8, 2H, arom), 7.41 (dt, $J_d=6.5$, $J_r=9$, 1H, arom), 6.9–6.6 (m, 2H, arom), 6.42 (br d, J=9.5, 1H, NH), 5.32 (d, J=1.5, 1H, OH), 4.99 (d, J=14.5, 1H, TrCH(H)), 5.1–4.8 (m, 1H, CHMe), 4.41 (d, J=14.5, 1H, TrCH(H)), 2.54 (s, 3H, Me-thiophene), 0.98 (d, J=7, 3H, MeCH); $[\alpha]^D=-73.8°$ (c 1, $CHCl_3$). Analysis calculated for $C_{24}H_{21}ClF_2N_4O_4S_2$: C 50.84 H 3.73; N 9.88; S 11.31. Found: C 51.23; H 4.12; N 9.67; S 10.62.

EXAMPLE 61

(1R,2R)-2-(4-Chlorophenyl)-N-[2-(2,4-difluorophenyl)-2-hydroxy-1-methyl-3-(1H-1,2,4-triazol-1-yl)propyl]-5-methyl-3H-imidazole-4-carboxamide Following a similar procedure to that described in example 1 but using 2-(4-chlorophenyl)-5-methyl-3H-imidazole-4-carboxylic acid (reference example 38) the title compound was obtained as a white solid: mp 165°–166° C.; $^1H$ NMR (300 MHz, $CDCl_3$) δ (TMS) 9.48 (br s, 1H, NH-imidazole), 7.81 (s, 1H, triazole), 7.78 (d, J=8.8, 2H, arom), 7.75 (s, 1H, triazole), 7.71 (d, J=9.6, 1H, NH), 7.43 (dt, $J_d=6.5$, $J_r=8.8$, 1H, arom), 7.42 (d, J=8.8, 2H, arom), 6.8–6.6 (m, 2H, arom), 5.38 (s, 1H, OH), 5.03 (d, J=14.3, 1H, TrCH(H)), 4.85 (br quint, J=7, 1H, CHMe), 4.60 (d, J=14.3, 1H, TrCH(H)), 2.68 (s, 3H, Me-imidazole), 1.07 (d, J=6.8, 3H, MeCH); HPLC-MS 262 and 264 (ethylaminoacyl group, $C_{13}H_{13}ClN_3O$), 219 (acyl group, $C_{11}H_8ClN_2O$); $[\alpha]^D=-105.9°$ (c 1, MeOH). Analysis calculated for $C_{23}H_{21}ClF_2N_6O_2$: C 56.74; H 4.35; N 17.26. Found: C 54.48; H 4.05; N 16.09.

EXAMPLE 62

(1R,2R)-2-(4-Chlorophenyl)-N-[2-(2,4-difluorophenyl)-2-hydroxy-1-methyl-3-(1H-1,2,4-triazol-1-yl)propyl]-3,5-dimethyl-3H-imidazole-4-carboxamide Following a similar procedure to that described in example 1 but using the mixture of acids obtained in reference example 39 (2-(4-chlorophenyl)-3,5-dimethyl-3H-imidazole-4-carboxylic acid and 2-(4-chlorophenyl)-1,5-dimethyl-1H-imidazole-4-carboxylic acid) two products were obtained, which were easily separated by flash chromatography. The less polar product (TLC in EtOAc) was identified by NOE as the title compound and was isolated as a white amorphous solid: $^1H$ NMR (300 MHz, $CDCl_3$) δ (TMS) 7.81 (s, 1H, triazole), 7.78 (s, 1H, triazole), 7.55 (d, J=8.5, 2H, arom), 7.45 (d, J=8.5, 2H, arom), 7.40 (dt, $J_d=6.5$, $J_r=8.8$, 1H, arom), 6.8–6.6 (m, 2H, arom), 6.39 (d, J=9.5, 1, NH), 5.37 (d, J=1.5, 1H, OH), 5.05 (d, J=14.3, 1H, TrCH(H)), 4.96 (br quint, J=7, 1H, CHMe), 4.53 (d, J=14.3, 1H, TrCH(H)), 3.87 (s, 3H, N-Me), 2.61 (s, 3H, Me-imidazol), 1.03 (d, J=6.8, 3H, MeCH); GC/MS 276 and 278 (ethylaminoacyl group, $C_{14}H_{15}ClN_3O$), 198 and 200 (acyl group, $C_{12}H_{10}N_2O$), 224 (Tr—$CH_2COHAr$, $C_{10}H_8F_2N_3O$); $[\alpha]^D=-71.4°$ (c 1, $CHCl_3$). Analysis calculated for $C_{24}H_{23}ClF_2N_6O_2 \cdot H_2O$: C 55.55; H 4.86; N 16.19. Found: C 55.11; H 4.75; N 15.93.

EXAMPLE 63

(1R,2R)-2-(4-Chlorophenyl)-N-[2-(2,4-difluorophenyl)-2-hydroxy-1-methyl-3-(1H-1,2,4-triazol-1-yl)propyl]-1,5-dimethyl-1H-imidazole-4-carboxamide In the flash chromatography of the preceding example a second more polar product also eluted, which was identified by NOE as the title compound and which was also obtained as a white amorphous solid: $^1H$ NMR (300 MHz, $CDCl_3$) δ (TMS) 7.81 (s, 1H, triazole), 7.73 (s, 1H, triazole), 7.68 (br d, J=9.4, 1H, NH), 7.57 (d, J=8.5, 2H, arom), 7.48 (d, J=8.5, 2H, arom), 7.40 (dt, $J_d$=6.5, $J_t$=8.8, 1H, arom), 6.8–6.6 (m, 2H, arom), 5.36 (d, J=1.5, 1H, OH), 5.03 (d, J=14.3, 1H, TrCH(H)), 4.83 (br quint, J=7, 1H, CHMe), 4.56 (d, J=14.3, 1H, TrCH(H)), 3.59 (s, 3H, N—Me), 2.68 (s, 3H, Me-imidazol), 1.04 (d, J=6.8, 3H, MeCH); GC/MS 276 and 278 (ethylaminoacyl group, $C_{14}H_{15}ClN_3O$), 198 and 200 (acyl group, $C_{12}H_{10}N_2O$), 224 (Tr—$CH_2COHAr$, $C_{10}H_8F_2N_3O$); $[\alpha]^D$=−108.7° (c 1, $CHCl_3$). Analysis calculated for $C_{24}H_{23}ClF_2N_6O_2 \cdot H_2O$: C 55.55; H 4.86; N 16.19. Found: C 55.68; H 4.94; N 15.75.

EXAMPLE 64

(1R,2R)-5-(4-Chlorophenyl)-N-[2-(2,4-difluorophenyl)-2-hydroxy-1-methyl-3-(1H-1,2,4-triazol-1-yl)propyl]-1,3,4-oxadiazole-2-carboxamide, chloroform solvate Following a similar procedure to that described in example 1 but using 5-(4-chlorophenyl)-1,3,4-oxadiazole-2-carboxylic acid (reference example 40) and recrystallizing the final product from $CHCl_3$ the title compound was obtained as a white solid: mp 188°–190° C.; $^1$H NMR (300 MHz, MeOH—$d_4$) δ (MeOH—$d_4$) 8.24 (s, 1H, triazole), 7.9–7.8 (m, 2H, arom), 7.68 (s, 1H, triazole), 7.52 (dt, $J_t$=2, $J_d$=8.7, 2H, arom), 7.35 (dt, $J_d$=6.5, $J_t$=8.8, 1H, arom), 6.95 (ddd, J=2.4, J=8.7, J=11.5, 1H, arom), 6.81 (dt, $J_d$=2.0, $J_t$=8.0, 1H, arom), 4.88 (d, J=14.4, 1H, TrCH(H)), 4.82 (m, 1H, CHMe), 4.54 (d, J=14.4, 1H, TrCH(H)), 0.99 (d, J=6.8, 3H, MeCH); HPLC-MS 250 and 252 (ethylaminoacyl group, $C_{11}H_9ClN_3O_2$), 207 and 209 (acyl group, $C_9H_4ClN_3O_2$), 224 (Tr—$CH_2COHAr$, $C_{10}H_8F_2N_3O$); $[\alpha]^D$=−66.5° (c 1, MeOH).

EXAMPLE 65

(1R,2R)-3-(4-Chlorophenyl)-N-[2-(2,4-difluorophenyl)-2-hydroxy-1-methyl-3-(1H-1,2,4-triazol-1-yl)propyl]-1,2,4-oxadiazole-5-carboxamide Following a similar procedure to that described in example 1 but using 3-(4-chlorophenyl)-1,2,4-oxadiazole-5-carboxylic acid (reference example 41) the title compound was obtained as a white solid: mp 170°–172° C.; $^1$H NMR (300 MHz, $CDCl_3$) δ (TMS) 8.10 (dt, $J_t$=2, $J_d$=9, 2H, arom), 7.81 (s, 1H, triazole), 7.79 (s, 1H, triazole), 7.69 (br d, J=9.3, 1H, NH), 7.52 (dt, $J_t$=2, $J_d$=9, 2H, arom), 7.40 (dt, $J_d$=6.5, $J_t$=8.8, 1H, arom), 6.8–6.6 (m, 2H, arom), 5.46 (d, J=1.5, 1H, OH), 5.02 (d, J=14.2, 1H, TrCH(H)), 4.95 (br quint, J=7, 1H, CHMe), 4.52 (d, J=14.2, 1H, TrCH(H)), 1.07 (d, J=6.8, 3H, MeCH); HPLC-MS 250 and 252 (ethylaminoacyl group, $C_{11}H_9ClN_3O_2$), 207 and 209 (acyl group, $C_9H_4ClN_2O_2$), 224 (Tr—$CH_2COHAr$, $C_{10}H_8F_2N_3O$); $[\alpha]^D$=−81.8° (c 1, MeOH).

EXAMPLE 66

(1R,2R)-5(4-Chlorophenyl)-N-[2-(2,4-difluorophenyl)-2-hydroxy-1-methyl-3-(1H-1,2,4-triazol-1-yl)propyl]-1,2,4-oxadiazole-3-carboxamide Following a similar procedure to that described in example 1 but using 5-(4-chlorophenyl)-1,2,4-oxadiazole-3-carboxylic acid (reference example 42) the title compound was obtained as a white solid: mp 79°–83° C.; $^1$H NMR (300 MHz, $CDCl_3$) δ (TMS) 8.16 (dt, $J_t$=1.8, $J_d$=8.6, 2H, arom), 7.79 (br s, 2H, triazole), 7.60 (br d, J=9.3, 1H, NH), 7.56 (dt, $J_t$=1.8, $J_d$=8.6, 2H, arom), 7.40 (dt, $J_d$=6.5, $J_t$=8.8, 1H, arom), 6.8–6.6 (m, 2H, arom), 5.38 (d, J=1.5, 1H, OH), 5.04 (d, J=14.4, 1H, TrCH(H)), 4.95 (br quint, J=7, 1H, CHMe), 4.53 (d, J=14.4, 1H, TrCH(H)), 1.06 (d, J=6.8, 3H, MeCH); HPLC-MS 250 and 252 (ethylaminoacyl group, $C_{11}H_9ClN_3O_2$), 224 (Tr—$CH_2COHAr$, $C_{10}H_8F_2N_3O$); $[\alpha]^D$=−67.4° (c 1, MeOH).

EXAMPLE 67

(1R,2R)-3-(4-Chlorophenyl)-N-[2-(2,4-difluorophenyl)-2-hydroxy-1-methyl-3-(1H-1,2,4-triazol-1-yl)propyl]-1,2,4-thiadiazole-5-carboxamide Following a similar procedure to that described in example 1 but using 3-(4-chlorophenyl)-1,2,4-thiadiazole-5-carboxylic acid (prepared as described in Howe et al, *J. Org.Chem.* 1977, 42, 1813) the title compound was obtained as a white solid: mp 215°–220° C.; $^1$H NMR (300 MHz, MeOH—$d_4$) δ (MeOH—$d_4$) 8.45 (dt, $J_t$=2, $J_d$=7, 2H, arom), 8.32 (s, 1H, triazole), 7.75 (s, 1H, triazole), 7.65 (dt, $J_t$=2, $J_d$=7, 2H, arom), 7.50 (dt, $J_d$=6.5, $J_t$=8.8, 1H, arom), 7.08 (ddd, J=2.4, J=8.7, J=11.5, 1H, arom), 6.94 (dt, $J_d$=2.0, $J_t$=8.0, 1H, arom), 5.12 (q, J=6.8, 1H, CHMe), 5.05 (d, J=14.6, 1H, TrCH(H)), 4.70 (d, J=14.6, 1H, TrCH(H)), 1.18 (d, J=6.8, 3H, MeCH); HPLC-MS 266 and 268 (ethylaminoacyl group, $C_{11}H_9ClN_3OS$), 223 and 225 (acyl group, $C_9H_4ClN_2OS$), 224 (Tr—$CH_2COHAr$, $C_{10}H_8F_2N_3O$); $[\alpha]^D$=−106.3° (c 1, $HCl_3$).

EXAMPLE 68

(1R,2R)-5-(4-Chlorophenyl)-N-[2-(2,4-difluorophenyl)-2-hydroxy-1-methyl-3-(1H-1,2,4-triazol-1-yl)propyl]-1,2,4-thiadiazole-3-carboxamide Following a similar procedure to that described in example 1 but using 5-(4-chlorophenyl)-1,2,4-thiadiazole-3-carboxylic acid (prepared as described in Howe et al, *J.Org.Chem.* 1977, 42, 1813) the title compound was obtained as a white solid: mp 186°–187° C.; $^1$H NMR (300 MHz, MeOH—$d_4$) δ (MeOH) 8.32 (s, 1H, triazole), 8.22 (dt, $J_t$=2, $J_d$=8.4, 2H, arom), 7.76 (s, 1H, triazole), 7.70 (dt, $J_t$=2, $J_d$=8.4, 2H, arom), 7.49 (dt, $J_d$=6.5, $J_t$=8.8, 1H, arom), 7.08 (ddd, J=2.4, J=8.7, J=11.5, 1H, arom), 6.94 (dt, $J_d$=2.0, $J_t$=8.0, 1H, arom), 5.15 (q, J=6.8, 1H, CHMe), 5.05 (d, J=14.6, 1H, TrCH(H)), 4.70 (d, J=14.6, 1H, TrCH(H)), 1.17 (d, J=6.8, 3H, MeCH); HPLC-MS 266 and 268 (ethylaminoacyl group, $C_{11}H_9ClN_3OS$), 223 and 225 (acyl group, $C_9H_4ClN_2OS$), 224 (Tr—$CH_2COHAr$, $C_{10}H_8F_2N_3O$); $[\alpha]^D$=−80.80 (c 1, $CHCl_3$).

EXAMPLE 69

(1R,2R)-3-(2-Chloro-6-fluorophenyl)-N-[2-(2,4-difluorophenyl)-2-hydroxy-1-methyl-3-(1H-1,2,4-triazol-1-yl)propyl]-5-methylisoxazole-4-carboxamide Following a similar procedure to that described in example 1 but using 3-(2-chloro-6-fluorophenyl)-5-methylisoxazole-4-carboxylic acid the title compound was obtained as an amorphous solid: $^1$H NMR (80 MHz, $CDCl_3$) δ (TMS) 7.77 (s, 1H, triazole), 7.70 (s, 1H, triazole), 7.6–7.0 (m, 4H, arom), 6.9–6.5 (m, 2H, arom), 5.88 (br d, J=9, 1H, NH), 4.83 (d, J=14.5, 1H, TrCH(H)), 5.1–4.8 (m, 1H, CHMe), 4.17 (d, J=14.5, 1H, TrCH(H)), 2.83 (s, 3H, Me-isoxazole), 0.74 (d, J=6.6, 3H, MeCH); $[\alpha]^D$=−98.2° (c 1, $CHCl_3$). Analysis calculated for $C_{23}H_{19}ClF_3N_5O_3$: C 54.61; H 3.79; N 13.84. Found: C 55.38; H 4.02; N 13.76.

EXAMPLE 70

(1R,2R)-N-[2-(2,4-Difluorophenyl)-2-hydroxy-1-methyl-3-(1H-1,2,4-triazol-1-yl)propyl]4-(1,2,3-thiadiazol-4-yl)benzamide Following a similar procedure to that described in example 1 but using 4-(1,2,3-thiadiazol-4-yl)benzoic acid the title compound was obtained as a yellow solid: mp 196°–198° C.; $^1$H NMR (80 MHz, CDCl$_3$) δ (TMS) 8.76 (s, 1H, thiadiazole), 8.29 (d, J=8, 2H, arom), 7.98 (d, J=8, 2H, arom), 7.40 (dt, J$_d$=6.5, J$_t$=8.5, 1H, arom), 7.79 (s, 2H, triazole), 6.9–6.5 (m, 3H, arom, NH), 5.37 (br s, 1H, OH), 5.08 (d, J=14.5, 1H, TrCH(H)), 5.1–4.8 (m, 1H, CHMe), 4.50 (d, J=14.5, 1H, TrCH(H)), 1.06 (d, J=7, 3H, MeCH); [α]$^D$=–121.2° (c 1, CHCl$_3$). Analysis calculated for C$_{21}$H$_{18}$F$_2$N$_6$O$_2$S: C 55.26; H 3.97; N 18.41; S 7.02. Found: C 55.65; H 4.11; N 19.05; S 7.39.

EXAMPLE 71

(1R,2R)-5-(4-Chlorophenyl)-N-[2-(2,4-difluorophenyl)-2-hydroxy-1-methyl-3-(1H-1,2,4-triazol-1-yl)propyl]nicotinamide Following a similar procedure to that described in example 1 but using 5-(4-chlorophenyl)nicotinic acid the title compound was obtained: mp 93°–101° C.; $^1$H NMR (300 MHz, CDCl$_3$) δ (TMS) 9.02 (d, J=2.1, 1H, pyr), 8.96 (d, J=2.2, 1H, pyr), 8.33 (t, J=2.2, 1H, pyr), 7.8 (s, 1H, triazole), 7.79 (s, 1H, triazole), 7.58 (dt, J$_t$=2, J$_d$=8.7, 2H, arom), 7.49 (dt, J$_t$=2, J$_d$=8.7, 2H, arom), 7.39 (dt, J$_d$=6.5, J$_t$=8.8, 1H, arom), 6.8–6.6 (m, 3H, arom, NH), 5.41 (d, J=1.4, 1H, OH), 5.06 (d, J=14.2, 1H, TrCH(H)), 5.03 (br quint, J=7, 1H, CHMe), 4.50 (d, J=14.2, 1H, TrCH(H)), 1.06 (d, J=6.8, 3H, MeCH); GC/MS 259 and 261 (ethylaminoacyl group, C$_{14}$H$_{12}$ClN$_2$O), 216 and 218 (acyl group, C$_{12}$H$_7$ClNO), 224 (Tr—CH$_2$COHAr, C$_{10}$H$_8$F$_2$N$_3$O); [α]$^D$=–96.6° (c 1, CHCl$_3$).

EXAMPLE 72

(1R,2R)-3-(4-Chlorophenyl)-N-[2-(2,4-difluorophenyl)-2-hydroxy-1-methyl-3-(1H-1,2,4-triazol-1-yl)propyl]benzamide Following a similar procedure to that described in example 1 but using 3-(4-chlorophenyl)benzoic acid the title compound was obtained as a white solid: mp 90°–91° C.; $^1$H NMR (300 MHz, CDCl$_3$) δ (TMS) 8.05 (t, J=1.7, 1H, arom), 7.80 (dt, J$_t$=1.2, J$_d$=8.3, 1H, arom), 7.79 (s, 2H, triazole), 7.72 (dt, J$_t$=1.2, J$_d$=8.3, 1H, arom), 7.56 (dt, J$_t$=2, J$_d$=8.7, 2H, arom), 7.5–7.6 (m, 1H, arom), 7.44 (dt, J$_t$=2, J$_d$=8.7, 2H, arom), 7.39 (dt, J$_d$=6.5, J$_t$=8.8, 1H, arom), 6.8–6.6 (m, 3H, arom, NH), 5.36 (d, J=1.2, 1H, OH), 5.08 (d, J=14.2, 1H, TrCH(H)), 5.01 (br quint, J=7, 1H, CHMe), 4.50 (d, J=14.2, 1H, TrCH(H)), 1.05 (d, J=6.8, 3H, MeCH); CC/MS 258 and 260 (ethylaminoacyl group, C$_{15}$H$_{13}$ClNO), 224 (Tr—CH$_2$COHAr, C$_{10}$H$_8$F$_2$N$_3$O), 215 and 217 (acyl group, C$_{13}$H$_8$ClO); [α]$^D$=–97.7° (c 1, CHCl$_3$).

EXAMPLE 73

(1R,2R)-4-(4-Chlorophenyl)-N-[2-(2,4-difluorophenyl)-2-hydroxy-1-methyl-3-(1H-1,2,4-triazol-1-yl)propyl]benzamide Following a similar procedure to that described in example 1 but using 4-(4-chlorophenyl)benzoic acid the title compound was obtained as a white solid: mp 173°–174° C.; $^1$H NMR (300 MHz, CDCl$_3$) δ (TMS) 7.93 (dt, J$_t$=1.7, J$_d$=8.4, 2H, arom), 7.79 (s, 2H, triazole), 7.66 (dt, J$_t$=1.7, J$_d$=8.4, 2H, arom), 7.55 (dt, J$_t$=2, J$_d$=8.6, 2H, arom), 7.44 (dt, J$_t$=2, J$_d$=8.6, 2H, arom), 7.40 (dt, J$_d$=6.5, J$_t$=8.8, 1H, arom), 6.8–6.6 (m, 3H, arom, NH), 5.37 (br s, 1H, OH), 5.08 (d, J=14.3, 1H, TrCH(H)), 5.00 (br quint, J=7, 1H, CHMe), 4.50 (d, J=14.3, 1H, TrCH(H)), 1.04 (d, J=6.8, 3H, MeCH); GC/MS 258 and 260 (ethylaminoacyl group, C$_{15}$H$_{13}$ClNO), 224 (Tr—CH$_2$COHAr, C$_{10}$H$_8$F$_2$N$_3$O), 215 and 217 (acyl group, C$_{13}$H$_8$ClO); [α]$^D$=–110.2° (c 1, CHCl$_3$).

EXAMPLE 74

(1R,2R)-2-(4-Chlorophenyl)-N-[2-(2,4-difluorophenyl)-2-hydroxy-1-methyl-3-(1H-1,2,4-triazol-1-yl)propyl]-7-methylpyrazolo[,1,5-a]pyrimidine-6-carboxamide Following a similar procedure to that described in example 1 but using 2-(4-chlorophenyl)-7-methylpyrazolo[1,5-a]pyrimidine-6-carboxylic acid the title compound was obtained as a white solid: mp 227°–228 ° C.; $^1$H NMR (300 MHz, CDCl$_3$) δ (TMS) 8.61 (s, 1H, arom), 7.99 (dt, J$_t$=2.0, J$_d$=8.6, 2H, arom), 7.83 (s, 2H, triazole), 7.47 (dt, J$_t$=2.0, J$_d$=8.6, 2H, arom), 7.39 (dt, J$_d$=6.5, J$_t$=8.8, 1H, arom), 7.03 (s, 1H, arom), 6.8–6.6 (m, 2H, arom), 6.62 (br d, J=9.4, 1H, NH), 5.42 (s, 1H, OH), 5.13 (d, J=14.2, 1H, TrCH(H)), 5.02 (br quint, J=7, 1H, CHMe), 4.55 (d, J=14.2, 1H, TrCH(H)), 3.13 (s, 3H, Me-heterocycle), 1.09 (d, J=6.8, 3H, MeCH); MS 313 and 315 (ethylaminoacyl group, C$_{16}$H$_{14}$ClN$_4$O), 270 and 272 (acyl group, C$_{14}$H$_9$ClN$_3$O), 224 (Tr—CH$_2$COHAr, C$_{10}$H$_8$F$_2$N$_3$O); [α]$^D$=–93.8° (c 1, CHCl$_3$). Analysis calculated for C$_{26}$H$_{22}$ClF$_2$N$_7$O$_2$S: C 58.05 H 4.12; N 18.23. Found: C 1 5 58.37; H 4.19; N 18.04.

EXAMPLE 75

(1R,2R)-5-(4-Chlorophenyl)-N-[2-(2,4-difluorophenyl)-2-hydroxy-1-methyl-3-(1H-1,2,4-triazol-1-yl)propyl]furan-2-carboxamide Following a similar procedure to that described in example 1 but using 5-(4-chlorophenyl)furan-2-carboxylic acid the title compound was obtained as a white solid: mp 218°–219° C.; $^1$H NMR (300 MHz, CDCl$_3$) δ (TMS) 7.79 (s, 1H, triazole), 7.78 (s, 1H, triazole), 7.69 (dt, J$_t$=2, J$_d$=8.4, 2H, arom), 7.42 (dt, J$_t$=2, J$_d$=8.4, 2H, arom), 7.39 (dt, J$_d$=6.5, J$_t$=8.8, 1H, arom), 7.25 (d, J=3.6, 1H, furan), 6.88 (br d, J=9.5, 1H, NH), 6.8–6.6 (m, 2H, arom), 6.76 (d, J=3.6, 1H, furan), 5.39 (br s, 1H, OH), 5.04 (d, J=14.2, 1H, TrCH(H)), 4.96 (br quint, J=7, 1H, CHMe), 4.53 (d, J=14.2, 1H, TrCH(H)), 1.05 (d, J=6.8, 3H, MeCH); GC—MS 248 and 250 (ethylaminoacyl group, C$_{13}$H$_{11}$ClNO$_2$), 224 (Tr—CH$_2$COHAr, C$_{10}$H$_8$F$_2$N$_3$O), 205 and 207 (acyl group, C$_{11}$H$_6$ClO$_2$); [α]$^D$=–173° (c 1, CHCl$_3$). Analysis calculated for C$_{23}$H$_{19}$ClF$_2$N$_4$O$_3$: C 58.42; H 4.05; N 11.85. Found: C 57.15; H 3.85; N 10.74.

EXAMPLE 76

(1R*,2R*)-2-(4-Cyanophenyl)-N-[2-hydroxy-1-methyl-3-(1H-1,2,4-triazol-1-yl)-2-(4-trifluoromethylphenyl)propyl]-4-methylthiazole-5-carboxamide Following a similar procedure to that described in example 29 but using (2R*,3R*)-3-amino-1-(1H-1,2,4-triazol-1-yl)-2-(4-trifluoromethylphenyl)-2-butanol (obtained as described in EP 617031) the title compound was obtained as a white solid: mp 105°–111° C.; $^1$H NMR (300 MHz, CDCl$_3$) δ (TMS) 8.08 (d, J=8.2, 2H, arom), 7.84 (s, 1H, triazole), 7.76 (d, J=8.2, 2H, arom), 7.64 (s, 1H, triazole), 7.57 (d, J=8.4, 2H, arom), 7.47 (d, J=8.4, 2H, arom), 6.45 (br d, J=9.2, 1H, NH), 5.46 (d, J=1.0, 1H, OH), 4.75 (d, J=14.2, 1H, TrCH(H)), 4.74 (br quint, J=7, 1H, CHMe), 4.55 (d, J=14.2, 1H, TrCH(H)), 2.83 (s, 3H, Me-thiazole), 1.03 (d, J=6.8, 3H, MeCH); GC—MS 270 (ethylaminoacyl group, C$_{14}$H$_{12}$N$_3$OS), 256 (Tr—CH$_2$COHAr, C$_{11}$H$_9$F$_3$N$_3$O), 227 (acyl group, C$_{12}$H$_7$N$_2$OS).

EXAMPLE 77

(1R,2R)-2-(4-Cyanophenyl)-N-[2-(2,4-difluorophenyl)-2-hydroxy-1-methyl-3-(1H-1,2,4-triazol-1-yl)propyl]-N-methyl-4-methylthiazole-5-carboxamide Following a similar procedure to that described in example 29 but using (2R,3R)-3-(N-methylamino)-2-(2,4-difluorophenyl)-1-(1H-1,2,4-triazol-1-yl)-2-butanol (obtained as described in EP 332,387) the title compound was obtained as a white amorphous solid: $^1$H NMR (300 MHz, CDCl$_3$) δ (TMS) 8.04 (d, J=8.4, 2H, arom), 7.9–7.7 (m, 4H, triazole, arom), 7.5–7.3 (m, 1H, arom), 6.9–6.7 (m, 2H, arom), 5.5–5.3 (m, 3H, OH, TrCH(H), CHMe), 4.37 (d, J=14.2, 1H, TrCH(H)), 3.28 (s, 3H, NMe), 2.55 (s, 3H, Me-thiazole), 1.2–1.1 (m, 3H, MeCH); GC—MS 284 (ethylmethylaminoacyl group, C$_{15}$H$_{14}$N$_3$OS), 227 (acyl group, C$_{12}$H$_7$N$_2$OS), 224 (Tr—CH$_2$COHAr, C$_{10}$H$_8$F$_2$N$_3$O); [α]$^D$=−115.2° (c 1, CHCl$_3$). Analysis calculated for C$_{25}$H$_{22}$F$_2$N$_6$O$_2$S: C 59.05; H 4.36; N 16.53; S 6.30. Found: C 58.81; H 4.53; N 16.42; S 5.69.

EXAMPLE 78

(1R,2R)-2-(4-Cyanophenyl)-N-[2-(2,4-difluorophenyl)-2-hydroxy-1-methyl-3-(1H-1,2,4-triazol-1-yl)propyl]-N-(2-benzyloxyethyl)-4-methylthiazole-5-carboxamide Following a similar procedure to that described in example 29 but using (2R,3R)-3-[[2-(benzyloxy)ethyl]amino]-2-(2,4-difluorophenyl)-1-(1 H-1,2,4-triazol-1-yl)-2-butanol (obtained as described in EP 617031) the title compound was obtained as a white amorphous solid: $^1$H NMR (300 MHz, CDCl$_3$) δ (TMS) 8.1–7.9 (m, arom), 7.76 (s), 7.74 (s), 7.7–7.5 (m, arom), 7.4–7.2 (m, arom), 6.9–6.7 (m, 2H, arom), 5.5 (br m, 1H), 5.04 (d, J=14.2, 1H, TrCH(H)), 4.7–4.5 (m, 4H, CH$_2$OCH$_2$), 4.40 (d, J=14.2, 1H, TrCH(H)), 4.0–3.5 (m), 2.47 (s, 3H, Me-thiazole), 1.2–1.0 (m, 3H, MeCH); MS (DIP) 284 (ethylbenzyloxyethylaminoacyl, C$_{23}$H$_{22}$N$_3$O$_2$S), 227 (acyl group, C$_{12}$H$_7$N$_2$OS), 224 (Tr—CH$_2$COHAr, C$_{10}$H$_8$F$_2$N$_3$O); [α]$^D$=−69.7° (c 1, CHCl$_3$).

EXAMPLE 79

(1R,2R)-2-(4-Cyanophenyl)-N-[2-(2,4-difluorophenyl)-2-hydroxy-1-methyl-3-(1H-1,2,4-triazol-1-yl)-propyl]-N-(ethoxycarbonylmethyl)-4-methylthiazole-5-carboxamide Following a similar procedure to that described in example 29 but using (2 R,3)-3-[(ethoxycarbonylmethyl)amino]-2-(2,4-difluorophenyl)-1-(1H-1,2,4 -triazol-1-yl)-2-butanol (obtained as described in EP 617031) the title compound was obtained as a white amorphous solid: $^1$H NMR (300 MHz, CDCl$_3$) δ (TMS) 8.08 (m, 2H, arom), 7.8 (m, 4H, triazole, arom), 7.4–7.1 (m, 1H, arom), 6.9–6.7 (m, 2H, arom), 5.5 (m, 1H, OH), 5.2–5.1 (m, 2H, CH$_2$CO$_2$Et), 5.0–4.1 (m, 5H, TrCH$_2$, CHMe, CH$_3$CH$_2$O), 2.61 and 2.53 (br s, 3H, Me-thiazole), 1.2–1.0 (m, 6H, MeCH, CH$_3$CH$_2$O); [α]$^D$=−142.5° (c 1, CHCl$_3$). Analysis calculated for C$_{28}$H$_{26}$F$_2$N$_6$O$_4$S.1H$_2$O: C 56.18; H 4.71; N 14.04; S 5.36. Found: C 56.19; H 4.50; N 14.00; S 5.17.

EXAMPLE 80

(1R,2R)-2-(4-Cyanophenyl)-N-[2-(2,4-difluorophenyl)-2-hydroxy-1-methyl-3-(1H-1,2,4-triazol-1-yl)propyl]-N-(benzyloxycarbonylmethyl)-4-methylthiazole-5-carboxamide Following a similar procedure to that described in example 29 but using (2R,3R)-3-[(benzyloxycarbonylmethyl)amino]-2-(2,4-difluorophenyl)-1-(1H-1,2,4-triazol-1-yl)-2-butanol (obtained as described in EP 617031) the title compound was obtained as a white amorphous solid: $^1$H NMR (300 MHz, CDCl$_3$) δ (TMS) 8.0 (m, 2H, arom), 7.8–7.7 (m, 4H, triazole, arom), 7.4–7.1 (m, 6H, arom), 6.8–6.6 (m, 2H, arom), 5.5 (m, 1H, OH), 5.4–4.4 (m, 7H, CH$_2$Ph, CH$_2$CO$_2$Bn, TrCH$_2$, CHMe), 2.5 (br s, 3H, Me-thiazole), 1.2–1.0 (m, 3H, MeCH); [α]$^D$=−114.2° (c 0.2, CHCl$_3$).

EXAMPLE 81

(1R,2R)-2-(4-Cyanophenyl)-N-[2-(2,4-difluorophenyl)-2-hydroxy-1-methyl-3-(1H-1,2,4-triazol-1-yl)propyl]-N-(carboxymethyl)-4-methylthiazole-5-carboxamide, trihydrate A mixture of the product obtained in the preceding example (600 mg, 1 mmol), 5% Pd/C (25 mg) and ethanol (25 mL) was hydrogenated (1 atm) at room temperature for 6 h. The resulting crude product was filtered through celite and the filtrate was evaporated to dryness to afford the title compound as a white solid (450 mg, 88%): mp 153°–159° C.; [α]$^D$=−73.80 (c 0.2, MeOH). Analysis calculated for C$_{26}$H$_{22}$F$_2$N$_6$O$_4$S.3H$_2$O: C 51.48; H 4.65; N 13.85; S 5.29. Found: C 51.85; H 4.40; N 13.60; 5 4.61.

EXAMPLE 82

(1R,2R)-2-(4-Cyanophenyl)-N-[2-(2,4-difluorophenyl)-2-hydroxy-1-methyl-3-(1H-1,2,4-triazol-1-yl)propyl]-N-(2-hydroxyethyl)-4-methylthiazole-5-carboxamide To a solution of the product obtained in example 79 (2.46 g, 4.23 mmol) in ethanol (25 mL) was slowly added NaBH$_4$ in 3 portions (0.48 mg, 12.7 mmol). The mixture was stirred at room temperature for 20 h, and the reaction was then quenched by the addition of saturated aqueous NH$_4$Cl solution. The resulting mixture was concentrated and the residue partitioned between water and CHCl$_3$. The organic phase was separated, dried over anhydrous Na$_2$SO$_4$, filtered and concentrated to a residue. This was purified by flash chromatography to give the title compound as a white solid: mp 113°–119 ° C.; $^1$H NMR (300 MHz, CDCl$_3$) δ (TMS) 8.27 (br s), 8.05 (br m, 2H, arom), 7.75 (br m, 4H, triazole, arom), 7.36 (m, 1H, arom), 6.9–6.5 (m, 2H, arom), 5.71 (br s, 1H, OH), 4.9–4.6 (m, 2H, TrCH(H), CHMe), 4.2–3.5 (m, 5H, NCH$_2$CH$_2$, TrCH(H)), 2.54 and 2.46 (s, 3H, Me-thiazole), 1.3–1.1 (m, 3H, MeCH); GC—MS 314 (ethylhydroxyethylaminoacyl group, C$_{16}$H$_{16}$N$_{13}$O$_2$S), 271 (ethylaminoacyl group +1, C$_{14}$H$_{12}$N$_3$OS), 227 (acyl group, $C_{12}H_7N_2OS$), 224 (Tr—$CH_2COHAr$, $C_{10}H_8F_2N_3O$); $[\alpha]^D$= −76.5° (c 1, $CHCl_3$).

EXAMPLE 83

(4R,5R)-4-[5-[5-(2,4-Difluorophenyl)-4-methyl-5-[(1H-1,2,4-triazol-1-yl)methyl]-oxazolidine-3-carbonyl]-4-methylthiazol-2-yl]benzonitrile Following a similar procedure to that described in example 29 but using (4R,5R)-5-(2,4-difluorophenyl)-4-methyl-5-[(1H-1,2,4-triazol-1 -yl)methyl]oxazolidine (obtained as described in EP 332,387) the title compound was obtained as a white solid: mp 200°–201° C.; $^1$H NMR (300 MHz, $CDCl_3$) δ (TMS) 8.08 (d, J=8.1, 2H, arom), 7.77 (d, J=8.1, 2H, arom), 7.77 (s, 1H, triazole), 7.72 (s, 1H, triazole), 7.31 (dt, $J_d$=6.6, $J_t$=8.7, 1H, arom), 7.0–6.8 (m, 2H, arom), 5.43 (br s, 1H, OCH(H)N), 5.31 (d, J=4.5, 1H, OCH(H)N), 5.1–4.9 (br s, 1H, CHMe), 4.58 (AB q, Δv=0.059, J=14.7, 2H, $TrCH_2$), 2.65 (s, 3H, Me-thiazole), 1.04 (d, J=6.6, 3H, MeCH); GC—MS 227 (acyl group, $C_{12}H_7N_2OS$); $[\alpha]^D$=+17.5° (c 1, $CHCl_3$). Analysis calculated for $C_{25}H_{20}F_2N_6O_2S$: C 59.28; H 3.98; N 16.59; S 6.33. Found: C 59.29; H 3.83; N 16.16; S 6.06.

EXAMPLE 84

(2R,3R)-4-[5-[2-(2,4-Difluorophenyl)-3-methyl-2-[(1H-1,2,4-triazol-1-yl)methyl]morpholine-4-carbonyl]-4-methylthiazol-2-yl]benzonitrile A cooled (0° C.) solution of (1R,2R)-2-(4-cyanophenyl)-N-[2-(2,4-difluorophenyl)-2-hydroxy-1-methyl-3-(1H-1,2,4-triazol-1-yl)propyl]-N-(2-hydroxyethyl)-4-methylthiazole-5-carboxamide (0.45 g, 0.83 mmol, obtained in example 82) in THF (10 mL) was treated with diethylazadicarboxylate (0.20 mL, 1.25 mmol) and tributylphosphine (0.31 mL, 1.25 mmol) for 20 h at room temperature. The mixture was evaporated to dryness and the residue was purified by flash chromatography to give the title compound as a white solid: mp 150°–160° C.; 1H NMR (300 MHz, $CDCl_3$) δ (TMS) 8.06 (d, J=8.4, 2H, arom), 7.76 (s, 1H, triazole), 7.76 (d, J=8.4, 2H, arom), 7.30 (s, 1H, triazole), 7.4–7.2 (m, 1H, arom), 7–6.7 (m, 2H, arom), 5.53 (br), 5.17 (d, J=15.1, 1H, TrCH(H)), 4.7 (br d, 1H), 4.6–4.4 (m, 1H), 4.0 (br d), 3.6 (br s), 2.57 (s, 3H, Me-thiazole), 1.13 (d, J=6.8, 3H, MECH); GC—MS 293 ($M^+$-acyl, $C_{14}H_{15}N_4F_2O$), 227 (acyl group, $C_{12}H_7N_2OS$); $[\alpha]^D$=−80.5° (c 1, $CHCl_3$).

EXAMPLE 85

(2R,3R)-4-[5-[2-(2,4-Difluorophenyl)-6-hydroxy-3-methyl-2-[(1H-1,2,4-triazol-1-yl)methyl]morpholine-4-carbonyl]-4-methylthiazol-2-yl]benzonitrile To a cooled (−78° C.) solution of DMSO (0.29 mL, 4.17 mmol) in $CH_2Cl_2$ (10 mL) was added a solution of trifluoroacetic anhydride (0.30 mL, 2.09 mmol) in $CH_2Cl_2$ (1 mL) dropwise. After ten minutes, a solution of (1R,2R)-2-(4-cyanophenyl)-N-[2-(2,4-difluorophenyl)-2-hydroxy-1-methyl-3-(1H-1,2,4-triazol-1-yl)propyl]-N-(2-hydroxyethyl)-4-methylthiazole-5-carboxamide (0.9 g, 1.67 mmol, obtained in example 82) in $CH_2Cl_2$ (3 mL) was added. The mixture was stirred for 1 h, and then triethylamine (1.1 mL, 8.3 mmol) was added. The reaction mixture was allowed to warm up to −40° C. and was stirred at this temperature for 1.5 h and then at −10° C. for 30 min. 10% aqueous $NaHCO_3$ solution was added, the organic phase was separated and the aqueous phase was extracted with chloroform. The combined organic extracts were washed with water, dried over anhydrous $Na_2SO_4$, filtered and concentrated to a crude product. Purification by flash chromatography afforded the title compound as a white solid: mp 225°–228° C.; $^1$H NMR (300 MHz, $CDCl_3$) δ (TMS) 8.06 and 8.05 (d, J=8.4, 2H, arom), 7.77 (s, 1H, triazole), 7.76 (d, J=8.4, 2H, arom), 7.35 (dt, $J_d$=6.5, $J_t$=8.8, 1H, arom), 7.30 (s, 1H, triazole), 7.0–6.7 (m, 2H, arom), 5.83 (m, 1H, OCHOH), 5.8–3.2 (several broad signals), 2.57 and 2.55 (s, 3H, Me-thiazole), 1.14 (d, J=6.8, 3H, MeCH); $[\alpha]^D$=−79.8° (c 1, $CHCl_3$). Analysis calculated for $C_{26}H_{22}F_2N_6O_3S$·½$H_2O$: C 57.24; H 4.21; N 15.40; S 5.86. Found: C 57.49; H 4.03; N 15.08; S 5.69.

EXAMPLE 86

(2R,3R)-4-[5-[2-(2,4-Difluorophenyl)-3-methyl-6-oxo-2-[(-1,2,4-triazol-1-yl)methyl]morpholine-4-carbonyl]-4-methylthiazol-2-yl]benzonitrile From the first fractions of the above chromatography the title compound was isolated as a white amorphous solid: GC—MS 227 (acyl group, $C_{12}H_7N_2OS$).

EXAMPLE 87

(1R,2R)-2-(4-Cyanophenyl)-N-[2-(2,4-dichlorophenyl)-2-hydroxy-1-methyl-3-(1H-1,2,4-triazol-1-yl)propyl]-4-methylthiazole-5-carboxamide Following a similar procedure to that described in example 29 but using (2R,3R)-3-amino-2-(2,4-dichlorophenyl)-1-(1 H-1,2,4-triazol-1-yl)-2-butanol (obtained following the general procedure described in J. Org. Chem., 1995, 60, 3000–3012) the title compound was obtained as a white solid: mp 109°–113° C.; $^1$H NMR (300 MHz, $CDCl_3$) δ (TMS) 8.07 (dt, $J_t$=1. 8, $J_d$=6.9, 2H, arom), 7.83 (s, 1H, triazole), 7.81 (s, 1H, triazole), 7.76 (dt, $J_t$=1.8, $J_d$=6.9, 2H, arom), 7.51 (d, J=8.4, 1H, arom), 7.35 (d, J=2.1, 1H, arom), 7.12 (dd, J=2.1, 1J=8.7, 1H, arom), 6.50 (br d, J=9.2, 1H, NH), 5.63 (d, J=14.4, 1H, TrCH(H)), 5.51 (br s, 1H, OH), 5.45 (m, 1H, CHMe), 4.45 (d, J=14.4, 1H, TrCH(H)), 2.83 (s, 3H, Me-thiazole), 0.99 (d, J=6.6, 3H, MeCH); GC—MS 270 (ethylaminoacyl group, $C_{14}H_{12}N_3OS$), 256 and 258 (Tr—$CH_2COHAr$, $C_{10}H_8Cl_2N_3O$), 227 (acyl group, $C_{12}H_7N_2OS$); $[\alpha]^D$=−106.3° (c 1, $CHCl_3$). Analysis calculated for $C_{24}H_{20}Cl_2N_6O_2S$: C 54.75; H 3.83; N 15.97; S 6.08. Found: C 54.28; H 3.89; N 16.02; S 5.69.

EXAMPLE 88

(1R,2R)-N-[2-(2,4-Difluorophenyl)-2-hydroxy-1-methyl-3-(1H-1,2,4-triazol-1-yl)propyl]-2-[4-[hydroxyamino(imino)methyl]phenyl]-4-methylthiazole-5-carboxamide To a solution of $Na_2CO_3$ (0.72 g, 6.77 mmol) in a mixture of $H_2O$ (5 mL) and THF (5 mL) was added (1R,2R)-2-(4-cyanophenyl)-N-[2-(2,4-difluorophenyl)-2-hydroxy-1-methyl-3-(1H-1,2,4-triazol-1 -yl)propyl]-4-methyl-thiazole-5-carboxamide methanesulfonate (0.5 g, 0.84 mmol, obtained in example 31) and hydroxylamine hydrochloride (0.29 g, 4.23 mmol). The reaction mixture was stirred at room temperature overnight, and was then concentrated and the aqueous residue extracted with $CHCl_3$. The organic phase was separated, dried over $Na_2SO_4$, filtered and the filtrate was concentrated to a solid. Purification by flash chromatography afforded the title compound as a pale yellow solid: mp 135°–148° C.; $^1$H NMR (300 MHz, MeOH—d$_4$) δ (MeOH—d$_4$) 8.24 (s, 1H, triazole), 8.03 (dt, J$_t$=1.6, J$_d$=8.5, 2H, arom), 7.78 (dt, J$_t$=1.6, J$_d$=8.5, 2H, arom), 7.71 (s, 1H, triazole), 7.38 (dt, J$_d$=6.5, J$_t$=8.8, 1H, arom), 6.97 (ddd, J=2.4, J=8.7, J=11.5, 1H, arom), 6.84 (dt, J$_d$=2.1, J$_t$=8.0, 1H, arom), 5.00 (q, J=7, 1H, CHMe), 4.99 (d, J=14.3, 1H, TrCH(H)), 4.58 (d, J=14.3, 1H, TrCH(H)), 2.74 (s, 3H, thiazole-Me), 1.05 (d, J=7, 3H, MeCH); MS 496 (M$^+$-NH$_2$); [α]$^D$=−77.2° (c 1, MeOH). Analysis calculated for C$_{24}$H$_{23}$F$_2$N$_7$O$_3$S.H$_2$O: C 52.84; H 4.62; N 17.97; S 5.88 Found: C 53.48; H 4.61; N 17.19; S 5.34.

EXAMPLE 89

(1R,2R)-2-[4-[Acetoxyamino (imino)methyl]phenyl] -N-[2-(2,4-difluorophenyl)-2-hydroxy-1-methyl-3-(1H-1,2,4-triazol-1-yl)propyl]-4-methyl thiazole-5-carboxamide A solution of the product obtained in example 88 (150 mg, 0.28 mmol) in CHCl$_3$ (10 mL) was treated with triethylamine (33 μL, 0.33 mmol) and acetyl chloride (25 μL, 0.32 mmol) at 25° C. for 18 h. Next, 10% aqueous NaHCO$_3$ was added and the layers were separated. The organic phase was washed with water, dried over Na$_2$SO$_4$, filtered, concentrated and purified by flash chromatography to give the title compound as a white solid: mp 146°–147° C.; $^1$H NMR (300 MHz, CDCl$_3$) δ (TMS) 8.01 (dt, J$_t$=1.9, J$_d$=8.7, 2H, arom), 7.81 (s, 1H, triazole), 7.80 (dt, J$_t$=1.9, J$_d$=8.7, 2H, arom), 7.79 (s, 1H, triazole), 7.38 (dt, J$_d$=6.5, J$_t$=8.8, 1H, arom), 6.8–6.6 (m, 2H, arom), 6.43 (br d, J=9.5, 1H, NH), 5.38 (s, 1H, OH), 5.13 (br s, 2H, NH$_2$), 5.05 (d, J=14.5, 1H, TrCH(H)), 4.94 (br quint, J=7, 1H, CHMe), 4.52 (d, J=14.5, 1H, TrCH(H)), 2.82 (s, 3H, Me-thiazole), 2.27 (s, 3H, COMe), 1.02 (d, J=6.8, 3H, MeCH); MS 327 (N-ethylheterocycle-H$_2$O, C$_{16}$H$_{16}$N$_4$O$_2$S), 284 (acyl group-H$_2$O, C$_{14}$H$_{10}$N$_3$O$_2$S), 224 (Tr—CH$_2$COHAr, C$_{10}$H$_8$F$_2$N$_3$O); [α]$^D$=−103.9° (c 1, MeOH). Analysis calculated for C$_{26}$H$_{25}$F$_2$N$_7$O$_4$S: C 54.83; H 4.42; N 16.76; S 5.63 Found: C 53.97; H 4.38; N 16.90; S 5.23.

EXAMPLE 90

(1R,2R)-2-(4-Tert-butylphenyl)-N-[2-(2,4-difluorophenyl)-2-hydroxy-1-methyl-3-(1H-1,2,4-triazol-1-yl)propyl]-4-methylthiazole-5-carboxamide Following a similar procedure to that described in example 1 but using 2-(4-tert-butylphenyl)-4-methylthiazole-5-carboxylic acid (reference example 43) the title compound was obtained as a white solid: mp 85°–91° C.; $^1$H NMR (300 MHz, CDCl$_3$) δ (TMS) 7.88 (dt, J$_t$=2, J$_d$=8.5, 2H, arom), 7.81 (s, 1H, triazole), 7.79 (s, 1H, triazole), 7.47 (dt, J$_t$=2, J$_d$=8.5, 2H, arom), 7.38 (dt, J$_d$=6.5, J$_t$=8.8, 1H, arom), 6.8–6.6 (m, 2H, arom), 6.38 (br d,J=9.5, 1H, NH), 5.37 (s, 1H, OH), 5.05 (d, J=14.5, 1H, TrCH(H)), 4.93 (br quint, J=7, 1H, CHMe), 4.53 (d, J=14.5, 1H, TrCH(H)), 2.81 (s, 3H, Me-thiazole), 1.35 (s, 9H, CMe$_3$), 1.02 (d, J=6.8, 3H, MeCH); GC—MS 301 (ethylaminoacyl group, C$_{17}$H$_{22}$N$_2$OS), 258 (acyl group, C$_{15}$H$_{16}$NOS), 224 (Tr—CH$_2$COHAr, C$_{10}$H$_8$F$_2$N$_3$O); [α]$^D$=−105.9° (c 1, CHCl$_3$). Analysis calculated for C$_{27}$H$_{29}$F$_2$N$_5$O$_2$S: C 61.70; H 5.56; N 13.32; S 6.10. Found: C 61.70; H 6.20; N 12.64; S 5.24.

EXAMPLE 91

(1R,2R)-2-(4-Cyanophenyl)-N-[2-(2,4-difluorophenyl)-2-hydroxy-1-methyl-3-(1H-imidazol-1-yl)propyl]-4-methylthiazole-5-carboxamide Following a similar procedure to that described in example 1 but using 2-(4-cyanophenyl)-4-methylthiazole-5-carboxylic acid (reference example 24) and (2R,3R)-3-amino-2-(2,4-difluorophenyl)-1-(1H-imidazol-1 -yl)-2-butanol (75 mg, 0.28 mmol, obtained following the general procedure described in *J. Org. Chem.*, 1995, 60, 3000–3012) in DMF (5 mL) the title compound was obtained as a white solid: mp 126°–128° C.; $^1$H NMR (300 MHz, CDCl$_3$) δ (TMS) 8.05 (dt, J$_t$=2, J$_d$=8.4, 2H, arom), 7.50 (dt, J$_t$=2, J$_d$=8.4, 2H, arom), 7.47 (dt, J$_d$=6.5, J$_t$=8.8, 1H, arom), 7.24 (s, 1H, imidazole), 6.84.6 (m, 2H, arom), 6.52 (br d, J=9.5, 1H, NH, 6.51 (s, 1H, imidazole), 6.32 (s, 1H, imidazole), 4.85 (br quint, J=7, 1H, CHMe), 4.68 (d, J=14.5, 1H, ImCH(H)), 4.29 (d, J=14.5, 1H, ImCH(H)), 2.80 (s, 3H, Me-thiazole), 1.06 (d, J=6.8, 3H, MeCH); MS 227 (acyl group, C$_{12}$H$_7$N$_2$OS), 223 (Im—CH$_2$COHAr, C$_{11}$H$_9$F$_2$N$_2$O); [α]$^D$=−20.4° (c 1, CHCl$_3$). Analysis calculated for C$_{25}$H$_{21}$F$_2$N$_5$O$_2$S: C 60.84; H 4.29; N 14.19; S 6.50 Found: C 60.85; H 4.31; N 13.75; S 6.18.

EXAMPLE 92

(1R,2R)-2-(4-Cyanophenyl)-N-[2-(2-fluorophenyl)-2-hydroxy-1-methyl-3-(1H-1,2,4-triazol-1-yl)propyl] -4-methylthiazole-carboxamide Following a similar procedure to that described in example 29 but using (2R,3R)-3-amino-2-(2-fluorophenyl) -1-(1H-1,2,4-triazol-1-yl)-2-butanol (obtained as described in *J. Org. Chem.*, 1995, 60, 3000–3012) the title compound was obtained as a white solid: mp 107°–114° C.; $^1$H NMR (300 MHz, CDCl$_3$) δ (TMS) 8.07 (dt, J$_t$=1.8, J$_d$=8.6, 2H, arom), 7.79 (s, 1H, triazole), 7.76 (dt, J$_t$=1.8, J$_d$=8.6, 2H, arom), 7.75 (s, 1H, triazole), 7.36 (dt, J$_d$=1.6, J$_t$=7.8, 1H, arom), 7.3–7.3 (m, 1H, arom), 7.1–7.0 (m, 2H, arom), 6.50 (br d, J=9.3, 1H, NH), 5.29 (d, J=1.6, 1H, OH), 5.08 (d, J=14.2, 1H, 7rCH(H)), 4.99 (br quint, J=7, 1H, CHMe), 4.52 (d, J=14.2, 1H, TrCH(H)), 2.83 (s, 3H, Me-thiazole), 1.03 (d, J=6.8, 3H, MeCH); GC/MS 270 (ethylaminoacyl group, C$_{14}$H$_{12}$N$_3$OS), 227 (acyl group, C$_{12}$H$_7$N$_2$OS), 206 (Tr—CH$_2$COHAr, C$_{10}$H$_9$FN$_3$O); [α]$^D$=−115.61° (c 1, CHCl$_3$). Analysis calculated for C$_{24}$H$_{21}$FN$_6$O$_2$S.½H$_2$O: C 59.36; H 4.53; N 17.30; S 6.59. Found: C 59.63; H 4.73; N 16.68; S 6.15.

EXAMPLE 93

(1R,2R)-N-[2-(2,4Difluorophenyl)-2-hydroxy-1-methyl-3-(1H-1,2,4-tiazol-1-yl)propyl]-2-4fluorophenyl)4-methylthiazole-carboxamide Following a similar procedure to that described in example 1 but using 2-(4fluorophenyl) methylthiazole-5-carboxylic acid the title compound was obtained as a white amorphous solid: $^1$H NMR (300 MHz, CDCl$_3$) δ (TMS) 7.96 (m, 2H, arom), 7.81 (s, 1H, triazole), 7.79 (s, 1H, triazole), 7.37 (dt, J$_d$=65, J$_t$=8.8, 1H, arom), 7.16 (tt, J=2, J=8.5, 2H, arom), 6.8–6.6 (m, 2H, arom), 6.40 (br d, J=9.5, 1H, NH), 5.41 (s, 1H, OH), 5.05 (d, J=14.5, 1H, TrCH(H)), 4.94 (br quint, J=7, 1H, CHMe), 4.52 (d, J=14.5, 1H, TrCH(H)), 2.80 (s, 3H, Me-thiazole), 1.02 (d, J=6.8, 3H, MeCH); MS 263 (ethylaminoacyl group, C$_{13}$H$_{12}$FN$_2$OS), 220 (acyl group, C$_{11}$H$_7$FNOS), 224 (Tr—CH$_2$COHAr, C$_{10}$H$_8$F$_2$N$_3$O); [α]$^D$=−113.5° (c 0.5, CHCl$_3$). Analysis calculated for C$_{23}$H$_{20}$F$_3$N$_5$O$_2$S: C 56.67; H 4.14; N 14.37; S 6.58 Found. C 56.87; H 4.19; N 14.00; S 6.29.

EXAMPLE 94

In vitro activity

In vitro activity was evaluated against *C. albicans, C. krusei,* and *Aspergillus fumigatus* by the agar dilution method. Test strains were either clinical isolates or were obtained from ATCC. Stock solutions containing 800 μg/mL were prepared by solving the test products in 50% ethanol. The culture medium used was Kimmig's agar (K. A., E. Merck) suplemented with 0.5% glycerol. Plates containing serial dilutions (80 to 0.025 μg/mL) of the test products were inoculated with 10 μL of the fungal inocula, containing $10^5$ colony forming units (cfu)/mL. Plates were incubated at 25° C. during 48 h for Canadida p. and during 5 days for *Apergillus fumigatus*. Following incubation MICs (minimal inhibitory concentrations) were determined. Results are shown in the following table:

| IN VITRO ACTIVITIES (MIC in μg/mL) | | | |
|---|---|---|---|
| EXAMPLE No. | C. albicans | C. krusei | Asp. fumigatus |
| 2 | 0.15 | 2.5 | 10 |
| 3 | 0.07 | 5 | 5 |
| 8 | 1.15 | 1.25 | 10 |
| 10 | 0.63 | 2.5 | 10 |
| 15 | 0.15 | 2.5 | 5 |
| 19 | 0.15 | 5 | 2.5 |
| 22 | ≦0.03 | 0.63 | 5 |
| 23 | ≦0.03 | 2.5 | 5 |
| 24 | ≦0.03 | 1.25 | 1.25 |
| 25 | ≦0.03 | 1.25 | 1.25 |
| 26 | ≦0.03 | 0.63 | 1.25 |
| 27 | 0.15 | 1.25 | 0.63 |
| 28 | ≦0.03 | 1.25 | 1.25 |
| 29 | ≦0.03 | 2.5 | 2.5 |
| 34 | 0.07 | 1.25 | 10 |
| 39 | 0.07 | 0.63 | 1.25 |
| 41 | ≦0.03 | 1.25 | 2.5 |
| 43 | ≦0.03 | 1.25 | 10 |
| 51 | ≦0.03 | 0.31 | 2.5 |
| 55 | ≦0.03 | 0.07 | 0.31 |
| 57 | ≦0.03 | 0.63 | 0.63 |
| 59 | ≦0.03 | 0.63 | 5 |
| 74 | 0.07 | 1.25 | 5 |
| 77 | ≦0.03 | 1.25 | 2.5 |
| 87 | ≦0.03 | 0.63 | 1.25 |
| 90 | 0.63 | 1.25 | 1.25 |
| 92 | ≦0.03 | 5 | 2.5 |

EXAMPLE 95

In vivo activity (systemic candidiasis)

Groups of 10 male mice were inoculated i.v. with 0.2 mL of a suspension containing $(2-8) \times 10^7$ cfu/mL of *Candida albicans*. Compounds were administered orally at 1 mg/kg at times 1, 4 and 24 h after infection. Following this protocol, animals treated with the products of examples 2, 3, 4, 7,8,9,10,15,16,18,19,21,22,24,25, 26,27,28,29,30,31,34, 36,43,44,51,52,55, 56,57,62,66,73,74,77,82,83,84,85,87 and 92 showed 100% protection on be day where all the animals in the control group had died (days 24).

EXAMPLE 96

In vivo activity (systemic aspergillosis)

According to a similar in vivo model of systemic aspergillosis in mice, animals treated with the products of examples 3, 25, 26, 29, 51, and 57 (p.o. 20 mg/kg/day, 5 days) showed 60–100% protection on day 25 postinfection. Mortality in the control group on day 25 was 90%.

We claim:

1. A compound of formula I:

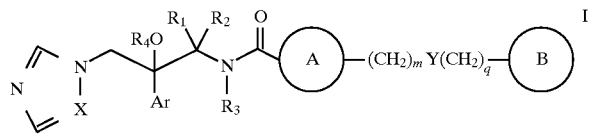

as a racemate, a diastereomer mixture or as a pure enantiomer, wherein:

X represents N;

Ar represents phenyl or phenyl substituted with one or more halogen and/or trifluoromethyl groups;

$R_{12}$ is $C_1$–$C_4$ alkyl;

$R_2$ is hydrogen or $C_1$–$C_4$ alkyl;

or $R_1$ together with $R_2$ form a $C_2$–$C_4$ polymethylene chain;

$R_3$ is hydrogen, $C_1$–$C_4$ alkyl, $C_3$–$C_6$ cycloalkyl, $C_3$–$C_6$ cycloalkyl-$C_1$–$C_4$ alkyl, $C_1$–$C_4$ haloalkyl, phenyl-$C_1$–$C_4$ alkyl (wherein the phenyl group can be optionally substituted with 1, 2, 3 or 4 groups $R_5$, which can be the same or different), a group —$(CH_2)_n$—$CH_2OH$, a group —$(CH_2)_n$—$CH_2OBn$, a group —$(CH_2)_n$—$CH_2NR_6R_7$, a group —$(CH_2)_n$—$CH_2COOR_6$, or a group —$(CH_2)_nCH_2COOBn$;

$R_4$ is hydrogen;

A represents phenyl, thiophene, furan, pyrrole, pyrazole, thiazole, imidazole, isothiazole, oxazole, isoxazole, 1,2,4-triazole, 1,3,4-oxadiazole, 1,3,4-thiadiazole, 1,2,4-oxadiazole, 1,2,4-thiadiazole, or their respective hydrogenated versions, wherein A can be unsubstituted or have 1, 2, 3 or 4 groups $R_8$;

B represents a phenyl group which can be optionally substituted with 1, 2, 3 or 4 groups $R_9$;

$R_5$ represents $C_1$–$C_4$ alkyl, $C_1$–$C_4$ haloalkyl or halogen;

n represents 0, 1, 2 or 3;

$R_6$ and $R_7$ independently represent hydrogen or $C_1$–$C_4$ alkyl;

$R_8$ represents $C_1$–$C_4$ alkyl, $C_3$–$C_6$ cycloalkyl, $C_1$–$C_4$ haloalkyl, $C_1$–$C_4$ alkoxy, $C_1$–$C_4$ haloalkoxy, halogen, phenyl (optionally substituted with a group halogen, cyano, $C_1$–$C_4$ haloalkyl or $C_1$–$C_4$ haloalkoxy), nitro, cyano, hydroxy, hydroxymethyl, a group —$NR_6R_7$, a group —$CONR_6R_7$, a group —$COR_6$, a group —$COOR_6$, or a group —$SO_2R_{10}$;

$R_9$ represents $C_1$–$C_4$ alkyl, $C_2$–$C_4$-alkenyl, $C_2$–$C_4$-alkynyl, $C_3$–$C_6$ cycloalkyl, $C_1$–$C_4$ haloalkyl, $C_1$–$C_4$ alkoxy, $C_1$–$C_4$ haloalkoxy, 2-carboxy-2-propyl, halogen, nitro, cyano, hydroxy, benzyloxy, hydroxymethyl, a group —$CH_2$—$OCO$—$R_6$, a group —$CO$—$R_6$, a group —$COO$—$R_6$, a group —$SO_2R_{10}$, a group —$NR_6R_7$, a group —$CONR_6R_7$, a group —$C(=NR_6)NHR_{11}$, a group —$C(=NR_{11})OR_6$, and additionally one of the groups $R_9$ can also represent 1-pyrrolyl, 1-imidazolyl, 1H-1,2,4-triazol-1-yl, 5-tetrazolyl (optionally substituted with $C_1$–$C_4$ alkyl), 1-pyrrolidinyl, 4-morpholinyl, 4-morpholinyl-N-oxide, phenyl or phenoxy (both optionally substituted with a group $C_1$–$C_4$ alkyl, $C_1$–$C_4$ haloalkyl, $C_1$–$C_4$ alkoxy, $C_1$–$C_4$ haloalkoxy, halogen, nitro or cyano), or a group of formula (i)–(iv)

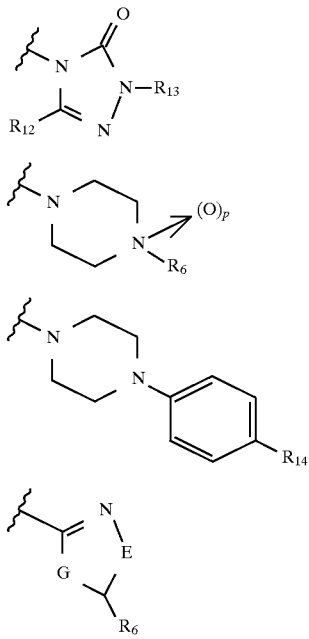

$R_{10}$ represents $C_1$–$C_4$ alkyl;

z represents 0, 1 or 2;

$R_{11}$ represents hydrogen, —$CONH_2$, —COMe, —CN, —$SO_2NHR_6$, —$SO_2R_{10}$, —$OR_6$, or —$OCOR_6$;

$R_{12}$ represents hydrogen or methyl;

$R_{13}$ represents hydrogen, isopropyl, cyclopentyl, cyclopropyl, 2-butyl, 3-pentyl, 3-hydroxy-2-butyl, or 2-hydroxy-3-pentyl;

p represents 0 or 1;

$R_{14}$ represents halogen, $C_1$–$C_4$ haloalkyl, $C_1$–$C_4$ haloalkoxy, nitro, amino, cyano, or a group of formula (i);

E represents —$CH_2$— or —C(=O)—;

G represents NH or O;

Y represents a single bond, —S—, —SO—, —$SO_2$—, —O— or —$NR_6$—;

m and q independently represent 0, 1 or 2; and the salts and solvates thereof.

2. A compound as claimed in claim 1 wherein $R_1$ represents $C_1$–$C_4$ alkyl and $R_2$ represents hydrogen.

3. A compound as claimed in claim 2 wherein $R_1$ represents methyl.

4. A compound as claimed in claim 1 $R_3$ represents hydrogen.

5. A compound as claimed in claim 1 wherein Ar represents 2-fluorophenyl, 4-fluorophenyl, 2-chloro-4-fluorophenyl, 2,4-dichlorophenyl, 2,4-difluorophenyl, 4-(trifluoromethyl)phenyl or 4-chlorophenyl.

6. A compound as claimed in claim 1 wherein A represents phenyl, wherein A can be unsubstituted or have 1, 2, 3 or 4 groups $R_8$.

7. a compound as claimed in claim 1 wherein A represents thiophene, furan, pyrrole, pyrazole, thiazole, imidazole, oxazole, isoxazole, 1,2,4-triazole, 1,3,4-oxadiazole, 1,3,4-thiadiazole, 1,2,4-oxadiazole or 1,2,4-thiadiazole, and which can be unsubstituted or have 1 or 2 groups $R_8$.

8. A compound as claimed in claim 1 wherein the stereochemistry of the compounds is (R,R).

9. A compound as claimed in claim 1 wherein:

$R_1$ represents methyl;

$R_2$ represents hydrogen;

$R_3$ represents hydrogen;

Ar represents 2-fluorophenyl, 2,4-dichlorophenyl, 2,4-difluorophenyl, 4-(trifluoromethyl)phenyl or 4-chlorophenyl;

A represents thiophene, furan, pyrrole, imidazole, pyrazole, thiazole, isothiazole, oxazole, isoxazole, 1,2,4-triazole, 1,3,4-oxadiazole, 1,3,4-thiadiazole, 1,2,4-oxadiazole, or 1,2,4-thiadiazole, wherein A can be optionally substituted with one or two $C_1$–$C_4$ alkyl or $C_1$–$C_4$ haloalkyl groups;

B represents a phenyl group substituted with 1 or 2 groups $R_9$;

$R_9$ represents $C_1$–$C_4$ alkyl, $C_2$–$C_4$-alkenyl, $C_2$–$C_4$-alkynyl, $C_3$–$C_6$ cycloalkyl, $C_1$–$C_4$ haloalkyl, $C_1$–$C_4$ alkoxy, $C_1$–$C_4$ haloalkoxy, 2-carboxy-2-propyl, halogen, nitro, cyano, hydroxy, benzyloxy, hydroxymethyl, a group —$CH_2$—OCO—$R_6$, a group —CO—$R_6$, a group —COO—$R_6$, a group —$SO_2R_{10}$, a group —$NR_6R_7$, a group —$CONR_6R_7$, a group —C(=$NR_6$)$NHR_{11}$ or a group —C(=$NR_{11}$)$OR_6$;

Y represents a single bond and m=q=0; and the stereochemistry of the compounds is (R,R).

10. A compound as claimed in claim 1 selected from:

(a) (1R,2R)-1-(4-chlorophenyl)-N-[2-(2,4-difluorophenyl)-2-hydroxy-1-methyl-3-(1H-1,2,4-triazol-1-yl)propyl]-5-methyl-1H-pyrazole-4-carboxamide;

(b) (1R,2R)-1-(4-chlorophenyl)-N-[2-(2,4-difluorophenyl)-2-hydroxy-1-methyl-3-(1H-1,2,4-triazol-1-yl)propyl]-5-trifluoromethyl-1H-pyrazole-4-carboxamide;

(c) (1R,2R)-1-(4-chlorophenyl)-N-[2-(2,4-difluorophenyl)-2-hydroxy-2-methyl-3(1H-1,2,4-tiazol-1-yl)propyl]-3,5dimethyl-1H-pyrazole-4-carboxamide;

(d) (1R,2R)-N-[2-(2,4difluorophenyl)-2-hydroxy-1-methyl-3-(1H-1,2,4 triazol-1-yl)propyl]-4-methyl-2-(4-trifluoromethylphenyl)thiazole-5-carboxamide;

(e) (1R,2R)-2-(4-chlorophenyl)-N-[2-(2,4-difluorophenyl)-2-hydroxy-1-methyl-3(1H-1,2,4-triazol-1-yl)propyl]-4-methylthiazole-5-carboxamide;

(f) (1R,2R)-N-[2-(2,4-difluorophenyl)-2-hydroxy-1-methyl-3-(1H-1,2,4- triazol-1-yl)propyl]-4-methyl-2-(4-trifluoromethoxyphenyl)thiazole-5-carboxamide;

(g) (1R, 2R)-2-(4 cyanophenyl)-N-[2-(2,4-difluorophenyl)-2-hydroxy-1-methyl-3(1H-1,2,4-triazol-1-yl)propyl]-4-methylthiazole-5-carboxamide;

(h) (1R,2R)-5-(4-chlorophenyl)-N-[2-(2,4-difluorophenyl)-2-hydroxy-1-methyl-3-(1H-1,2,4-triazol-1-yl)propyl]thiophene-2-carboxamide;

(i) (1R, 2R,)-5-(4chlorophenyl)-N-[2-(2,4-difluorophenyl)-2-hydroxy-1-methyl-3-(1H-1,2,4triazol-1-yl)propyl]-3-methylthiophene-2-carboxamide;

(j) (1R,2R)-5-(4cyanophenyl)-N-[2-(2,4-difluorophenyl)-2-hydroxy-1-methyl-3-(1H-1,2,4-triazol-1-yl)propyl]-3-methylthiophene-2-carboxamide;

(k) (1R,2R)-2-(4-cyanophenyl)-N-[2-(2-fluorophenyl)-2-hydroxy-1-methyl-3-(1H-1,2,4triazol-1-yl)propyl]-methylthiazole-5-carboxamide;

(l) (1R,2R)-N-[2-(2,4-difluorophenyl)-2-hydroxy-1-methyl-3-(1H-1,2,4-triazol-1-yl)propyl]-2-(4fluorophenyl)-4-methylthiazole-5-carboxamide; or a salt or solvate thereof.

11. A process for preparing a compound of formula I as defined in claim 1, which comprises:

(a) reacting a compound of formula II

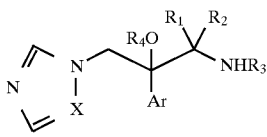

wherein X, $R_1$, $R_2$, $R_3$, $R_4$ and Ar are as defined in claim 1, with an acid of formula III

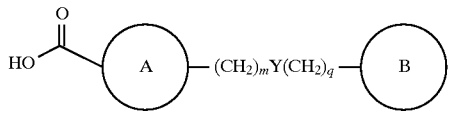

wherein A, B, Y, m and q are as defined in claim 1, in the presence of a condensing agent, or with a reactive derivative of said acid III in the presence of a proton scavenger base; or (b) converting in one or a plurality of steps a compound of formula I into another compound of formula I; and (c) if desired, after steps (a) or (b), reacting a compound of formula I with an acid to give the corresponding acid addition salt.

12. The process according to claim 11, wherein the reactive derivative of said acid III is an acid chloride, an anhydride or a mixed anhydride.

13. A pharmaceutical composition which comprises an effective amount of a compound of formula I as claimed in claim 1 or a pharmaceutically acceptable salt or solvate thereof in admixture with one or more pharmaceutically acceptable excipients.

14. An agrochemical composition which comprises a compound of formula I as claimed in claim 1 or a salt or solvate thereof in admixture with one or more agrochemically acceptable excipients.

15. A method for the treatment or prevention of a fungal infection in an animal, said method comprising administering a compound of formula I as claimed in claim 1 or a pharmaceutically acceptable salt or solvate thereof to an animal in need of such treatment or prevention.

16. The method of claim 15, wherein said animal is a human.

17. A method for the treatment or prevention of a fungal infection in a plant, said method comprising applying a compound of formula I as claimed in claim 1, or a salt or solvate thereof to a plant in need of such treatment or prevention.

18. A compound as claimed in claim 1 wherein:

A represents phenyl, thiophene, furan, pyrrole, pyrazole, thiazole, imidazole, isothiazole, oxazole or isoxazole, optionally substituted with 1, 2, 3 or 4 groups $R_8$.

19. A compound as claimed in claim 1 wherein

A represents phenyl, thiophene, furan, pyrrole, pyrazole, thiazole, imidazole, isothiazole, oxazole, isoxazole, 1,2,4-triazole, 1,3,4-oxadiazole, 1,3,4-thiadiazole, 1,2,4-oxadiazole, 1,2,4-thiadiazole, pyrroline, imidazoline or pyrazoline, optionally substituted with 1, 2, 3 or 4 groups $R_8$.

* * * * *